(12) United States Patent
Chamoin et al.

(10) Patent No.: US 8,809,545 B2
(45) Date of Patent: Aug. 19, 2014

(54) ARYL PYRIDINE AS ALDOSTERONE SYNTHASE INHIBITORS

(71) Applicants: Sylvie Chamoin, Saint Louis (FR); Qi-Ying Hu, Needham, MA (US); Julien Papillon, Somerville, MA (US)

(72) Inventors: Sylvie Chamoin, Saint Louis (FR); Qi-Ying Hu, Needham, MA (US); Julien Papillon, Somerville, MA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 13/939,232

(22) Filed: Jul. 11, 2013

(65) Prior Publication Data

US 2013/0296309 A1    Nov. 7, 2013

Related U.S. Application Data

(63) Continuation of application No. 13/615,902, filed on Sep. 14, 2012, now Pat. No. 8,519,142, which is a continuation of application No. 12/780,025, filed on May 14, 2010, now Pat. No. 8,383,827.

(60) Provisional application No. 61/318,413, filed on Mar. 29, 2010, provisional application No. 61/178,677, filed on May 15, 2009.

(51) Int. Cl.
| C07D 405/04 | (2006.01) |
| C07D 401/04 | (2006.01) |
| C07D 417/04 | (2006.01) |

(52) U.S. Cl.
USPC ...... 546/338; 546/167; 546/284.1; 546/270.1; 514/314; 514/338; 514/357

(58) Field of Classification Search
CPC ............................ C07D 401/04; C07D 407/07
See application file for complete search history.

(56) References Cited

U.S. PATENT DOCUMENTS

| 8,044,198 B2 | 10/2011 | Nunes et al. |
| 8,383,827 B2 | 2/2013 | Chamoin et al. |
| 2003/0199511 A1 | 10/2003 | Li et al. |
| 2005/0038247 A1 | 2/2005 | Charifson et al. |
| 2005/0256136 A1 | 11/2005 | Charifson et al. |
| 2006/0025424 A1 | 2/2006 | Charifson et al. |
| 2006/0270686 A1 | 11/2006 | Kelly et al. |
| 2008/0021070 A1 | 1/2008 | Barre et al. |
| 2009/0163489 A1 | 6/2009 | Booker et al. |
| 2010/0179143 A1 | 7/2010 | Adams et al. |
| 2010/0311736 A1 | 12/2010 | Adams et al. |
| 2011/0082129 A1 | 4/2011 | Adams et al. |
| 2012/0071514 A1 | 3/2012 | Hu et al. |
| 2013/0035354 A1 | 2/2013 | Chamoin et al. |

FOREIGN PATENT DOCUMENTS

| EP | 0 067 511 A2 | 12/1982 |
| FR | 2 876 691 A1 | 4/2006 |
| JP | 2006/182697 A | 7/2006 |
| WO | WO 95/26957 A1 | 10/1995 |
| WO | WO 95/28400 A1 | 10/1995 |
| WO | WO 96/31475 A2 | 10/1996 |
| WO | WO 00/44201 A1 | 6/2001 |
| WO | WO 02/22579 A2 | 3/2002 |
| WO | WO 03/053941 A2 | 7/2003 |
| WO | 2006/010546 A2 | 2/2006 |
| WO | WO 2006/051270 A1 | 5/2006 |
| WO | WO 2006/051311 A1 | 5/2006 |
| WO | WO 2006/065946 A1 | 6/2006 |
| WO | WO 2006/125208 A1 | 11/2006 |
| WO | WO 2006/129199 A1 | 12/2006 |
| WO | WO 2007/019344 A1 | 2/2007 |
| WO | WO 2007/019345 A1 | 2/2007 |
| WO | WO 2007/019346 A1 | 2/2007 |
| WO | WO 2007/019417 A1 | 2/2007 |
| WO | WO 2007/091140 A1 | 8/2007 |
| WO | WO 2007/104560 A1 | 9/2007 |
| WO | WO 2007/129044 A1 | 11/2007 |
| WO | WO 2008/022286 A2 | 2/2008 |
| WO | WO 2008/028937 A1 | 3/2008 |
| WO | WO 2008/042867 A2 | 4/2008 |
| WO | WO 2008/141065 A1 | 11/2008 |
| WO | WO 2008/144463 A1 | 11/2008 |
| WO | WO 2008/144464 A1 | 11/2008 |
| WO | WO2008/150827 A1 | 12/2008 |
| WO | WO 2008/157191 A2 | 12/2008 |
| WO | WO 2009/017822 A2 | 2/2009 |

(Continued)

OTHER PUBLICATIONS

Myers; "Non-steroidal mineralocorticoid receptor antagonists"; Expert Opinion Ther Patents 17(1):17-23 (2007).

(Continued)

*Primary Examiner* — Nyeemah A Grazier
(74) *Attorney, Agent, or Firm* — Sophie Binet Cross

(57) ABSTRACT

The present invention provides a compound of formula I;

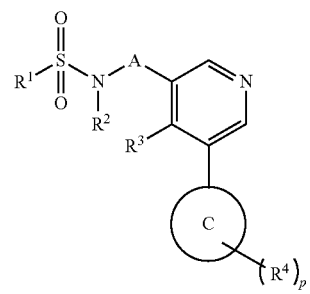

a method for manufacturing the compounds of the invention, and its therapeutic uses. The present invention further provides a combination of pharmacologically active agents and a pharmaceutical composition.

12 Claims, No Drawings

(56) References Cited

FOREIGN PATENT DOCUMENTS

| WO | WO 2009/039140 A1 | 3/2009 |
| WO | WO 2009/040289 A2 | 4/2009 |
| WO | WO 2009/055418 A1 | 4/2009 |
| WO | WO 2009/068482 A1 | 6/2009 |
| WO | WO 2009/096198 A1 | 8/2009 |
| WO | WO 2009/147187 A1 | 12/2009 |
| WO | WO 2009/155527 A2 | 12/2009 |
| WO | WO 2009/156462 A2 | 12/2009 |
| WO | 2010/108074 | 9/2010 |

OTHER PUBLICATIONS

Jacquemard et al; "Synthesis of 3,5-bis(2-indolyl)pyridine and 3-[(2-indolyl)-5-phenyl]-pyridine derivatives as CDK inhibitors and cytotoxic agents"; Bioorganic & Medicinal Chemistry 16(9):4932-4952 (2008).

ARYL PYRIDINE AS ALDOSTERONE SYNTHASE INHIBITORS

This application is a continuation application of U.S. application Ser. No. 13/615,902 filed on Sep. 14, 2012, which claims benefit under 35 U.S.C. §120 of U.S. patent application Ser. No. 12/780,025, filed on May 14, 2010, which claims benefit under 35 U.S.C. §119(e) of U.S. Provisional Application No. 61/178,677, filed May 15, 2009, and U.S. Provisional Application No. 61/318,413, filed on Mar. 29, 2010; the contents of which are incorporated herein by reference in their entirety.

BACKGROUND OF THE INVENTION

The mineralocorticoid hormone aldosterone is produced by the adrenal gland and acts on the distal tubules and collecting ducts of the kidney to increase reabsorption of ions and water in the kidney. Aldosterone causes conservation of sodium, secretion of potassium, increased water retention, and increased blood pressure.

Aldosterone has been implicated in the pathogenesis of cardiovascular diseases such as hypertension and heart failure. In clinical trials, treatment with the nonselective mineralocorticoid receptor antagonist (MRA) spironolactone or the selective MRA eplerenone significantly reduced morbidity and mortality among patients with heart failure or myocardial infarction already taking an angiotensin-converting enzyme inhibitor or a β-blocker. However, significant side effects such as gynecomastia and impotence were observed in male patients receiving spironolactone while hyperkalemia was seen in patients taking either drug.

SUMMARY OF THE INVENTION

The invention pertains to the compounds, methods for using them, and uses thereof as described herein. Examples of compounds of the invention include the compounds according to any one of the Formulae I' and I-VII, and the compounds of the examples, or a pharmaceutically acceptable salt thereof.

The invention therefore provides a compound of the Formula I':

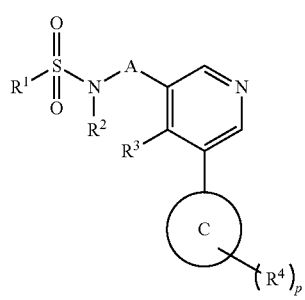

I' or a pharmaceutically acceptable salt thereof, wherein
A is a bond, —$CH_2$—, —$CHR^5$—, —$CR^5R^6$— or —$CR^{5a}R^{6a}$—$CR^{5b}R^{6b}$;
Ring C is a phenyl or a 5- or 6-membered heteroaryl;
$R^1$ is $C_{1-7}$alkyl, haloalkyl, $C_{3-7}$cycloalkyl, $C_{6-10}$aryl, $C_{6-10}$aryl-$C_{1-7}$alkyl, $C_{6-10}$aryloxy-$C_{1-7}$alkyl, heteroaryl or heterocyclyl in which alkyl, aryl, heteroaryl, heterocyclyl are optionally substituted with 1 to 5 $R^7$;

$R^2$ is H, $C_{1-7}$alkyl, halo-$C_{1-7}$alkyl, $C_{3-7}$cycloalkyl, $C_{3-7}$cycloalkyl-$C_{1-7}$alkyl, hydroxy-$C_{1-7}$alkyl, $C_{1-7}$alkyl-O—C(O)$C_{1-7}$alkyl, $C_{1-7}$alkoxy-$C_{1-7}$alkyl, heteroaryl, heterocycyl, or $C_{6-10}$aryl; wherein aryl and heteroaryl are optionally substituted with hydroxy, $C_{1-7}$alkoxy, $C_{1-7}$alkyl, halo-$C_{1-7}$alkyl, halo, CN or $C_{3-7}$cycloalkyl;
$R^3$ is H, halo, $C_{1-7}$alkyl, halo-$C_{1-7}$alkyl, $C_{3-7}$cycloalkyl, cyano, $C_{1-7}$alkoxy, hydroxy, nitro, —$NH_2$, —NH($C_{1-7}$alkyl) or —N($C_{1-7}$alkyl)$_2$;
each $R^4$ is independently selected from the group consisting of halo, $C_{1-7}$alkyl, halo-$C_{1-7}$alkyl, $C_{3-7}$cycloalkyl, cyano, —$NH_2$, —NH($C_{1-7}$alkyl), —N($C_{1-7}$alkyl)$_2$, $C_{1-7}$alkoxy, halo-$C_{1-7}$alkoxy, hydroxy, carboxy, nitro, sulfonyl, sulfamoyl, sulfonamido, $C_{6-10}$aryl, heterocyclyl, $C_{6-10}$aryloxy, heterocyclyloxy, —SH, —S—$C_{1-7}$alkyl, —C(O)O—$C_{6-10}$aryl, —C(O)O-heterocyclyl, —C(O)O-heteroaryl, —C(O)$NR^2$—$C_{1-7}$alkyl, —C(O)$NR^2$—$C_{6-10}$aryl, —C(O)$NR^2$-heteroaryl, —C(O)$NR^2$-heterocyclyl, —$NR^2$C(O)—$C_{1-7}$alkyl, —$NR^2$C(O)—$C_{6-10}$aryl, —$NR^2$C(O)-heteroaryl, —$NR^2$C(O)-heterocyclyl, —OC(O)—$C_{1-7}$alkyl, —OC(O)—$C_{6-10}$aryl, —OC(O)-heteroaryl and —OC(O)-heterocyclyl; wherein $R^4$ is optionally substituted with 1 to 5 $R^7$; or
two adjacent $R^4$ groups can form with the atoms to which they are attached a phenyl or a 5- or 6-membered ring heteroaryl, in which said phenyl or heteroaryl ring is optionally substituted with 1 to 4 $R^8$;
$R^5$ and $R^6$ are independently $C_{1-7}$alkyl, $C_{3-7}$cycloalkyl, halo-$C_{1-7}$alkyl, heterocyclyl, heteroaryl or $C_{6-10}$aryl; or $R^5$ and $R^6$ form together with the atom to which they are attached a $C_{3-7}$cycloalkyl;
$R^{5a}$, $R^{6a}$, $R^{5b}$ and $R^{6b}$ are independently H, $C_{1-7}$alkyl, $C_{3-7}$cycloalkyl, halo-$C_{1-7}$alkyl, heterocyclyl, heteroaryl or $C_{6-10}$aryl; or any two of $R^{5a}$, $R^{6a}$, $R^{5b}$ and $R^{6b}$ form together with the atom(s) to which they are attached a $C_{3-7}$cycloalkyl;
each $R^7$ is independently selected from the group consisting of halo, $C_{1-7}$alkyl, $C_{3-7}$ cycloalkyl, $C_{1-7}$alkoxy, $C_{6-10}$aryloxy, heterocyclyl, $C_{6-10}$aryl, heteroaryl, CN and halo-$C_{1-7}$alkyl;
each $R^8$ is independently selected from the group consisting of halo, $C_{1-7}$alkyl, halo-$C_{1-7}$alkyl, $C_{1-7}$alkoxy, CN and halo-$C_{1-7}$alkoxy; or
$R^2$ and $R^3$; $R^1$ and $R^2$; $R^1$ and $R^5$; $R^1$ and $R^{5a}$; $R^1$ and $R^{5b}$; $R^2$ and $R^{5a}$; $R^2$ and $R^{5b}$; $R^1$ and $R^3$; or $R^2$ and $R^5$ can form with the atoms to which they are attached a 4- to 7-membered heterocyclyl; or
$R^3$ and $R^5$; $R^3$ and $R^{5b}$; or $R^3$ and $R^{5a}$ can form together with the atoms to which they are attached a $C_{5-7}$cycloalkyl; and
wherein each heteroaryl is a monocyclic aromatic ring comprising 5 or 6 ring atoms selected from carbon atoms and 1 to 5 heteroatoms, and
each heterocyclyl is a monocyclic saturated or partially saturated but non-aromatic moiety comprising 4-7 ring atoms selected from carbon atoms and 1 to 3 heteroatoms; and each heteroatoms being O, N or S; and
p is 0, 1, 2, 3, 4 or 5, with the proviso that Ring C together with two adjacent $R^4$ groups do not form a 2-indole; and
when Ring C is pyridine, thiazole, imidazole or pyrazole and two adjacent $R^4$ groups do not form with the atoms to which they are attached a phenyl or a 5- or 6-membered ring heteroaryl, than A is not a bond; and
when Ring C together with two adjacent $R^4$ groups form oxazolo[4,5-b]pyiridine, than A is not a bond; and the compound of Formula I' is not 2-methyl-N-(6-(5-(phenylsulfonamido)pyridin-3-yl)-1H-indazol-4-yl)thiazole-4-carboxamide, 2-chloro-N-isobutyl-N-((5-(3-(methylsulfonyl)phenyl)pyridin-3-yl)methyl)benzenesulfonamide or 4-(5-(4-chloro-2,5-dimethylphenylsulfonamido)pyridin-3-yl)benzoic acid.

In another embodiment, the invention pertains, at least in part, to a method for treating a disorder or disease mediated by aldosterone synthase and/or 11-beta hydroxylase (CYP11B1) in a subject by administering to the subject a therapeutically effective amount of a compound according to any one of the Formulae I' and I-VII, or a pharmaceutically acceptable salt thereof, such that the disorder or disease mediated by aldosterone synthase and/or CYP11B1 in the subject is treated.

In yet another embodiment, the invention pertains, at least in part, to a method for treating a subject for hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess, comprising administering to the subject a therapeutically effective amount of a compound according to any one of Formulae I' and I-VII, or a pharmaceutically acceptable salt thereof, such that the subject is treated.

In yet another embodiment, the invention pertains, at least in part, to pharmaceutical compositions, comprising an effective amount of a compound according to any one of Formulae I' and I-VII, or a pharmaceutically acceptable salt thereof, wherein said effective amount is effective to treat a disorder or disease mediated by aldosterone synthase and/or CYP11B1.

In still another embodiment, the invention pertains, at least in part, to combinations including pharmaceutical combinations of one or more therapeutically active agents of any one of Formulae I' and I-VII, or a pharmaceutically acceptable salt thereof.

In another embodiment, the invention pertains, at least in part, to a method for inhibiting aldosterone synthase and/or CYP11B1 in a subject by administering to the subject a therapeutically effective amount of a compound according to any one of the Formulae I' and I-VII, or a pharmaceutically acceptable salt thereof, such that aldosterone synthase and/or CYP11B1 is inhibited.

An approach to ameliorate the deleterious effects of aldosterone, provided by the present invention, is the suppression of aldosterone production by aldosterone synthase inhibitors. Aldosterone synthase is an enzyme responsible for the final steps of the biosynthesis of aldosterone from deoxycorticosterone, via conversion of corticosterone to form 18-OH-corticosterone, which is then converted to aldosterone.

Accordingly, the invention pertains, at least in part, to compounds, pharmaceutical compositions containing the compound and methods of use thereof. The present invention also relates to novel compounds which may be used, for example, as modulators and/or inhibitors of aldosterone synthase and/or CYP11B1.

The compounds of the present invention may, for example, be used to treat various diseases or disorders mediated by aldosterone synthase such as hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, fibrinoid necrosis of coronary arteries, Cushing's syndrome, excessive cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess.

DETAILED DESCRIPTION OF THE INVENTION

Compounds of the Invention

References hereinafter to compounds of Formula I or I' apply equally to compounds of Formulae II-VII.

References hereinafter to embodiments of the invention apply equally to compounds of Formula I or I' and compounds of Formulae II-VII, insofar as the embodiments are present.

Various embodiments of the invention are described herein. It will be recognized that features specified in each embodiment may be combined with other specified features to provide further embodiments.

In one embodiment the invention provides a compound of the Formula I'

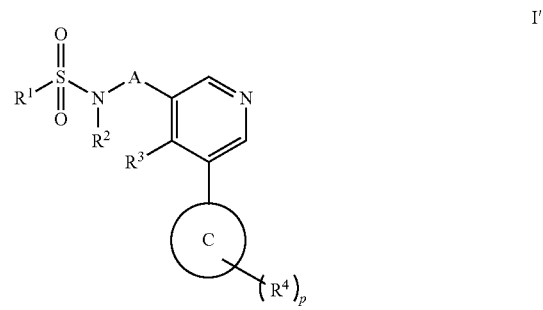

or a pharmaceutically acceptable salt thereof, wherein
A is a bond, —$CH_2$—, —$CHR^5$—, —$CR^5R^6$— or —$CR^{5a}R^{6a}$—$CR^{5b}R^{6b}$—;

Ring C is a phenyl or a 5- or 6-membered heteroaryl;
$R^1$ is $C_{1-7}$alkyl, haloalkyl, $C_{3-7}$cycloalkyl, $C_{6-10}$aryl, $C_{6-10}$aryl-$C_{1-7}$alkyl, $C_{6-10}$aryloxy-$C_{1-7}$alkyl, heteroaryl or heterocyclyl in which alkyl, aryl, heteroaryl, heterocyclyl are optionally substituted with 1 to 5 $R^7$;
$R^2$ is H, $C_{1-7}$alkyl, halo-$C_{1-7}$alkyl, $C_{3-7}$cycloalkyl, $C_{3-7}$cycloalkyl-$C_{1-7}$alkyl, hydroxy-$C_{1-7}$alkyl, $C_{1-7}$alkyl-O—C(O)$C_{1-7}$alkyl, $C_{1-7}$alkoxy-$C_{1-7}$alkyl, heteroaryl, heterocycyl, or $C_{6-10}$aryl;
wherein aryl and heteroaryl are optionally substituted with hydroxy, $C_{1-7}$alkoxy, $C_{1-7}$alkyl, halo-$C_{1-7}$alkyl, halo, CN or $C_{3-7}$cycloalkyl;
$R^3$ is H, halo, $C_{1-7}$alkyl, halo-$C_{1-7}$alkyl, $C_{3-7}$cycloalkyl, cyano, $C_{1-7}$alkoxy, hydroxy, nitro, —$NH_2$, —NH($C_{1-7}$alkyl) or —N($C_{1-7}$alkyl)$_2$;
each $R^4$ is independently selected from the group consisting of halo, $C_{1-7}$alkyl, halo-$C_{1-7}$alkyl, $C_{3-7}$cycloalkyl, cyano, —$NH_2$, —NH($C_{1-7}$alkyl), —N($C_{1-7}$alkyl)$_2$, $C_{1-7}$alkoxy, halo-$C_{1-7}$alkoxy, hydroxy, carboxy, nitro, sulfonyl, sulfamoyl, sulfonamido, $C_{6-10}$aryl, heterocyclyl, $C_{6-10}$aryloxy, heterocyclyloxy, —SH, —S—$C_{1-7}$alkyl, —C(O)O—$C_{6-10}$aryl, —C(O)O-heterocyclyl, —C(O)O-heteroaryl, —C(O)NR$^2$—$C_{1-7}$alkyl, —C(O)NR$^2$—$C_{6-10}$aryl, —C(O)NR$^2$-heteroaryl, —C(O)NR$^2$-heterocyclyl, —NR$^2$C(O)—$C_{1-7}$alkyl, —NR$^2$C(O)—$C_{6-10}$aryl, —NR$^2$C(O)-heteroaryl, —NR$^2$C(O)-heterocyclyl, —OC(O)—$C_{1-7}$alkyl, —OC(O)—$C_{6-10}$aryl, —OC(O)-heteroaryl and —OC(O)-heterocyclyl;
wherein $R^4$ is optionally substituted with 1 to 5 $R^7$; or
two adjacent $R^4$ groups can form with the atoms to which they are attached a phenyl or a 5- or 6-membered ring heteroaryl, in which said phenyl or heteroaryl ring is optionally substituted with 1 to 4 $R^8$;
$R^5$ and $R^6$ are independently $C_{1-7}$alkyl, $C_{3-7}$cycloalkyl, halo-$C_{1-7}$alkyl, heterocyclyl, heteroaryl or $C_{6-10}$aryl; or $R^5$ and $R^6$ form together with the atom to which they are attached a $C_{3-7}$cycloalkyl;
$R^{5a}$, $R^{6a}$, $R^{5b}$ and $R^{6b}$ are independently H, $C_{1-7}$alkyl, $C_{3-7}$cycloalkyl, halo-$C_{1-7}$alkyl, heterocyclyl, heteroaryl or $C_{6-10}$aryl; or any two of $R^{5a}$, $R^{6a}$, $R^{5b}$ and $R^{6b}$ form together with the atom(s) to which they are attached a $C_{3-7}$cycloalkyl;
each $R^7$ is independently selected from the group consisting of halo, $C_{1-7}$alkyl, $C_{3-7}$cycloalkyl, $C_{1-7}$alkoxy, $C_{6-10}$aryloxy, heterocyclyl, $C_{6-10}$aryl, heteroaryl, CN and halo-$C_{1-7}$alkyl;
each $R^8$ is independently selected from the group consisting of halo, $C_{1-7}$alkyl, halo-$C_{1-7}$alkyl, $C_{1-7}$alkoxy, CN and halo-$C_{1-7}$alkoxy; or
$R^2$ and $R^3$; $R^1$ and $R^2$; $R^1$ and $R^5$; $R^1$ and $R^{5a}$; $R^1$ and $R^{5b}$, $R^2$ and $R^{5a}$; $R^2$ and $R^{5b}$; $R^1$ and $R^3$; or $R^2$ and $R^5$ can form with the atoms to which they are attached a 4- to 7-membered heterocyclyl; or
$R^3$ and $R^5$; $R^3$ and $R^{5b}$; or $R^3$ and $R^{5a}$ can form together with the atoms to which they are attached a $C_{5-7}$cycloalkyl; and
wherein each heteroaryl is a monocyclic aromatic ring comprising 5 or 6 ring atoms selected from carbon atoms and 1 to 5 heteroatoms, and
each heterocyclyl is a monocyclic saturated or partially saturated but non-aromatic moiety comprising 4-7 ring atoms selected from carbon atoms and 1 to 3 heteroatoms; and each heteroatoms being O, N or S; and
p is 0, 1, 2, 3, 4 or 5, with the proviso that Ring C together with two adjacent $R^4$ groups do not form a 2-indole; and
when Ring C is pyridine, thiazole, imidazole or pyrazole and two adjacent $R^4$ groups do not form with the atoms to which they are attached a phenyl or a 5- or 6-membered ring heteroaryl, than A is not a bond; and
when Ring C together with two adjacent $R^4$ groups form oxazolo[4,5-b]pyiridine, than A is not a bond; and the compound of Formula I' is not 2-methyl-N-(6-(5-(phenylsulfonamido)pyridin-3-yl)-1H-indazol-4-yl)thiazole-4-carboxamide, 2-chloro-N-isobutyl-N-((5-(3-(methylsulfonyl)phenyl)pyridin-3-yl)methyl)benzenesulfonamide or 4-(5-(4-chloro-2,5-dimethylphenylsulfonamido)pyridin-3-yl)benzoic acid.

In one embodiment the invention pertains to a compound of the Formula I:

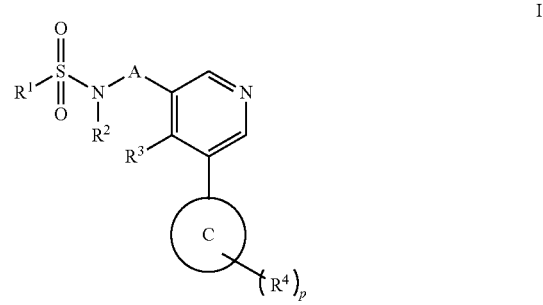

I or a pharmaceutically acceptable salt thereof, wherein
A is a bond, —$CH_2$—, —$CHR^5$—, —$CR^5R^6$— or —$CR^{5a}R^{6a}$—$CR^{5b}R^{6b}$—;
Ring C is a phenyl or a 5- or 6-membered heteroaryl;
$R^1$ is $C_{1-7}$alkyl, haloalkyl, $C_{3-7}$cycloalkyl, $C_{6-10}$aryl, $C_{6-10}$aryl-$C_{1-7}$alkyl, $C_{6-10}$aryloxy-$C_{1-7}$alkyl, heteroaryl or heterocyclyl in which alkyl, aryl, heteroaryl, heterocyclyl are optionally substituted with 1 to 5 $R^7$;
$R^2$ is H, $C_{1-7}$alkyl, halo-$C_{1-7}$alkyl, $C_{3-7}$cycloalkyl, heteroaryl, heterocycyl or $C_{6-10}$aryl;
$R^3$ is H, halo, $C_{1-7}$alkyl, halo-$C_{1-7}$alkyl, $C_{3-7}$cycloalkyl, cyano, $C_{1-7}$alkoxy, hydroxy, nitro, —$NH_2$, —NH($C_{1-7}$alkyl) or —N($C_{1-7}$alkyl)$_2$;
each $R^4$ is independently selected from the group consisting of halo, $C_{1-7}$alkyl, halo-$C_{1-7}$alkyl, $C_{3-7}$cycloalkyl, cyano, —$NH_2$, —NH($C_{1-7}$alkyl), —N($C_{1-7}$alkyl)$_2$, $C_{1-7}$alkoxy, halo-$C_{1-7}$alkoxy, hydroxy, carboxy, nitro, sulfonyl, sulfamoyl, sulfonamido, $C_{6-10}$aryl, heterocyclyl, $C_{6-10}$aryloxy, heterocyclyloxy, —SH, —S—$C_{1-7}$alkyl, —C(O)O—$C_{6-10}$aryl, —C(O)O-heterocyclyl, —C(O)O-heteroaryl, —C(O)NR$^2$—$C_{1-7}$alkyl, —C(O)NR$^2$—$C_{6-10}$aryl, —C(O)NR$^2$-heteroaryl, —C(O)NR$^2$-heterocyclyl, —NR$^2$C(O)—$C_{1-7}$alkyl, —NR$^2$C(O)—$C_{6-10}$aryl, —NR$^2$C(O)-heteroaryl, —NR$^2$C(O)-heterocyclyl, —OC(O)—$C_{1-7}$alkyl, —OC(O)—$C_{6-10}$aryl, —OC(O)-heteroaryl and —OC(O)-heterocyclyl;
wherein $R^4$ is optionally substituted with 1 to 5 $R^7$; or
two adjacent $R^4$ groups can form with the atoms to which they are attached a phenyl or a 5- or 6-membered ring heteroaryl, in which said phenyl or heteroaryl ring is optionally substituted with 1 to 4 $R^8$;
$R^5$ and $R^6$ are independently $C_{1-7}$alkyl, $C_{3-7}$cycloalkyl, halo-$C_{1-7}$alkyl, heterocyclyl, heteroaryl or $C_{6-10}$aryl; or $R^5$ and $R^6$ form together with the atom to which they are attached a $C_{3-7}$cycloalkyl;
$R^{5a}$, $R^{6a}$, $R^{5b}$ and $R^{6b}$ are independently H, $C_{1-7}$alkyl, $C_{3-7}$cycloalkyl, halo-$C_{1-7}$alkyl, heterocyclyl, heteroaryl or $C_{6-10}$aryl; or any two of $R^{5a}$, $R^{6a}$, $R^{5b}$ and $R^{6b}$ form together with the atom(s) to which they are attached a $C_{3-7}$cycloalkyl;
each $R^7$ is independently selected from the group consisting of halo, $C_{1-7}$alkyl, $C_{3-7}$cycloalkyl, $C_{1-7}$alkoxy, $C_{6-10}$aryloxy, heterocyclyl, $C_{6-10}$aryl, heteroaryl, CN and halo-$C_{1-7}$alkyl;
each $R^8$ is independently selected from the group consisting of halo, $C_{1-7}$alkyl, halo-$C_{1-7}$alkyl, $C_{1-7}$alkoxy, CN, and halo-$C_{1-7}$alkoxy; or $R^2$ and $R^3$; $R^1$ and $R^2$; $R^1$ and $R^5$; $R^1$ and $R^{5a}$; $R^1$ and $R^{5b}$; $R^2$ and $R^{5a}$; $R^2$ and $R^{5b}$; or $R^2$ and $R^5$ can form with the atoms to which they are attached a 4- to 7-membered heterocyclyl; or $R^3$ and $R^5$; $R^3$ and $R^{5b}$; or $R^3$ and $R^{5a}$ can form together with the atoms to which they are attached a $C_{5-7}$cycloalkyl; and wherein each heteroaryl is a monocyclic aromatic ring comprising 5 or 6 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1 to 3 heteroatoms; and each heteroatoms being O, N or S; and p is 0, 1, 2, 3, 4 or 5, with the proviso that Ring C together with two adjacent $R^4$ groups do not form a 2-indole.

In another embodiment the invention provides a compound of the Formula I

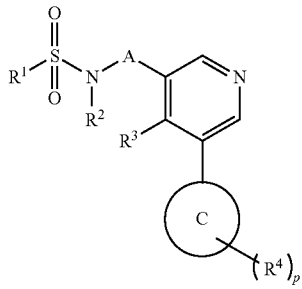

I or a pharmaceutically acceptable salt thereof, wherein

A is a bond, —$CH_2$—, —$CHR^5$—, —$CR^5R^6$— or —$CR^{5a}R^{6a}$—$CR^{5b}R^{6b}$—;

Ring C is a phenyl or a 5- or 6-membered heteroaryl;

$R^1$ is $C_{1-7}$alkyl, haloalkyl, $C_{3-7}$cycloalkyl, $C_{6-10}$aryl, $C_{6-10}$aryl-$C_{1-7}$alkyl, $C_{6-10}$aryloxy-$C_{1-7}$alkyl, heteroaryl or heterocyclyl in which alkyl, aryl, heteroaryl, heterocyclyl are optionally substituted with 1 to 5 $R^7$;

$R^2$ is H, $C_{1-7}$alkyl, halo-$C_{1-7}$alkyl, $C_{3-7}$cycloalkyl, heteroaryl, heterocycyl or $C_{6-10}$aryl;

$R^3$ is H, halo, $C_{1-7}$alkyl, halo-$C_{1-7}$alkyl, $C_{3-7}$cycloalkyl, cyano, $C_{1-7}$alkoxy, hydroxy, nitro, —$NH_2$, —$NH(C_{1-7}alkyl)$ or —$N(C_{1-7}alkyl)_2$;

each $R^4$ is independently selected from the group consisting of halo, $C_{1-7}$alkyl, halo-$C_{1-7}$alkyl, $C_{3-7}$cycloalkyl, cyano, —$NH_2$, —$NH(C_{1-7}alkyl)$, —$N(C_{1-7}alkyl)_2$, $C_{1-7}$alkoxy, halo-$C_{1-7}$alkoxy, hydroxy, carboxy, nitro, sulfonyl, sulfamoyl, sulfonamido, $C_{6-10}$aryl, heterocyclyl, $C_{6-10}$aryloxy, heterocyclyloxy, —SH, —S—$C_{1-7}$alkyl, —C(O)O—$C_{6-10}$aryl, —C(O)O-heterocyclyl, —C(O)O-heteroaryl, —C(O)$NR^2$—$C_{1-7}$alkyl, —C(O)$NR^2$—$C_{6-10}$aryl, —C(O)$NR^2$-heteroaryl, —C(O)$NR^2$-heterocyclyl, —$NR^2$C(O)—$C_{1-7}$alkyl, —$NR^2$C(O)—$C_{6-10}$aryl, —$NR^2$C(O)-heteroaryl, —$NR^2$C(O)-heterocyclyl, —OC(O)—$C_{1-7}$alkyl, —OC(O)—$C_{6-10}$aryl, —OC(O)-heteroaryl and —OC(O)-heterocyclyl; wherein $R^4$ is optionally substituted with 1 to 5 $R^7$; or two adjacent $R^4$ groups can form with the atoms to which they are attached a phenyl or a 5- or 6-membered ring heteroaryl, in which said phenyl or heteroaryl ring is optionally substituted with 1 to 4 $R^8$;

$R^5$ and $R^6$ are independently $C_{1-7}$alkyl, $C_{3-7}$cycloalkyl, halo-$C_{1-7}$alkyl, heterocyclyl, heteroaryl or $C_{6-10}$aryl; or $R^5$ and $R^6$ form together with the atom to which they are attached a $C_{3-7}$cycloalkyl;

$R^{5a}$, $R^{6a}$, $R^{5b}$ and $R^{6b}$ are independently H, $C_{1-7}$alkyl, $C_{3-7}$cycloalkyl, halo-$C_{1-7}$alkyl, heterocyclyl, heteroaryl or $C_{6-10}$aryl; or any two of $R^{5a}$, $R^{6a}$, $R^{5b}$ and $R^{6b}$ form together with the atom(s) to which they are attached a $C_{3-7}$cycloalkyl;

each $R^7$ is independently selected from the group consisting of halo, $C_{1-7}$alkyl, $C_{3-7}$cycloalkyl, $C_{1-7}$alkoxy, $C_{6-10}$aryloxy, heterocyclyl, $C_{6-10}$aryl, heteroaryl, CN and halo-$C_{1-7}$alkyl;

each $R^8$ is independently selected from the group consisting of halo, $C_{1-7}$alkyl, halo-$C_{1-7}$alkyl, $C_{1-7}$alkoxy, CN and halo-$C_{1-7}$alkoxy; or $R^2$ and $R^3$; $R^1$ and $R^2$; $R^1$ and $R^5$; $R^1$ and $R^{5a}$; $R^1$ and $R^{5b}$; $R^2$ and $R^{5a}$; $R^2$ and $R^{5b}$; or $R^2$ and $R^5$ can form with the atoms to which they are attached a 4- to 7-membered heterocyclyl; or $R^3$ and $R^5$; $R^3$ and $R^{5b}$ or $R^3$ and $R^{5a}$ can form together with the atoms to which they are attached a $C_{5-7}$cycloalkyl; and wherein each heteroaryl is a monocyclic aromatic ring comprising 5 or 6 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1 to 3 heteroatoms; and each heteroatoms being O, N or S;

p is 0, 1, 2, 3, 4 or 5, with the proviso that Ring C together with two adjacent $R^4$ groups do not form a 2-indole; and when Ring C is pyridine, thiazole, imidazole or pyrazole and two adjacent $R^4$ groups do not form with the atoms to which they are attached a phenyl or a 5- or 6-membered ring heteroaryl, than A is not a bond; and when Ring C together with two adjacent $R^4$ groups form oxazolo[4,5-b]pyiridine, than A is not a bond; and the compound of Formula I is not 2-methyl-N-(6-(5-(phenylsulfonamido)pyridin-3-yl)-1H-indazol-4-yl)thiazole-4-carboxamide, 2-chloro-N-isobutyl-N-((5-(3-(methylsulfonyl)phenyl)pyridin-3-yl)methyl)benzenesulfonamide or 4-(5-(4-chloro-2,5-dimethylphenylsulfonamido)pyridin-3-yl)benzoic acid.

In one embodiment, the invention pertains to compounds of Formula I or a pharmaceutically acceptable salt thereof, wherein A is a bond, —$CH_2$—, —$CHR^5$—, —$CR^5R^6$— or —$CR^{5a}R^{6a}$—$CR^{6b}R^{6b}$—;

Ring C is a phenyl;

$R^1$ is $C_{1-7}$alkyl, halo-$C_{1-7}$alkyl, $C_{3-7}$cycloalkyl, $C_{6-10}$aryl, $C_{6-10}$aryl-$C_{1-7}$alkyl, $C_{6-10}$aryloxy-$C_{1-7}$alkyl, heteroaryl or heterocyclyl in which alkyl, aryl, heteroaryl, heterocyclyl are optionally substituted with 1 to 5 $R^7$;

$R^2$ is H, $C_{1-7}$alkyl, halo-$C_{1-7}$alkyl, $C_{3-7}$cycloalkyl, heteroaryl, heterocycyl or $C_{6-10}$aryl;

$R^3$ is H, halo, $C_{1-7}$alkyl, halo-$C_{1-7}$alkyl, $C_{3-7}$cycloalkyl, cyano, $C_{1-7}$alkoxy, hydroxy, nitro, —$NH_2$, —$NH(C_{1-7}alkyl)$ or —$N(C_{1-7}alkyl)_2$;

each $R^4$ is independently selected from the group consisting of halo, $C_{1-7}$alkyl, halo-$C_{1-7}$alkyl, $C_{3-7}$cycloalkyl, cyano, —$NH_2$, —$NH(C_{1-7}alkyl)$, —$N(C_{1-7}alkyl)_2$, $C_{1-7}$alkoxy, halo-$C_{1-7}$alkoxy, hydroxy, carboxy, nitro, sulfonyl, sulfamoyl, sulfonamido, $C_{6-10}$aryl, heterocyclyl, $C_{6-10}$aryloxy, heterocyclyloxy, —SH, —S—$C_{1-7}$alkyl, —C(O)O-aryl, —C(O)O-heterocyclyl, —C(O)O-heteroaryl, —C(O)$NR^2$—$C_{1-7}$alkyl, —C(O)$NR^2$—$C_{6-10}$aryl, —C(O)$NR^2$-heteroaryl, —C(O)$NR^2$-heterocyclyl, —$NR^2$C(O)—$C_{1-7}$alkyl, —$NR^2$C(O)—$C_{6-10}$aryl, —$NR^2$C(O)-heteroaryl, —$NR^2$C(O)-heterocyclyl, —OC(O)—$C_{1-7}$alkyl, —OC(O)—$C_{6-10}$aryl, —OC(O)-heteroaryl and —OC(O)-heterocyclyl; wherein $R^4$ is optionally substituted with 1 to 5 $R^7$; or two adjacent $R^4$ groups can form with the atoms to which they are attached a phenyl or a 5- or 6-membered ring heteroaryl, in which said phenyl or heteroaryl ring is optionally substituted with 1 to 4 $R^8$;

$R^5$ and $R^6$ are independently $C_{1-7}$alkyl, $C_{3-7}$cycloalkyl, halo-$C_{1-7}$alkyl, heterocyclyl, heteroaryl or $C_{6-10}$aryl; or $R^5$ and $R^6$ form together with the atom to which they are attached a $C_{3-7}$cycloalkyl;

$R^{5a}$, $R^{6a}$, $R^{5b}$ and $R^{6b}$ are independently H, $C_{1-7}$alkyl, $C_{3-7}$cycloalkyl, halo-$C_{1-7}$alkyl, heterocyclyl, heteroaryl or $C_{6-10}$aryl; or any two of $R^{5a}$, $R^{6a}$, $R^{5b}$ and $R^{6b}$ form together with the atom(s) to which they are attached a $C_{3-7}$cycloalkyl;

each $R^7$ is independently selected from the group consisting of halo, $C_{1-77}$alkyl, $C_{3-7}$cycloalkyl, $C_{1-7}$alkoxy, $C_{6-10}$aryloxy, heterocyclyl, $C_{6-10}$aryl, heteroaryl, CN and halo-$C_{1-7}$alkyl;

each $R^8$ is independently selected from the group consisting of halo, $C_{1-7}$alkyl, halo-$C_{1-7}$alkyl, $C_{1-7}$alkoxy, CN and halo-$C_{1-7}$alkoxy;

p is 0, 1, 2, 3, 4 or 5; and the compound of Formula I is not 2-methyl-N-(6-(5-(phenylsulfonamido)pyridin-3-yl)-1H-indazol-4-yl)thiazole-4-carboxamide, 2-chloro-N-isobutyl-N-((5-(3-(methylsulfonyl)phenyl)pyridin-3-yl)methyl)benzenesulfonamide or 4-(5-(4-chloro-2,5-dimethylphenylsulfonamido)pyridin-3-yl)benzoic acid.

In another embodiment, certain compounds of Formula I include compounds of Formula II:

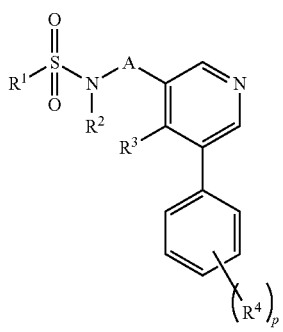

II or a pharmaceutically acceptable salt thereof, wherein
A is a bond, —$CH_2$—, —$CHR^5$— or —$CR^5R^6$—;

$R^1$ is $C_{1-7}$alkyl, halo-$C_{1-7}$alkyl, $C_{3-7}$cycloalkyl, $C_{6-10}$aryl, $C_{6-10}$aryl-$C_{1-7}$alkyl, $C_{6-10}$aryloxy-$C_{1-7}$alkyl, heteroaryl or heterocyclyl in which alkyl, aryl, heteroaryl, heterocyclyl are optionally substituted with 1 to 5 $R^7$;

$R^2$ is H, $C_{1-7}$alkyl, halo-$C_{1-7}$alkyl or $C_{3-7}$cycloalkyl;

each $R^4$ is independently selected from the group consisting of halo, $C_{1-7}$alkyl, halo-$C_{1-7}$alkyl, $C_{3-7}$cycloalkyl, cyano, —$NH_2$, —$NH(C_{1-7}$alkyl), —$N(C_{1-7}$alkyl$)_2$, $C_{1-7}$alkoxy, halo-$C_{1-7}$alkoxy, hydroxy, carboxy, nitro, sulfonyl, sulfamoyl, sulfonamido, $C_{6-10}$aryl, heterocyclyl, $C_{6-10}$aryloxy, heterocyclyloxy, —SH, —S—$C_{1-7}$alkyl, —C(O)O-aryl, —C(O)O-heterocyclyl, —C(O)O-heteroaryl, —C(O)$NR^2$—$C_{1-7}$alkyl, —C(O)$NR^2$—$C_{6-10}$aryl, —C(O)$NR^2$-heteroaryl, —C(O)$NR^2$-heterocyclyl, —$NR^2$C(O)—$C_{1-7}$alkyl, —$NR^2$C(O)—$C_{6-10}$aryl, —$NR^2$C(O)-heteroaryl, —$NR^2$C(O)-heterocyclyl, —OC(O)—$C_{1-7}$alkyl, —OC(O)—$C_{6-10}$aryl, —OC(O)-heteroaryl and —OC(O)-heterocyclyl; wherein $R^4$ is optionally substituted with 1 to 5 $R^7$;

$R^5$ and $R^6$ are independently $C_{1-7}$alkyl, $C_{3-7}$cycloalkyl, halo-$C_{1-7}$alkyl, heterocyclyl;

each $R^7$ is independently selected from the group consisting of halo, $C_{1-7}$alkyl, $C_{3-7}$cycloalkyl, $C_{1-7}$alkoxy, $C_{6-10}$aryloxy, heterocyclyl, $C_{6-10}$aryl, heteroaryl, CN and halo-$C_{1-7}$alkyl;

p is 0, 1, 2, 3, 4 or 5; and the compound of Formula II is not 2-chloro-N-isobutyl-N-((5-(3-(methylsulfonyl)phenyl)pyridin-3-yl)methyl)benzenesulfonamide or 4-(5-(4-chloro-2,5-dimethylphenylsulfonamido)pyridin-3-yl)benzoic acid.

Certain compounds of Formula I or I' include compounds of Formula III:

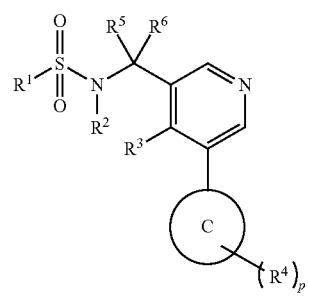

III or a pharmaceutically acceptable salt thereof, wherein Ring C, $R^1$, $R^2$, $R^3$, $R^4$, $R^5$, $R^6$ and p have the definitions of Formula I or Formula I', supra.

In one aspect of this embodiment, the invention pertains to compounds of Formula III wherein Ring C is phenyl. In another aspect of this embodiment, the invention pertains to compounds of Formula III wherein $R^1$ is alkyl (e.g. methyl, ethyl, propyl, isopropyl and the like) and $R^5$ is cycloalkyl (e.g. cyclopropyl, cyclobutyl, cyclopentyl and the like).

In one embodiment, the invention pertains to compounds of Formula I or I' wherein A is $CHR^5$, $R^1$ is alkyl (e.g. methyl, ethyl, propyl, isopropyl and the like) and $R^5$ is cycloalkyl (e.g. cyclopropyl, cyclobutyl, cyclopentyl and the like).

Certain compounds of Formula I or I' include compounds of Formula IV:

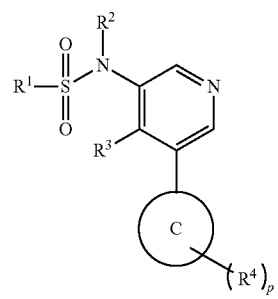

IV or a pharmaceutically acceptable salt thereof, wherein Ring C, $R^1$, $R^2$, $R^3$, $R^4$ and p have the definitions of Formula I or of Formula I', supra. In one aspect of this embodiment, the invention pertains to compounds of Formula IV wherein Ring C is phenyl. In another aspect of this embodiment, the invention pertains to compounds of Formula IV wherein $R^1$ is optionally substituted aryl or optionally substituted arylalkyl, wherein optional substituents are selected from $R^4$ groups. In yet another aspect of this embodiment, $R^1$ is optionally substituted phenyl or optionally substituted benzyl, wherein optional substituents are selected from $R^4$ groups. In yet another aspect of this embodiment, $R^2$ and $R^3$ form with the atoms to which they are attached a 4- to 7-membered heterocyclyl. In a non-limiting example, $R^2$ and $R^3$ form a piperidine.

Certain compounds of Formula I include compounds of Formula V:

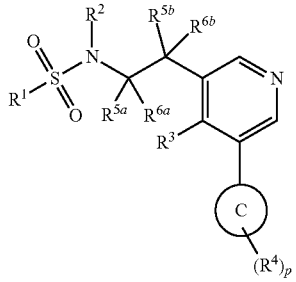

V or a pharmaceutically acceptable salt thereof, wherein Ring C, $R^1$, $R^2$, $R^3$, $R^4$, $R^{5a}$, $R^{6a}$ $R^{5b}$, $R^{6b}$ and p have the definitions of Formula I or of Formula I', supra. In one aspect of this embodiment, the invention pertains to compounds of Formula V wherein Ring C is phenyl.

In another aspect of this embodiment, the invention pertains to compounds of Formula V wherein $R^{5a}$, $R^{5b}$, $R^{6a}$ and $R^{6b}$ are H. In another aspect of this embodiment, the invention pertains to compounds of formula V wherein $R^{5a}$ and $R^{5b}$ form together with the atoms to which they are attached a $C_{3-7}$cycloalkyl. In a non-limiting example, $R^{5a}$ and $R^{5b}$ form a cyclopropyl. In another aspect of this embodiment, the invention pertains to compound of Formula V wherein $R^2$ and $R^{5b}$ form a 5- or 6-membered heterocyclyl. In a Representative example, $R^2$ and $R^{5b}$ form a piperidine or a pyrrolidine.

Certain compounds of Formula I or I' include compounds of Formula VI:

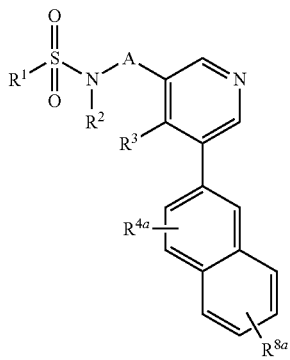

VI or a pharmaceutically acceptable salt thereof, wherein $R^1$, $R^2$, $R^3$, $R^4$, $R^8$, A and p have the definitions of Formula I or of Formula I', supra and $R^{4a}$ is $R^4$ or H, and $R^{8a}$ is $R^8$ or H. In one aspect of this embodiment, $R^8$ is halo, CN, alkoxy, unsubstituted $C_{1-4}$alkyl.

In another embodiment, the invention pertains to compounds of Formulae I, I', III, IV or V wherein Ring C is an optionally substituted 6-membered heteroaryl (e.g. pyridine, pyrimidine, pyrazine or pyridazine), wherein optional substituents are selected from $R^4$ groups.

In yet another embodiment, the invention pertains to compounds of Formula I, I', III, IV or V wherein Ring C is an optionally substituted 5-membered ring heteroaryl, the optional substituents being selected from $R^4$ groups. In a further aspect of this embodiment, Ring C is an isoxazole, oxazole, and pyrazole, each of which is optionally substituted with 1 to 5 $R^4$. In yet a further aspect, Ring C is a 5-membered ring heteroaryl, optionally substituted with 1 to 5 $R^4$ groups, and A is $CH_2$, $CHR^5$ or $CR^5R^6$.

In another embodiment, the invention pertains to compounds according to any one of Formulae I and III-VI wherein Ring C or Ring C together with 2 $R^4$ groups is selected from the followings:

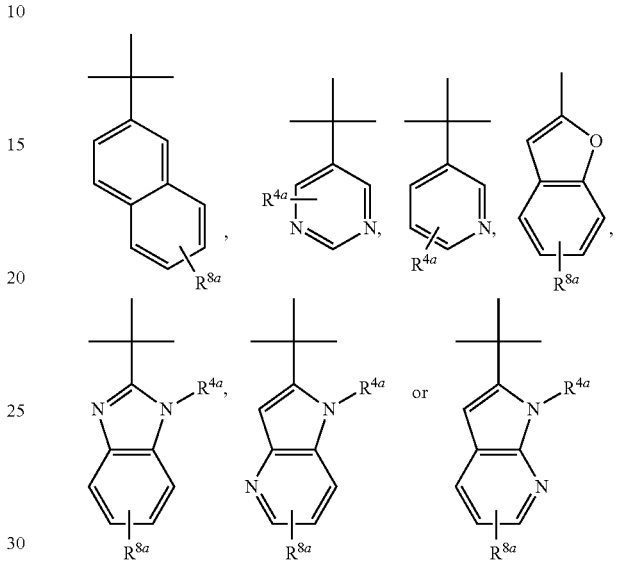

wherein $R^{4a}$ is $R^4$ or H, and $R^{8a}$ is $R^8$ or H.

In yet another embodiment, the invention pertains at least in part to compounds according to any one of Formulae I, I', II, III, IV and V, or a pharmaceutically acceptable salt thereof, wherein Ring C together with two adjacent $R^4$ groups can form benzofuran, benzothiazole, benzimidazole, benzoxazole, pyrrolopyridine (for example pyrrolo[2,3-b]pyridine, pyrrolo[2,3-c]pyridine, pyrrolo[3,2-c]pyridine and pyrrolo[3,2-b]pyridine), imidazopyridine (for example imidazo[4,5b]pyridine, imidazo[4,5-c]pyridine, imidazo[1,2-a]pyridine), indazole, or pyrazolopyridine (for example pyrazolo[1,5-a]pyridine). In a further aspect of this embodiment, Ring C together with two adjacent $R^4$ groups can form a benzimidazole or an azaindole.

In another embodiment, the invention pertains at least in part to compound according to any one of Formulae I, I', II, III, IV and V, or a pharmaceutically acceptable salt thereof, wherein two adjacent $R^4$ groups form with the atoms to which they are attached a 5- or 6-membered ring heteroaryl, in which said heteroaryl ring is optionally substituted with 1 to 4 $R^8$. In one aspect of this embodiment are compounds according to any one of Formulae I, I', II, III, IV and V, or a pharmaceutically acceptable salt thereof wherein $R^8$ is halo, CN, $C_{1-4}$alkoxy and unsubstituted $C_{1-4}$alkyl. In a representative example of this embodiment, Ring C is a phenyl and forms, together with two $R^4$ groups, an optionally substituted quinoline, benzofuran, benzothiophene, indole or benzothiazole, wherein optional substituents are selected from $R^8$ groups. In another aspect of this embodiment, Ring C is a 5-membered heteroaryl and two $R^4$ groups form an optionally substituted phenyl or a pyridine ring, which optional substituent is selected from $R^8$ groups.

One embodiment includes compounds according to any one of Formulae I to V or of any classes and subclasses described supra, wherein Ring C is phenyl.

The invention also pertains to the compounds of Formula VII:

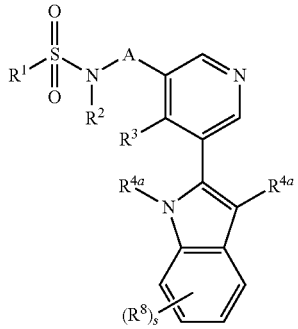

or a pharmaceutically acceptable salt thereof, wherein
A is —CHR⁵—, —CR⁵R⁶— or —CR⁵ᵃR⁶ᵃ—CR⁵ᵇR⁶ᵇ—;
$R^1$ is $C_{1-7}$alkyl, haloalkyl, $C_{3-7}$cycloalkyl, $C_{6-10}$aryl, $C_{6-10}$aryl-$C_{1-7}$alkyl, $C_{1-10}$aryloxy-$C_{1-7}$alkyl, heteroaryl or heterocyclyl in which alkyl, aryl, heteroaryl, heterocyclyl are optionally substituted with 1 to 5 $R^7$;
$R^2$ is H, $C_{1-7}$alkyl, halo-$C_{1-7}$alkyl, $C_{3-7}$cycloalkyl, heteroaryl, heterocycyl, or $C_{6-10}$aryl;
$R^3$ is H, halo, $C_{1-7}$alkyl, halo-$C_{1-7}$alkyl, $C_{3-7}$cycloalkyl, cyano, $C_{1-7}$alkoxy, hydroxy, nitro, —NH₂, —NH($C_{1-7}$alkyl) or —N($C_{1-7}$alkyl)₂;
$R^{4a}$ is H, halo, $C_{1-7}$alkyl, halo-$C_{1-7}$alkyl, $C_{3-7}$cycloalkyl, cyano, —NH₂, —NH($C_{1-7}$alkyl), —N($C_{1-7}$alkyl)₂, $C_{1-7}$alkoxy, halo-$C_{1-7}$alkoxy, hydroxy, carboxy, nitro, sulfonyl, sulfamoyl, sulfonamido, $C_{6-10}$aryl, heterocyclyl, $C_{6-10}$aryloxy, heterocyclyloxy, —SH, —S—$C_{1-7}$alkyl, —C(O)O—$C_{6-10}$aryl, —C(O)O-heterocyclyl, —C(O)O-heteroaryl, —C(O)NR²—$C_{1-7}$alkyl, —C(O)NR²—$C_{6-10}$aryl, —C(O)NR²-heteroaryl, —C(O)NR²-heterocyclyl, —NR²C(O)—$C_{1-7}$alkyl, —NR²C(O)—$C_{6-10}$aryl, —NR²C(O)-heteroaryl, —NR²C(O)-heterocyclyl, —OC(O)—$C_{1-7}$alkyl, —OC(O)—$C_{6-10}$aryl, —OC(O)-heteroaryl, —OC(O)-heterocyclyl; wherein $R^{4a}$ is optionally substituted with 1 to 5 $R^7$;
$R^5$ and $R^6$ are independently $C_{1-7}$alkyl, $C_{3-7}$cycloalkyl, halo-$C_{1-7}$alkyl, heterocyclyl, heteroaryl or $C_{6-10}$aryl; or $R^5$ and $R^6$ form together with the atom to which they are attached a $C_{3-7}$cycloalkyl;
$R^{5a}$, $R^{5b}$, $R^{6a}$ and $R^{6b}$ are independently $C_{1-7}$alkyl, $C_{3-7}$cycloalkyl, halo-$C_{1-7}$alkyl, heterocyclyl, heteroaryl or $C_{6-10}$aryl; or any two of $R^{5a}$, $R^{5b}$, $R^{6a}$, $R^{6b}$ form together with the atom(s) to which they are attached a $C_{3-7}$cycloalkyl;
each $R^7$ is independently selected from the group consisting of halo, $C_{1-7}$alkyl, $C_{3-7}$cycloalkyl, $C_{1-7}$alkoxy, $C_{6-10}$aryloxy, heterocyclyl, $C_{6-10}$aryl, heteroaryl, CN and halo-$C_{1-7}$alkyl;
each $R^8$ is independently selected from the group consisting of halo, $C_{1-7}$alkyl, halo-$C_{1-7}$alkyl, $C_{1-7}$alkoxy, CN and halo-$C_{1-7}$alkoxy; or
$R^2$ and $R^3$; $R^1$ and $R^2$; $R^1$ and $R^5$; $R^1$ and $R^{5a}$; $R^1$ and $R^{5b}$; $R^2$ and $R^{5a}$; $R^2$ and $R^{5b}$; or $R^2$ and $R^5$ can form with the atoms to which they are attached a 4- to 7-membered heterocyclyl; or $R^3$ and $R^5$; $R^3$ and $R^{5b}$; or $R^3$ and $R^{5a}$ can form together with the atoms to which they are attached a $C_{5-7}$cycloalkyl; and wherein each heteroaryl is a monocyclic aromatic ring comprising 5 or 6 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1 to 3 heteroatoms; and each heteroatoms being O, N or S;

s is 0, 1, 2, 3 or 4 and the compound of formula VIII is not Ethanesulfonic acid {1-[5-(6-chloro-3-cyano-1-methyl-1H-indol-2-yl)-pyiridin-3-yl]-ethyl}-amide.

Another embodiment includes compounds according to any one of Formulae I' and I to VII or of any classes and subclasses described supra, or a pharmaceutically acceptable salt thereof, wherein $R^1$ is $C_{1-4}$alkyl, halo $C_{1-4}$alkyl (e.g. $CH_2CF_3$, $CF_3$, $CHF_2$ and the like), optionally substituted aryl or optionally substituted arylalkyl, wherein optional substituents are selected from $R^4$ groups. In one aspect of this embodiment, $R^1$ is $C_{1-4}$alkyl (e.g. methyl or ethyl).

Another embodiment includes compounds according of any one of Formulae I' and I to VII or of any classes and subclasses described herein, or a pharmaceutically acceptable salt thereof, wherein $R^2$ is hydrogen, $C_{1-4}$alkyl (e.g., methyl, ethyl) or $C_{3-6}$cycloalkyl (e.g. cyclopropyl). In one particular aspect of this embodiment, $R^2$ is hydrogen.

Another embodiment include compounds according to any one of Formulae I' and I to VII or of any classes and subclasses described herein, or a pharmaceutically acceptable salt thereof, wherein $R^3$ is hydrogen.

Yet another embodiment include compound according to any one of Formulae I' and I to VI or of any classes and subclasses described herein, or a pharmaceutically acceptable salt thereof, wherein each $R^4$ is independently selected from the group consisting of halo, alkyl, haloalkyl, cycloalkyl, cyano, amido, amino, alkylamino, dialkylamino, alkoxy, haloalkoxy, hydroxy, carboxy, nitro, sulfonyl, sulfamoyl, sulfonamido, C(O)N($C_{1-4}$alkyl)₂, C(O)NR²—$C_{1-4}$alkyl, NR²C(O)—$C_{1-4}$alkyl and OC(O)—$C_{1-4}$alkyl. In one embodiment, $R^4$ is independently selected from the group consisting of halo, alkyl, haloalkyl, cycloalkyl, cyano, amido, amino, alkylamino, dialkylamino, alkoxy, haloalkoxy, hydroxy, nitro, C(O)N($C_{1-4}$alkyl)₂, C(O)NR²—$C_{1-4}$alkyl, NR²C(O)—$C_{1-4}$alkyl and OC(O)—$C_{1-4}$alkyl. In a further aspect of this embodiment, each $R^4$ is independently selected from $C_{1-4}$alkyl, $C_{1-4}$alkoxy (e.g. methoxy, ethoxy), CN, halo (e.g. chloro or fluoro), halo-$C_{1-4}$alkyl (e.g. $CF_3$, $CHF_2$, $CH_2CF_3$ and the like) or halo-$C_{1-7}$alkoxy (e.g. $OCF_3$).

Yet another embodiment includes compounds according to any one of Formulae I' and I to VII or of any classes and subclasses described herein, or a pharmaceutically acceptable salt thereof, wherein $R^5$ is H or $C_{1-4}$ alkyl (e.g., methyl, ethyl, propyl, isopropyl and butyl). In one particular aspect of this embodiment $R^5$ is methyl or isopropyl.

Another embodiment of interest includes compounds according to any one of Formulae I' and I to VII or of any classes and subclasses described herein; or a pharmaceutically acceptable salt thereof, wherein $R^5$ is $C_{3-6}$ cycloalkyl (e.g., cyclopropyl, cyclobutyl, cyclopentyl, and cyclohexyl).

In yet another embodiment, the invention pertains to compounds according to any one of Formulae I, I', II, VI and VII wherein A is $CH_2$, $CHR^5$ or $CR^5R^6$. In a further aspect of this embodiment, A is $CHR^5$. In yet a further aspect of this embodiment, the invention pertains to compounds according to any one of Formulae I, I', II, VI and VII, or a pharmaceutically acceptable salt thereof, wherein A is —CH($R^5$)— and the stereochemistry at the —$CHR^5$— chiral center is (S). In another embodiment, the invention pertains to compounds according to any one of Formulae I, I', II and V, or a pharmaceutically acceptable salt thereof wherein A is —$CHR^5$— and the stereochemistry at the —$CHR^5$— chiral center is (R).

In another embodiment, some compounds of the invention may have selectivity for aldosterone synthase (CYP11B2) relative to 11-beta hydroxylase (CYP11B1).

In one embodiment, the invention pertains to compounds according to any one of Formulae I, I', II and VI, or other classes and subclasses described supra, or a pharmaceutically acceptable salt thereof, wherein $R^1$ is $C_{1-4}$alkyl, $R^2$ is H, $R^3$ is H, A is $CHR^5$, $R^5$ is $C_{1-4}$alkyl or $C_{3-6}$cycloalkyl, p is 1 or 2; and each $R^4$ is $C_{1-4}$alkyl, halo-$C_{1-4}$alkyl (e.g. $CF_3$, $CHF_2$, $CH_2CF_3$ and the like), $C_{1-4}$alkoxy (e.g. methoxy, ethoxy), CN, halo or halo-$C_{1-4}$alkoxy (e.g. $OCF_3$).

In another embodiment $R^1$, $R^2$, $R^3$, $R^4$, $R^5$, $R^{5a}$, $R^{5b}$, $R^6$, $R^{6a}$, $R^{6b}$, $R^8$, A, and p groups are those defined by the $R^1$, $R^2$, $R^3$, $R^4$, $R^5$, $R^{5a}$, $R^{5b}$, $R^6$, $R^{6a}$, $R^{6b}$, $R^8$, A, and p groups, respectively, in Examples 1 to 87 in the Examples section below.

In another embodiment individual compounds according to the invention are those listed in Examples 1 to 87 in the Examples section below, or a pharmaceutically acceptable salt thereof.

Definition

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms. Representative examples of alkyl include methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-7}$alkyl" refers to a hydrocarbon having one to seven carbon atoms.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-7}$alkyl" refers to a hydrocarbon having one to seven carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons. The term "$C_{1-7}$alkoxy" refers to $C_{1-7}$alkyl-O—, wherein $C_{1-7}$alkyl is defined above.

The term alkoxyalkyl refers to an alkyl group, as defined above, in which the alkyl group is substituted with alkoxy The term "alkenyl" refers to a branched or unbranched hydrocarbon having at least one carbon-carbon double bond. The term "$C_{2-7}$alkenyl" refers to a hydrocarbon having two to seven carbon atoms and comprising at least one carbon-carbon double bond. Representative examples of alkenyl are vinyl, prop-1-enyl, allyl, butenyl, isopropenyl or isobutenyl.

The term "alkenyoxy" refer to alkenyl-O— wherein alkenyl has the definition above.

The term "alkynyl" refers to a branched or unbranched hydrocarbon having at least one carbon-carbon triple bond. The term "$C_{2-7}$-alkynyl" refers to a hydrocarbon having two to seven carbon atoms and comprising at least one carbon-carbon triple bond. Representative examples of alkynyl are ethynyl, prop-1-ynyl (propargyl), butynyl, isopropynyl or isobutynyl.

As used herein, the term "cycloalkyl" refers to saturated or partially unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-7}$ cycloakyl" refers to a cyclic hydrocarbon groups having 3 to 7 carbon atoms.

The term "cycloalkylalkyl" refers to an alkyl as defined above substituted with a cycloakyl as defined above.

The term "aryl" refers to monocyclic or bicyclic aromatic hydrocarbon groups having 6-10 carbon atoms in the ring portion. The term "aryl" also refers to a group in which an aromatic ring is fused to one or more cycloalkyl rings, where the radical or point of attachment is on the aromatic ring or on the fused cycloalkyl. Representative examples of aryl are phenyl, naphthyl, hexahydroindyl, indanyl or tetrahydronaphthyl. The term "$C_{6-10}$ aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-$CH_2CH_2$—.

The term "Heteroaryl" refers to aromatic monocyclic or bicyclic heteroaryl, containing from 5-10 ring members selected from carbon atoms and 1 to 5 heteroatoms, and each heteroatoms is independently selected from O, N or S, wherein S and N may be oxidized to various oxidation states. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl, pyrimidin-5-yl. The term "heteroaryl" also refers to a group in which a heteroaromatic ring is fused to one or more aryl, cycloaliphatic, or heterocyclyl rings, where the radical or point of attachment is on the heteroaromatic ring or on the fused aryl, cycloaliphatic or heterocyclyl rings. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5- d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

The term "heteroarylakyl" refers to alkyl substituted with heteroaryl.

As used herein, the term "heterocyclyl" or "heterocyclo" refers to a saturated or unsaturated non-aromatic ring (partially unsaturated) or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "heterocyclylalkyl" is an alkyl substituted with heterocyclyl. The term include substituted heterocyclylalkyl moiety.

The terms "alkoxyalkyl," include alkyl groups, as described above, in which the alkyl group is substituted with an alkoxy as defined above. The term includes substituted alkoxyalkyl moiety.

The term "hydroxyalkyl" refers to alkyl groups, as described above, in which the alkyl group is substituted with a hydroxy. The term includes substituted hydroxyalkyl moiety.

The term "sulfonyl" includes R—SO$_2$—, wherein R is hydrogen, alkyl, aryl, heteroaryl, aryl-alkyl, heteroaryl-alkyl, alkoxy, aryloxy, cycloalkyl, or heterocyclyl.

The term "sulfonamido" includes alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)-. The term includes substituted carbamoyl moieties The term "sulfamoyl" includes H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, (aryl-alkyl)-NHS(O)$_2$—, (heteroaryl-alkyl)-NHS(O)$_2$—. The term includes substituted sulfamoyl moieties.

The term "aryloxy" includes an —O-aryl, wherein aryl is defined herein. The term includes substituted aryloxy moieties.

The term "aryloxyalkyl" refers to alkyl group, as described above, in which the alkyl group is substituted with aryloxy. $C_{6-10}$aryloxy-$C_{1-7}$alkyl refers to a $C_{1-7}$alkyl group substituted with —O—$C_{6-10}$aryl. The term includes substituted aryloxyalkyl.

The term "heteroaryloxy" includes an —O-heteroaryl moiety, wherein heteroaryl is defined herein. The term includes substituted heteroaryloxy moieties.

The term heterocyclyloxy includes an —O-heterocyclyl, wherein heterocyclyl is defined herein. The term includes substituted heterocyclyloxy moieties.

The term "amine" or "amino" includes compounds where a nitrogen atom is covalently bonded to at least one carbon or heteroatom. The term "amine" or "amino" also includes —NH$_2$ and also includes substituted moieties. The term includes "alkyl amino" which comprises groups and compounds wherein the nitrogen is bound to at least one additional alkyl group. The term also includes "dialkyl amino" groups wherein the nitrogen atom is bound to at least two additional independently selected alkyl groups.

The term also includes "arylamino" and "diarylamino" groups wherein the nitrogen is bound to at least one or two independently selected aryl groups, respectively.

The term "ester" includes compounds and moieties which contain a carbon or a heteroatom bound to an oxygen atom which is bonded to the carbon of a carbonyl group.

The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings.

The term "heteroatom" includes atoms of any element other than carbon or hydrogen. Preferred heteroatoms are nitrogen, oxygen and sulfur.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1$H, $^2$H or D, $^3$H); any carbon represented by "C" in any of the formulae herein is intended to represent all isotopic forms of carbon (e.g. $^{11}$C, $^{13}$C, $^{14}$C); any nitrogen represented by "N" is intended to represent all isotopic forms of nitrogen (e.g. $^{14}$N, $^{15}$N). Other examples of isotopes that are included in the invention include isotopes of oxygen, sulfur, phosphorous, fluorine, iodine and chlorine, such as $^{18}$F $^{31}$P, $^{32}$P, $^{35}$S, $^{36}$Cl, $^{125}$I. The invention includes various isotopically labeled compounds as defined herein, for example those into which radioactive isotopes, such as $^3$H, $^{13}$C, and $^{14}$C are present. In one embodiment, the atoms in the formulae herein occur in their natural abundance. In another embodiment, one or more hydrogen atom may be enriched in $^2$H; or/and one or more carbon atom may be enriched in $^{11}$C, $^{13}$C or $^{14}$C; or/and one or more nitrogen may be enriched in $^{14}$N. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound according to any one of the formulae I' and I to VII. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Isotopically-enriched compounds according to any one of formulae I' and I to VII can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I or I' that contain groups capable of acting as donors and/or acceptors for hydrogen bonds may be capable of forming co-crystals with suitable co-crystal formers. These co-crystals may be prepared from compounds of formula I or I' by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula I or I'.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by aldosterone synthase and/or CYP11B1, or (ii) associated with aldosterone synthase and/or CYP11B1 activity, or (iii) characterized by abnormal activity of aldosterone synthase and/or CYP11B1; or (2) reduce or inhibit the activity of aldosterone synthase and/or CYP11B1; or (3) reduce or inhibit the expression of aldosterone synthase and/or CYP11B1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of aldosterone synthase and/or CYP11B1; or at least partially reducing or inhibiting the expression of aldosterone synthase and/or CYP11B1.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Aspects

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the process steps mentioned hereafter can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described herein.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The compounds of the invention can be synthesized using the methods described in the following schemes, examples, and by using art recognized techniques. All compounds described herein are included in the invention as compounds. Compounds of the invention, or a pharmaceutically acceptable salt thereof, may be synthesized according to at least one of the methods described in schemes 1 to 4, wherein variables $R^1$, $R^2$, $R^3$, $R^4$, $R^5$, $R^6$, A and p are as defined in Formula I or I' supra.

Scheme 1

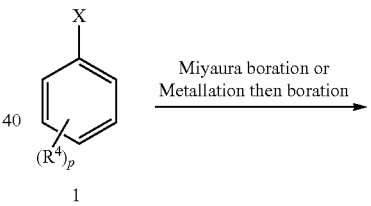

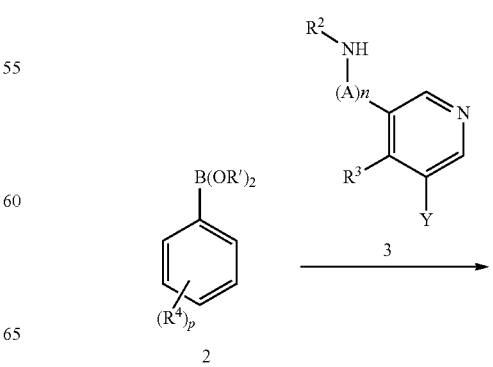

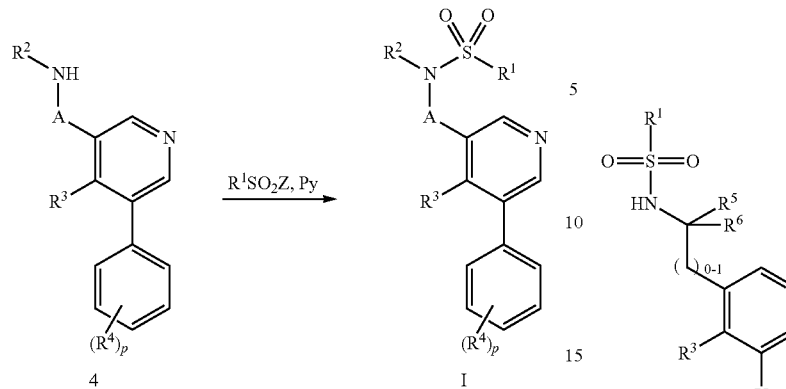

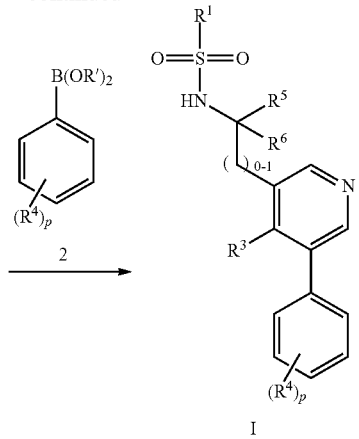

Scheme 2

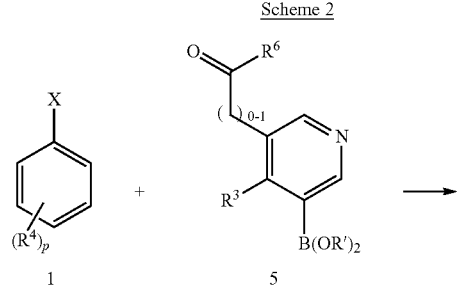

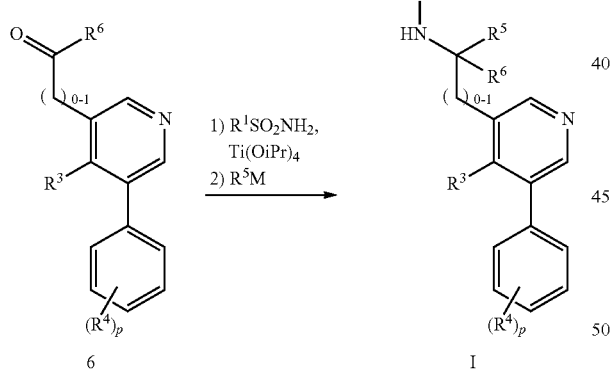

Scheme 3

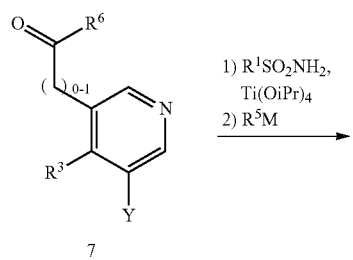

Generally, the compounds of formula (I) or (I') can be prepared according to scheme 1. Aryl halide (or triflate) 1 (X=Br, I, OTf) undergoes Miyaura boration or metallation (e.g. ortho-directed lithiation, halogen-metal exchange) followed by boration to the arylboronic ester (or acid) 2, which subsequently couples with pyridyl halide 3 (Y=Br, I or OTf) under typical Suzuki reaction condition to generate aryl-pyridyl amine 4. Sulfonylation of 4 with sulfonyl halide (Z=Cl, F, Br) in pyridine yields the corresponding aryl-pyridyl sulfonamide I. Compounds of Formula (I) or (I') wherein Ring C is heteroaryl can be prepared in a similar way by replacing aryl/phenyl boronic acid (or ester) 2 with heteroaryl boronic acid (or ester).

Alternatively, the compounds of formula (I) or (I'), (A is $CHR^5$ or $CHR^5CH_2$) can be synthesized according to scheme 2. Suzuki coupling of aryl halide 1 (X=Br, I, OTf) with pyridyl boronic ester (or acid) 5 (i.e in —B(OR')$_2$, R' is H or alkyl or 2 R' combine to form a heterocyclyl ring) yields aryl-pyridyl aldehyde 6, which is first treated with sulfonamide in the presence of Titanium (IV) alkoxide and subsequently reacts with nucleophiles (e.g. $R^5M$ is hydride, Grignard, organolithium, organozinc or other organometallic reagents) to generate I. Compounds of Formula (I) or (I')

wherein Ring C is heteroaryl can be prepared in a similar way by replacing aryl halide (phenyl halide) 1 with heteroaryl halide.

The synthesis of compounds of formula (I) or (I'), (n=1) can also be achieved by switching the order of Suzuki and nucleophilic addition according to scheme 3. Formylpyridyl halide 7 is treated with sulfonamide in the presence of Titanium (IV) alkoxide and subsequently reacts with nucleophiles (e.g. $R^5M$ is hydride, Grignard, organolithium, organozinc or other organometallic reagents) to generate 8, which undergoes Suzuki coupling with aryl boronic ester 2 and yields I. Compounds 7 are commercially available or can be easily obtained by reduction of the corresponding nitrile to the aldehyde using for example DIBAL (di-isobutyl aluminium hydride) or other reducing agents. Compounds of Formula (I) wherein Ring C is heteroaryl can be prepared in a similar way by replacing aryl/phenyl boronic acid (or ester) 2 with heteroaryl boronic acid (or ester).

Alternatively, 8 can be synthesized in the approach described in the scheme 4. Carboxylic acid or amide 9 (Z=O or NH) undergoes Curtius or Hofmann rearrangement to amine 10, which is subjected to sulfonylation with sulfonyl halide (Z=Cl, F, Br) in pyridine yields the corresponding aryl-pyridyl sulfonamide 8.

A compound of Formula I or I' or a salt thereof, wherein A is $CHR^5$ and the stereochemistry at the $CHR^5$ center is (R) is described in Scheme 5:

Scheme 5

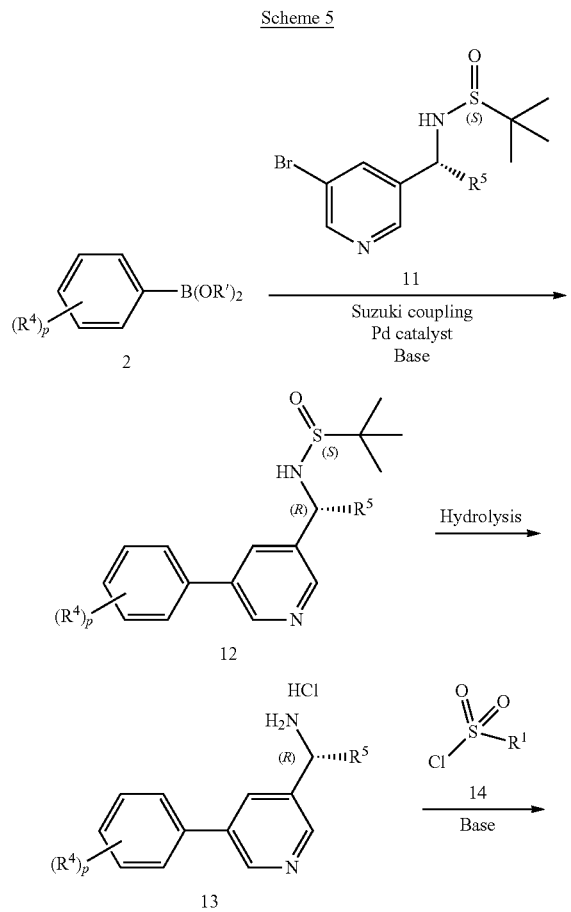

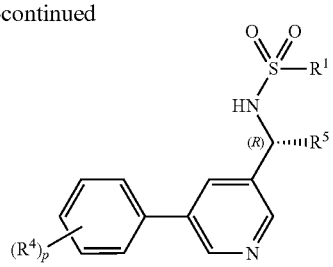

A compound of Formula 2 is converted into a compound of Formula I or I' or salt thereof, wherein A is $CHR^5$ and the stereochemistry at the $CHR^5$ center is (R) and wherein $R^4$, $R^5$, $R^1$ and p are as defined in Formula I or I', according to the method described in Scheme 5.

Aryl boronic ester or acid 2, wherein R' is H or alkyl or 2 R' combine to form and heterocyclyl ring such as 4,4,5,5-tetramethyl-[1,3,2]dioxaborolane, and wherein $R^4$ and p are defined in Formula I or I', undergoes Suzuki coupling with a chiral tert-butanesulfinamide 11 wherein $R^5$ is as described in Formula I or I', to generate sulfinamide 12 or a salt thereof.

The boronic acid or ester 2, can be prepared using Miyaura borylation procedure as described in Scheme 1. Preparation of boronic acid or ester is also described in Ishiyama, T.; Murata, N.; Miyaura, N. *J. Org. Chem.*, 1995, 60, 7508-7510. The Suzuki coupling reaction can be carried out using a palladium catalyst and a base. The Suzuki coupling reaction is well known in the art and is carried out using standard conditions. Examples of Suzuki coupling reactions are described in the exemplification section of the invention. For example, Suzuki reaction is described in Example 1 step 2, Example 34 step 2, example 35 step 2, Example 36 step 2, Example 37, example 38, example 40 and others. Examples of a palladium catalyst which can be used for the coupling are $PdCl_2(PPh_3)_2$, $PdCl_2(dppf).CH_2Cl_2$ or $Pd(PPh_3)_4$. Examples of a base which can be used for the coupling are $Na_2CO_3$, $K_2CO_3$, $K_3PO_4$. The Suzuki coupling reaction can be carried out in a solvent. Examples of a solvent are DME, DMF, $CH_2Cl_2$, ethanol, methanol, dioxane, water or toluene. One example of Suzuki coupling condition is $Pd(PPh_3)_4$ and $K_2CO_3$. Examples of solvent are water or DMF or a mixture thereof.

Intermediate 12 is then hydrolized to generate chiral amine 13 or salt thereof wherein $R^4$, $R^5$ and p are as defined in Formula I or I'. The hydrolysis can be carried out under acidic conditions. An example of hydrolysis is HCl hydrolysis. Hydrolysis of sulfinamide have been described in the literature (Ellman, J. A.; Owens, T. D.; Tang, T. P. *Acc. Chem. Res.* 2002, 35, 984; Robak, M. T.; Herbage, M. A.; Ellman, J. A. *Chem. Rev.* 2010, Apr. 26, DOI: 10, 1021/cr900382t).

Chiral amine 13 or salt thereof wherein $R^4$, $R^5$ and p are as defined in Formula I or I', is then reacted with a sulfonyl halide 14 wherein $R^1$ is as defined in Formula I or I', in the presence of a base, to generate a compound of Formula I or I' or a salt thereof, wherein A is $CHR^5$ and the stereochemistry at the $CHR^5$ center is (R). Example of a base is $K_2CO_3$ or pyridine. Optionally, the sulfonylation reaction can be facilitated using a catalyst. For example, a catalytic or a stoichiometric amount of DMAP (4-dimethylaminopyridine) can be used to accelerate the sulfonylation reaction. The sulfonylation reaction can be carried out in a solvent. Examples of a solvent are acetonitrile, methylene chloride or DMF. Alternatively, the base pyridine can serve as a solvent. Example of a reaction of an amine with a sulfonyl chloride is well known in the art. A detailed experimental procedure has also been described in Example 1 step 3 of the exemplification section. In one embodiment the base is K$_2$CO$_3$ and the solvent is acetonitrile. In a further aspect of this embodiment, DMAP is used to facilitate the reaction.

Scheme 6 described the synthesis of the chiral tert-butane-sulfinamide 11.

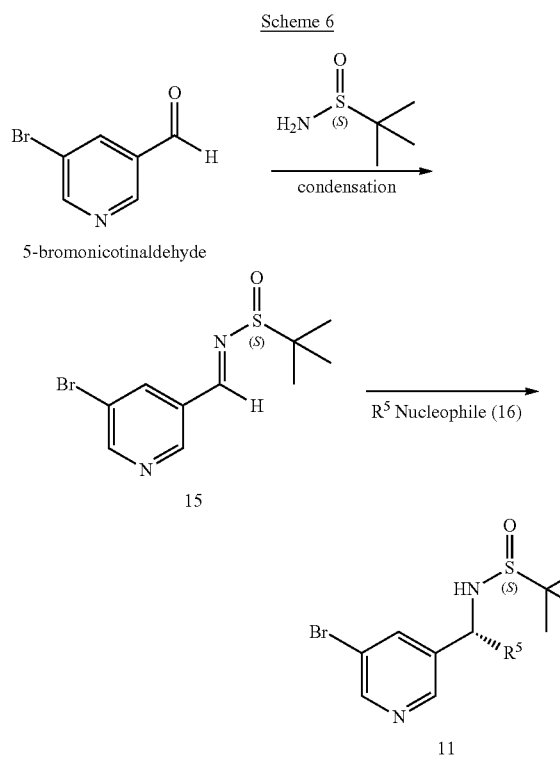

5-bromonicotinaldehyde is converted into sulfinamide compound 11 or salt thereof, wherein R$^5$ is as described in Formula I or I' as described in Scheme 6. 5-bromonicotinaldehyde is condensed with (S) enantiomer of 2-methylpropane-2-sulfinamide to generate tert-butanesulfinyl imine 15. The condensation can be carried out in the presence of a Lewis acid. Examples of Lewis acid are Ti(OEt)$_4$ or Ti(OiPr)$_4$. The preparation of tert-butanesulfinyl imine followed by addition of a nucleophile has been reported in the literature (Ellman, J. A.; Owens, T. D.; Tang, T. P. *Acc. Chem. Res.* 2002, 35, 984; Robak, M. T.; Herbage, M. A.; Ellman, J. A. *Chem. Rev.* 2010, Apr. 26, DOI: 10, 1021/cr900382t). In one embodiment, the condensation is carried out in the presence of Ti(OEt)$_4$.

Compound 15 or a salt thereof, is then converted to compound 11 or salt thereof, wherein R$^5$ is as described in Formula I or I' by addition of a nucleophile (16). Examples of a nucleophile are a Grignard reagent, organolithium reagent, organozinc reagent, organic aluminium reagent or enolate. An example of nucleophilic addition is described in Example 85 wherein the nucleophile is CF$_3$ anion derived from TMSCF$_3$.

In one specific embodiment, the nucleophile is a Grignard reagent (e.g. R$^5$MgBr, wherein R$^5$ is as defined in Formula I or I', or R$^5$ is methyl, ethyl, propyl, isopropyl, butyl, isobutyl, cyclopentyl, cyclobutyl or cyclopropyl).

The addition of the nucleophile 16 can be carried out using a solvent. Examples of a solvent are toluene, cumene, THF or CH$_2$Cl$_2$ or a mixture thereof; or a solvent known in the art for this transformation.

The addition of the nucleophile 16 is diastereoselective and generates the chiral tert-butane sulfinamide 11. The ratio of (S,R) versus (R,R) sulfinamide 11 varies depending on the nature of the solvent, the concentration, the temperature and on the nature of the nucleophile.

For example a diastereoselective addition of a Grignard reagent (R$^5$MgBr) can be achieved using a 0.3M solution of sulfinamide 15 in CH$_2$Cl$_2$, with a 2M solution of the magnesium bromide (R$^5$MgBr) in cumene with 1 equivalent of THF at a temperature ranging from −73 to −65 degrees celsius, to generate tert-butane sulfinamide 11 as the major diastereoisomer.

The corresponding (S) enantiomer of a compound of Formula I or I' or a salt thereof wherein A is CHR$^5$ and the stereochemistry at the CHR$^5$ chiral center is (S), could be synthesized in a similar manner condensing 5-bromonicotinaldehyde with the (R) enantiomer of 2-methylpropane-2-sulfinamide and following the synthetic steps described in Schemes 5 and 6.

Alternatively, the steps included in Scheme 5 can be carried out in different order. For example Schemes 7 and 8 described a few possible variations. Intermediate 11 or a salt thereof, wherein R$^5$ is as described in Formula I or I', can be hydrolyzed and reacted with a sulfonyl chloride prior to the Suzuki coupling reaction as described in Scheme 7.

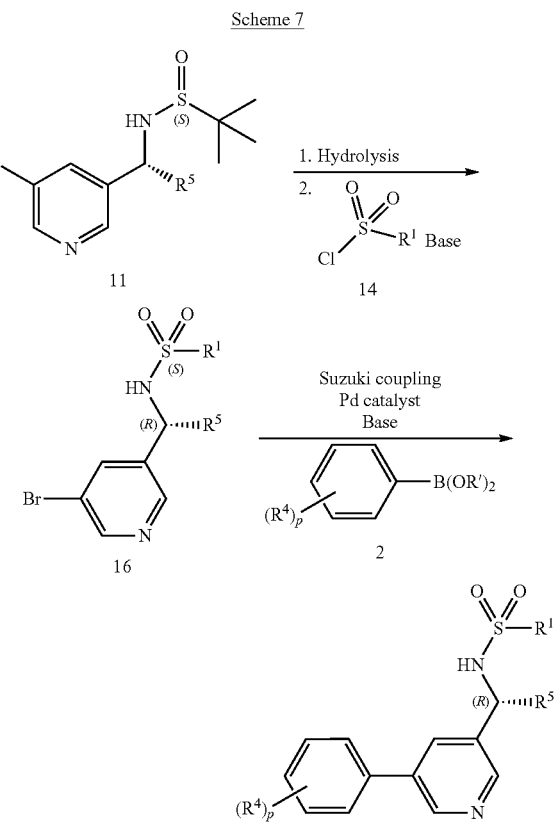

In Scheme 8, intermediate 11 is first hydrolyzed to the amine 17 or a salt thereof, wherein R$^5$ is as defined in Formula I or I'. The amine 17 undergoes Suzuki coupling to generate intermediate 18 or a salt thereof, wherein R$^4$, R$^5$ and p are as defined in Formula I or I'. Finally, the amine 18 or salt thereof, is reacted with sulfonyl chloride in the presence of a base, to generate a compound of Formula I or I' wherein A is CHR$^5$.

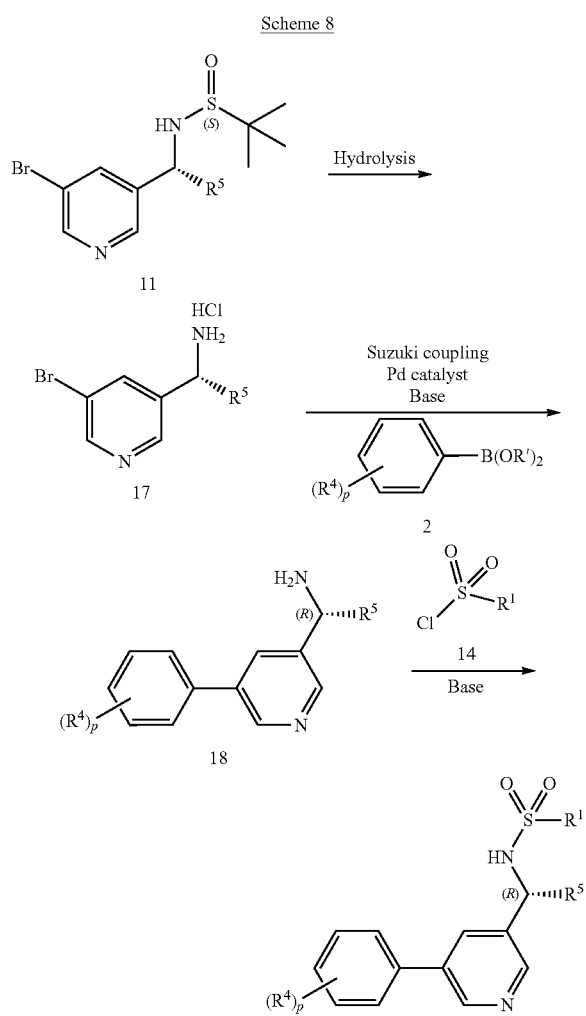

Scheme 8

Compound of Formula (I) or (I') wherein Ring C is heteroaryl can be prepared in a similar way, according to the previous schemes by replacing aryl halide (phenyl halide) 1 or boronic acid or ester 2 with the corresponding heteroaryl halide or heteroaryl boronic acid or ester respectively.

Compounds of the invention of Examples 25 to 39, 41 to 65, 78 to 83 and 85 can be synthesized according to Schemes 5 and 6, or alternatively 6 and 7 or 6 and 8 in addition to the synthetic procedures described herein.

The invention pertains to the process to convert compound of Formula 2 to a compound of Formula I or I' or salt thereof, wherein $R^5$, $R^4$ and p are as defined in Formula I or I', as outlined in Scheme 5 above, wherein compounds of Formula 11, 12 and 13 are as defined herein.

The invention also pertains to the process to convert 5-bromonicotinaldehyde to compound of Formula 11, or a salt thereof, wherein $R^5$ is as described herein in Formula I or I', as outlined in Scheme 6 above, wherein compounds of Formula 15 and 16 are as defined herein.

The invention also pertains to the process to convert compound of Formula 11 or a salt thereof, to a compound of Formula I or I' or salt thereof, wherein $R^5$, $R^4$ and p are as defined in Formula I or I', as outlined in Scheme 7 or 8 above, wherein compound of Formula 16, 17, 18 are as defined herein.

Intermediate process steps described in Schemes 5 to 7 are also embodiments of the present invention.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in pharmaceutically acceptable salt form, exhibit valuable pharmacological properties, e.g. aldosterone synthase and/or CYP11B1 modulating properties, e.g. as indicated in in vitro and in vivo tests as provided in the next sections and are therefore indicated for therapy.

Compounds of the invention may be useful in the treatment of an indication selected from: hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive Cortisol level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess. Thus, as a further embodiment, the present invention provides the use of a compound according to any one of formulae I' and I-VII, or a pharmaceutically acceptable salt thereof, in therapy. In a further embodiment, the therapy is selected from a disease which is ameliorated by inhibiton of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

In another embodiment, the invention provides a method of treating a disease which is ameliorated by inhibiton of aldosterone synthase and/or CYP11B1 comprising administration of a therapeutically acceptable amount of a compound according to any one of formulae I' and I-VII, or a pharmaceutically acceptable salt thereof. In a further embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

The pharmaceutical composition or combination of the present invention can be in unit dosage of about 0.01-500 mg of active ingredient(s) for a subject of about 50-70 kg, or about 0.01-250 mg or about 0.01-150 mg or about 0.01-100 mg, or about 0.01-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro tests. The compounds of the present invention can be applied in vitro in the form of solutions, e.g., preferably aqueous solutions. The dosage in vitro may range between about $10^{-3}$ molar and $10^{-9}$ molar concentrations. A therapeutically effective amount in vivo may range depending on the route of administration, between about 0.0001-500 mg/kg, or between about 0.0001-100 mg/kg, or between about 0.0003-10 mg/kg.

The activity of a compound according to the present invention can be assessed by the in vitro methods described below.

In particular, the aldosterone synthase inhibitory activities in vitro can be determined by the following assay.

Human adrenocortical carcinoma NCI-H295R cell line was obtained from American Type Culture Collection (Manassas, Va.). Insulin/transferrin/selenium (ITS)-A supplement (100×), DMEM/F-12, antibiotic/antimycotic (100×), and fetal bovine serum (FBS) were purchased from Invitrogen (Carlsbad, Calif.). Anti-mouse PVT scintillation proximity assay (SPA) beads and NBS 96-well plates were obtained from GE Health Sciences (Piscataway, N.J.) and Corning (Acton, Mass.), respectively. Solid black 96-well flat bottom plates were purchased from Costar (Corning, N.Y.). Aldosterone and angiotensin (Ang II) were purchased from Sigma (St. Louis, Mo.). D-[1,2,6,7-$^3$H(N)]aldosterone was acquired from PerkinElmer (Boston, Mass.). Nu-serum was a product of BD Biosciences (Franklin Lakes, N.J.).

For in vitro measurement of aldosterone activity, human adrenocortical carcinoma NCI-H295R cells are seeded in NBS 96-well plates at a density of 25,000 cells/well in 100 µL of a growth medium containing DMEM/F12 supplemented with 10% FCS, 2.5% Nu-serum, 1 µg ITS/ml, and 1× antibiotic/antimycotic. The medium is changed after culturing for 3 days at 37° C. under an atmosphere of 5% $CO_2$/95% air. On the following day, cells are rinsed with 100 µL of phosphate-buffered saline (PBS) and incubated with 100 µL of treatment medium containing 1 µM Ang II and a compound at different concentrations in quadruplicate wells at 37° C. for 24 h. At the end of incubation, 50 µL of medium is withdrawn from each well for measurement of aldosterone production by an SPA using mouse anti-aldosterone monoclonal antibodies.

Measurement of aldosterone activity can also be performed using a 96-well plate format. Each test sample is incubated with 0.02 µCi of D-[1,2,6,7-$^3$H(N)]aldosterone and 0.3 µg of anti-aldosterone antibody in PBS containing 0.1% Triton X-100, 0.1% bovine serum albumin, and 12% glycerol in a total volume of 200 µL at room temperature for 1 h. Anti-mouse PVT SPA beads (50 µL) are then added to each well and incubated overnight at room temperature prior to counting in a Microbeta plate counter. The amount of aldosterone in each sample is calculated by comparing with a standard curve generated using known quantities of the hormone.

The in vitro inhibitory activities for CYP11B1 can be determined by the following assay.

The cell line NCI-H295R was originally isolated from an adrenocortical carcinoma and has been characterized in the literature through the stimulable secretion of steroid hormones and the presence of the enzymes essential for steroidogenesis. Thus, the NCI-H295R cells have CYP11B1 (steroid 11 β-hydroxylase). The cells show the physiological property of zonally undifferentiated human fetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbeoco's Modified Eagle'Ham F-12 Medium (DME/F12), which has been supplemented with Ulroser SF Serum (Soprachem, Cergy-Saint-Christophe, France), insulin, transferrin, selenite (I-T-S, Becton Dickinson Biosiences, Franklin lakes, N.J., USA) and antibiotics in 75 $cm^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin II (1D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturer's instructions.

Inhibition of the release of certain steroids can be used as a measure of the respective enzyme inhibition by the added test compounds. The dose-dependent inhibition of enzymatic activity by a compound is calculated by means of an inhibition plot which is characterized by an $IC_{50}$.

The $IC_{50}$ values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: $Y=(d-a)/((1+(x/c)b))+a$, where: a=minimum data level, b=gradient, I c=ICED, d=maximum data level, x=inhibitor concentration.

The inhibition activity of aldosterone production can also be expressed in percentage inhibition (% inhibition) at a given concentration (e.g. % inhibition at 1 µM), which is the aldosterone level when the cell is treated with the given concentration of a compound of this invention (e.g. concentration of 1 µM) versus the aldosterone excretion when cell is free of the compound of the invention:

$$\% \text{ inhibition aldosterone production} = [(Y-X)/Y] \times 100$$

wherein X is the level of aldosterone when the cell is treated with a compound of Formula I; and Y is the level of aldosterone when the cell is free of compound of Formula I.

The inhibition activity of CYP11B1 production can also be expressed in percentage inhibition (% inhibition) at a given concentration (e.g. % inhibition at 1 µM), which is the cortisol level when cell is treated with the given concentration of a compound of the invention (e.g. concentration of 1 μM) versus the cortisol excretion when cell is free of the compound of the invention.

% inhibition cortisol production=[(Y'−X')/Y']×100 wherein X' is the level of cortisol when the cell is treated with a compound of Formula I; and Y' is the level of cortisol when the cell is free of compound of Formula I.

Using the test assays (as described above) compounds of the invention exhibit inhibitory efficacy as shown in Table 1, provided infra.

TABLE 1

Inhibitory Activity of Compounds:

| Compound | Aldosterone cell secretion (IC$_{50}$ nM) | Cortisol cell secretion (% inhibition @ 1 μM) |
|---|---|---|
| N-[5-(3-Chloro-4-cyano-phenyl)-pyridin-3-yl]-4-methoxy-benzene-sulfonamide | 9 | 74.5 |
| N-(5-(3-chloro-4-cyanophenyl)pyridin-3-yl)-1-(2-chlorophenyl)methanesulfonamide | 45 | 34 |
| N-(5-(4-cyano-3-methoxyphenyl)pyridin-3-yl)cyclopropane-sulfonamide | 77 | 32 |
| N-(5-(4-cyano-3-methoxyphenyl)pyridin-3-yl)ethanesulfonamide | 33 | 38 |
| N-[5-(3-Chloro-4-cyano-phenyl)-pyridin-3-yl]-4-ethyl-benzene-sulfonamide | 6 | 78 |
| N-((5-(4-cyano-3-methoxyphenyl)pyridin-3-yl)methyl)methane-sulfonamide | 85 | 40 |
| N-(1-(5-(4-cyano-3-methoxyphenyl)pyridin-3-yl)ethyl)ethanesulfonamide: | | |
| Enantiomer 1 | 64 | 38 |
| Enantiomer 2 | 140 | 27 |
| N-(1-(5-(3-chloro-4-cyanophenyl)pyridin-3-yl)ethyl)ethanesulfonamide: | | |
| Enantiomer 1 | 49 | 53 |
| Enantiomer 2 | 74 | 50 |
| N-(1-(5-(3-chloro-4-cyanophenyl)pyridin-3-yl)butyl)ethanesulfonamide: | | |
| Racemate | 132 | 25 |
| Enantiomer 1 | 89 | 26 |
| Ethanesulfonic acid [5-(6-chloro-1-methyl-1H-pyrrolo[3,2-c]pyridin-2-yl)-pyridin-3-ylmethyl]-amide | 165 | 15 |
| N-((5-(4-cyano-3-methoxyphenyl)pyridin-3-yl)(cyclopropyl)methyl)ethanesulfonamide: | | |
| Enantiomer 1 | 111 | 25 |
| Enantiomer 2 | 41 | 44 |
| (S)-N-((5-(3-chloro-4-cyanophenyl)pyridin-3-yl)(cyclopropyl)methyl)ethanesulfonamide: | 24 | 38 |
| (R)-N-((5-(3-chloro-4-cyanophenyl)pyridin-3-yl)(cyclopropyl)methyl)ethanesulfonamide: | 56 | 29 |
| N-((5-(3-chloro-4-cyanophenyl)pyridin-3-yl)(cyclopropyl)methyl)-N-methylethanesulfonamide | 5 | 63 |

TABLE 1-continued

Inhibitory Activity of Compounds:

| Compound | Aldosterone cell secretion (IC$_{50}$ nM) | Cortisol cell secretion (% inhibition @ 1 μM) |
|---|---|---|
| N-((5-(6-chloro-1-methyl-1H-benzo[d]imidazol-2-yl)pyridin-3-yl)methyl)ethanesulfonamide | 97 | 24 |
| Ethanesulfonic acid [5-(6-chloro-1-methyl-1H-pyrrolo[2,3-b]pyridin-2-yl)-pyridin-3-ylmethyl]-amide | 8 | 40 |
| N-((5-(4-cyano-2-fluorophenyl)pyridin-3-yl)(cyclopropyl)methyl)ethanesulfonamide | 167 | 39 |
| N-((5-(4-chlorophenyl)pyridin-3-yl)(cyclopropyl)methyl)-ethanesulfonamide | 42 | 31 |
| N-(cyclopropyl(5-(4-(trifluoromethoxy)phenyl)pyridin-3-yl)methyl)ethanesulfonamide | 110 | 20 |
| N-((5-(3-chloro-4-fluorophenyl)pyridin-3-yl)(cyclopropyl)methyl)-ethanesulfonamide | 22 | 21 |
| N-(cyclopropyl(5-(2,3-dichlorophenyl)pyridin-3-yl)methyl)ethanesulfonamide | 5 | 39 |
| 2-chloro-4-[5-(1,1-dioxo-isothiazolidin-2-ylmethyl)-pyridin-3-yl]-benzonitrile | 12 | 64 |
| ethanesulfonic acid {[5-(3-chloro-4-cyano-phenyl)-pyridin-3-yl]-cyclopropyl-methyl}-(2-hydroxy-ethyl)-amide | 20 | 51 |
| Ethanesulfonic acid {[5-(3-chloro-4-cyano-phenyl)-pyridin-3-yl]-cyclopropyl-methyl}-isobutyl-amide | 98 | 35 |
| N-(2-(5-(3-chloro-4-cyanophenyl)pyridin-3-yl)propan-2-yl)ethanesulfonamide | 99 | 66 |
| N-((5-(4-cyano-3-methylphenyl)pyridin-3-yl)(4-fluorophenyl)methyl)ethane-sulfonamide | 121 | 23 |
| N-(2-(5-(2,3-dichlorophenyl)pyridin-3-yl)cyclopropyl)ethane-sulfonamide | 3 | 75 |

The compound of the present invention may be administered either simultaneously with, or before or after, at least one other therapeutic agent. The compound of the present invention may be administered separately, by the same or different route of administration, or together in the same pharmaceutical composition.

In one embodiment, the invention provides a product comprising a compound according to any one of formulae I' and I-VII, or a pharmaceutically acceptable salt thereof, and at least one other therapeutic agent as a combined preparation for simultaneous, separate or sequential use in therapy. In one embodiment, the therapy is the treatment of a disease or condition mediated by aldosterone synthase and/or CYP11BI. Products provided as a combined preparation include a composition comprising the compound according to any one of formulae I' and I to VI, or a pharmaceutically acceptable salt thereof, and the other therapeutic agent(s) together in the same pharmaceutical composition, or the compound of formulae I to VI and the other therapeutic agent(s) in separate form, e.g. in the form of a kit.

In one embodiment, the invention provides a pharmaceutical composition comprising a compound according to any one of formulae I' and I-VII, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formulae I-VII. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formulae I-VII in the manufacture of a medicament for treating a disease or condition mediated by aldosterone synthase and/or CYP11B1, wherein the medicament is prepared for administration with another therapeutic agent. The invention also provides the use of a another therapeutic agent in the manufacture of medicament for treating a disease or condition mediated by aldosterone synthase and/or CYP11B1, wherein the medicament is prepared for administration with a compound of formulae I-VII.

The invention also provides a compound according to any one of formulae I' and I-VII, or a pharmaceutically acceptable salt thereof, for use in a method of treating a disease or condition mediated by aldosterone synthase and/or CYP11B1, wherein the compound of formulae I' or I-VII is prepared for administration with another therapeutic agent. The invention also provides another therapeutic agent for use in a method of treating a disease or condition mediated by aldosterone synthase and/or CYP11B1, wherein the other therapeutic agent is prepared for administration with a compound according to any one of formulae I' and I-VII. The invention also provides a compound according to any one of formulae I' and I-VII, or a pharmaceutically acceptable salt thereof, for use in a method of treating a disease or condition mediated by aldosterone synthase and/or CYP11B1, wherein the compound of formulae I' or I-VII is administered with another therapeutic agent. The invention also provides another therapeutic agent for use in a method of treating a disease or condition mediated by aldosterone synthase and/or CYP11B1, wherein the other therapeutic agent is administered with a compound according to any one of formulae I' and I-VII.

The invention also provides the use of a compound according to any one of formulae I' and I-VII, or a pharmaceutically acceptable salt thereof, in the manufacture of a medicament for treating a disease or condition mediated by aldosterone synthase and/or CYP11B1, wherein the patient has previously (e.g. within 24 hours) been treated with another therapeutic agent. The invention also provides the use of another therapeutic agent in the manufacture of a medicament for treating a disease or condition mediated by aldosterone synthase and/or CYP11B1, wherein the patient has previously (e.g. within 24 hours) been treated with a compound according to any one of formulae I' and I-VII.

In one embodiment, the other therapeutic agent is selected from: HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

In still another embodiment, the invention pertains, at least in part, to methods wherein the compound of the invention (e.g., a compound according to any one of Formulae I' and I-VII or a compound otherwise described herein, or a pharmaceutically acceptable salt thereof) is administered in combination with a second agent.

The term "in combination with" a second agent or treatment includes co-administration of the compound of the invention (e.g., a compound according to any one of Formulae I' and I-VII or a compound otherwise described herein, or a pharmaceutically acceptable salt thereof) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g., an aldosterone synthase associated disorder, such as, for example, hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries. Furthermore, the second agent may be any agent of benefit to the patient when administered in combination with the administration of a compound of the invention.

Examples of second agents include HMG-Co-A reductase inhibitors, angiotensin II receptor antagonists, angiotensin converting enzyme (ACE) Inhibitors, calcium channel blockers (CCB), dual angiotensin converting enzyme/neutral endopeptidase (ACE/NEP) inhibitors, endothelin antagonists, renin inhibitors, diuretics, ApoA-I mimics, anti-diabetic agents, obesity-reducing agents, aldosterone receptor blockers, endothelin receptor blockers, and CETP inhibitors.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the AT₁ receptor, these antagonists can, for example, be employed as antihypertensives or for treating congestive heart failure.

The class of AT₁ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

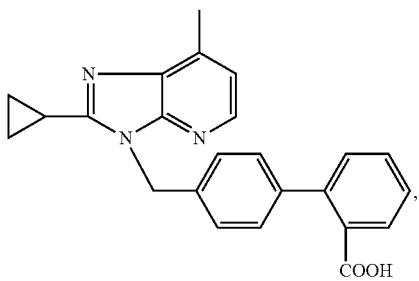 [SMILES: Cc1ccnc2c1nc(C1CC1)n2Cc1ccc(-c2ccccc2C(=O)O)cc1]

the compound with the designation SC-52458 of the following formula

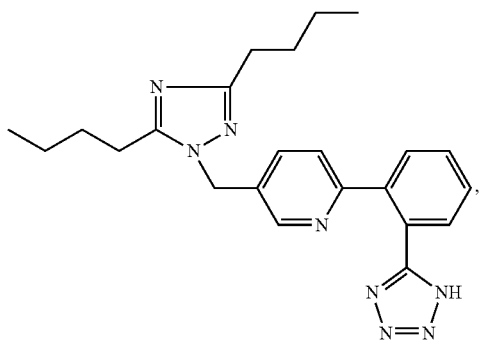 [SMILES: CCCCc1nc(CCCC)n(Cc2ccc(-c3ccccc3-c3nnn[nH]3)nc2)n1]

and the compound with the designation ZD-8731 of the following formula

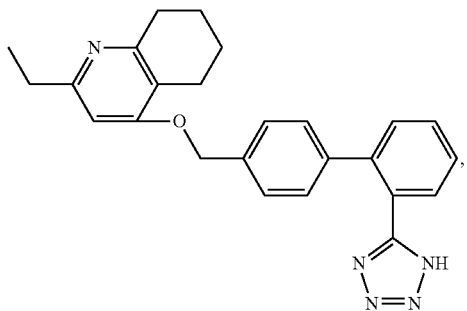 [SMILES: CCc1cc(OCc2ccc(-c3ccccc3-c3nnn[nH]3)cc2)c2c(n1)CCCC2]

or, in each case, a pharmaceutically acceptable salt thereof.

Preferred AT-receptor antagonist are those agents which have been marketed, most preferred is valsartan or a pharmaceutically acceptable salt thereof.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "dual angiotensin converting enzyme/neutral endopetidase (ACE/NEP) inhibitor" includes omapatrilate (cf. EP 629627), fasidotril or fasidotrilate, or pharmaceutically acceptable salts thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly 1-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methyl hexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

(A)

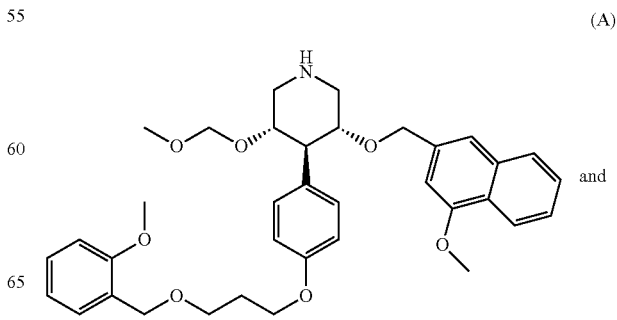

and

-continued (B)

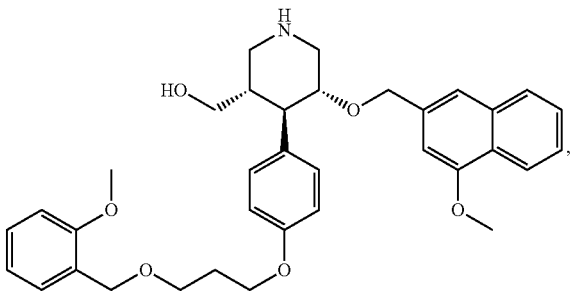

pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzenesulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine](cf. EP 196222 and EP 526171) of the formula

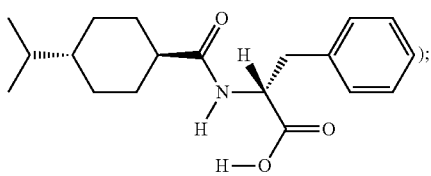 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid](cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in Diabetologia, 28, 1985, 704-707 and in U.S. Pat. No. 5,705,483.

The term "GLP-1 agonists" includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl] methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signaling pathway modulators, like inhibitors of protein tyrosine phosphatases (PTPases), antidiabetic non-small molecule mimetic compounds and inhibitors of g lutamine-fructose-6-phosphate amidotransferase (GFAT); compounds influencing a dysregulated hepatic glucose production, like inhibitors of glucose-6-phosphatase (G6 Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RX R) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α₂-adrenergic antagonists; and pharmaceutically acceptable salts thereof.

The term "obesity-reducing agent" includes lipase inhibitors (e.g., orlistat) and appetite suppressants (e.g., sibutramine and phentermine).

The term "aldosterone receptor blocker" includes spironolactone and eplerenone.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.;* 6:1951-1954 (1996), respectively. Furthermore, the CETP inhibitors also include those disclosed in WO2000/017165, WO2005/095409 and WO2005/097806.

EXEMPLIFICATION OF THE INVENTION

Common Abbreviations app apparent
ACN acetonitrile
BINAP racemic 2,2'-bis(diphenylphosphino)-1,1'-binaphthyl
BOC tertiary butyl carboxy
br broad
BSA bovine serum albumin
cPr cyclopropyl
d doublet
dd doublet of doublets
DCM dichloromethane
DIEA diethylisopropylamine
DIPA diisopropylamine
DME 1,4-dimethoxyethane
DMF N,N-dimethylformamide
DMSO dimethylsulfoxide
EtOAc ethyl acetate
ESI electrospray ionization
EtOAc ethyl acetate
h hour(s)
HPLC high pressure liquid chromatography
HRMS: high resolution mass spectrometry
IR infrared spectroscopy
IPA iso-propyl alcohol
KOTMS potassium trimethylsilanolate
LCMS liquid chromatography and mass spectrometry
MeOH methanol
MS mass spectrometry
MW microwave
m multiplet
min minutes
mL milliliter(s)
m/z mass to charge ratio
NMR nuclear magnetic resonance
ppm parts per million
rac racemic
rt room temperature
s singlet
PdCl₂(dppf).CH₂Cl₂ dichloro[1,1'-ferrocenylbis(diphenylphosphine)]palladium(II) dichloromethane
PdCl₂(PPh₃)₂ bis(triphenylphosphine)palladium(II) chloride
Pd₂(dba)₃ tris(dibenzylideneacetone)dipalladium(0)
s-PHOS 2-dicyclohexylphosphino-2',6'-dimethoxybiphenyl
Pd(PPh₃)₄ tetrakis(triphenylphosphine)palladium(0)
t triplet
TEA triethylamine
TFA trifluoroacetic acid
THF tetrahydrofuran
TLC thin layer chromatography
RT room temperature
SFC supercritical fluid chromatography The following examples are intended to illustrate the invention and are not to be construed as being limitations thereon. Temperatures are given in degrees centrigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR.

Abbreviations used are those conventional in the art. All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

EXAMPLES

Example 1

N-(5-(3-chloro-4-cyanophenyl)pyridin-3-yl)ethanesulfonamide

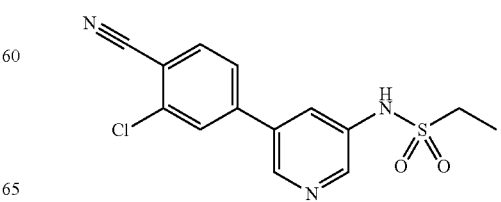

Step 1: synthesis of 2-chloro-4-(4,4,5,5-tetramethyl-1,3,2-dioxaborolan-2-yl)benzonitrile

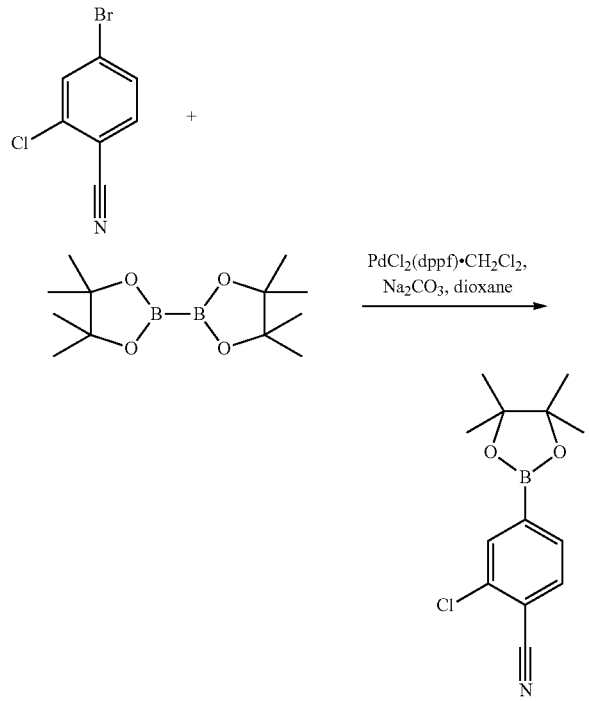

A mixture of 4-bromo-2-chlorobenzonitrile (15 g, 69.3 mmol), 4,4,4',4',5,5,5',5'-octamethyl-2,2'-bi(1,3,2-dioxaborolane) (17.60 g, 69.3 mmol), potassium acetate (13.60 g, 139 mmol) and PdCl$_2$(dppf).CH$_2$Cl$_2$ adduct (2.83 g, 3.46 mmol) in 1,4-dioxane (100 mL) was heated to 80° C. for 4.5 h. After filtration and concentration, the residue was dissolved into CH$_2$Cl$_2$ and mixed with celite. After concentration, the residue was loaded to column (120 g isco) and flushed with ethyl acetate/heptane (v/v, 0%-5%) and resulted in a colorless solid 16.4 g. $^1$H NMR (400 MHz, CDCl$_3$): δ 1.35 (s, 12H), 7.61 (d, J=7.6 Hz, 1H), 7.70 (d, J=7.6 Hz, 1H), 7.87 (s, 1H).

Step 2: Synthesis of 4-(5-Amino-pyridin-3-yl)-2-chloro-benzonitrile

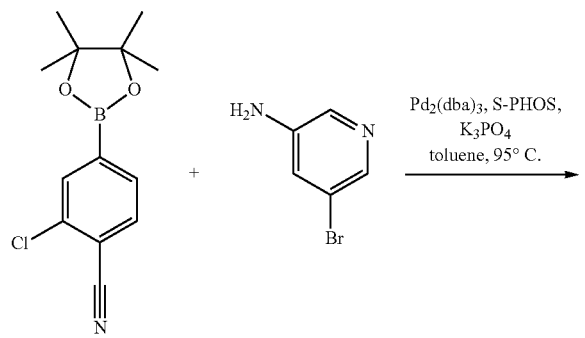

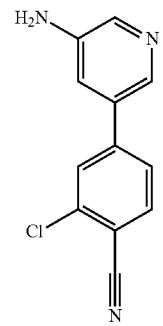

(General Suzuki reaction procedure 1) A mixture of 2-chloro-4-(4,4,5,5-tetramethyl-1,3,2-dioxaborolan-2-yl)benzonitrile (1.32 g, 5 mmol), 5-Bromo-pyridin-3-ylamine (865 mg, 5 mmol), s-PHOS (103 mg, 0.25 mmol), potassium phosphate (2.12 g, 10 mmol) and Pd$_2$(dba)$_3$ (41.2 mg, 0.1 mmol) in toluene (20 mL) was heated to 95° C. overnight (18 h). After filtration and concentration, the residue was dissolved into CH$_2$Cl$_2$ and mixed with celite. After concentration, the residue was loaded to column (MeOH—CH$_2$C2, v/v, 1%-3.5%) and resulted in a light brown solid (500 mg). $^1$HNMR (400 MHz, CDCl$_3$): δ 4.82 (brs, 2H), 7.11 (t, J=2 Hz, 1H), 7.55 (dd, J=2 Hz, 8 Hz, 1H), 7.69 (d, J=2 Hz, 1H), 7.75 (d, J=8 Hz, 1H), 8.16 (d, J=2 Hz, 1H), 8.22 (d, J=2 Hz, 1H).

Step 3: Synthesis of N-(5-(3-chloro-4-cyanophenyl)pyridin-3-yl)ethanesulfonamide (General sulfonylation procedure 1) Ethylsulfonyl chloride (77 mg, 0.6 mmol, 4 eq.) was added dropwise to a solution of 4-(5-amino-pyridin-3-yl)-2-chloro-benzonitrile (34.5 mg, 0.15 mmol, 1 eq) in anhydrous pyridine (1 mL) at 0° C. The mixture was stirred at room temperature overnight. The reaction mixture was concentrated and the residue was purified by flash column (dichloromethane/methanol, v/v, 1%-10%) and yielded a colorless product. ESI-MS m/z: 322.0 [M+H]$^+$, $^1$H NMR (400 MHz, CDCl$_3$) δ ppm 1.59 (t, J=7.3 Hz, 3H), 3.33-3.34 (m, 2H), 7.72 (d, 1H), 7.78 (s, 1H), 7.79 (d, 1H), 8.00 (s, 1H), 8.60 (s, 1H), 8.88 (s, 1H).

The following compounds were synthesized in similar manner:

(General Sulfonylation Procedure 2): To a solution of 4-(5-amino-pyridin-3-yl)-2-chloro-benzonitrile (20 mg, 87 μmol, 1 eq) in anhydrous pyridine (500 μl) was added a sulfonyl chloride derivative (1.1 eq). The mixture was stirred at room temperature overnight. Upon analysis by analytical LC-MS of an aliquot of the reaction mixture showing the completion of the reaction, the reaction mixture was diluted with ethyl acetate and the resulting solution was washed with saturated aqueous NaHCO$_3$. The aqueous phase (basic pH) was back extracted with ethyl acetate. The combined organic phase was dried over Na$_2$SO$_4$ and filtered. The filtrate obtained was concentrated in vacuo to give a crude material which was purified either:

- by ISCO flash chromatography system on silica gel column, eluting with mixtures of dichloromethane/methanol.
- by preparative TLC, eluting with dichloromethane/methanol 95/5.
- or by precipitation in methanol and filtration.

The isolated product was lyophilized and identified by LC-MS and NMR.

Analytical LC-MS (system 1): Waters Acquity UPLC, Run Time: 6.00 min, Acquity Column 2.1×50 mm HSS T3 1.8μ. Solvent A: Water+3 mM ammonium acetate+0.05% formic acid (from 98% to 2%), Solvent B: Acetonitrile+0.04% formic acid (from 2% to 98%)

$^1$H NMR (system 2): 400 Mhz Brucker Analytik GmbH, experiments in DMSO-d$_6$ $^1$H NMR (system 3): 500 Mhz Brucker BioSpin GmbH, experiments in DMSO-d$_6$ Example 2

N-[5-(3-Chloro-4-cyano-phenyl)-pyridin-3-yl]-4-methoxy-benzene-sulfonamide

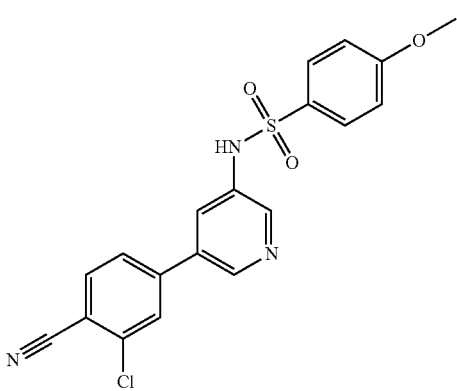 [SMILES: COc1ccc(S(=O)(=O)Nc2cncc(-c3ccc(C#N)c(Cl)c3)c2)cc1]

According to General Sulfonylation Procedure 2 in Example 1, to a solution of 4-(5-amino-pyridin-3-yl)-2-chloro-benzonitrile (20 mg, 87 μmol, 1 eq) in anhydrous pyridine (500 μl) was added 4-methoxy-benzenesulfonyl chloride (19.8 mg, 96 μmol, 1.1 eq).

The crude product was purified by Isco Combiflash® Companion™ flash chromatography system on normal phase (4 g SiO$_2$, flow rate 18 mL/min), eluting with mixtures of dichloromethane/methanol, to give N-[5-(3-chloro-4-cyano-phenyl)-pyridin-3-yl]-4-methoxy-benzenesulfonamide (15 mg, >95% purity, yield: 43%).

The isolated product was lyophilized and identified by LC-MS (system 1) and NMR (system 2): ESI-MS m/z: 400 [M+H]$^+$, retention time=2.61 min, $^1$H NMR (400 MHz, DMSO-d$_6$) δ ppm 3.77 (s, 3H) 7.02-7.06 (m, 2H) 7.69-7.72 (m, 2H) 7.73 (d, J=1.89 Hz, 1H) 7.75 (d, J=1.77 Hz, 1H) 7.99 (d, J=1.64 Hz, 1H) 8.06 (d, J=8.08 Hz, 1H) 8.27 (d, J=2.27 Hz, 1H) 8.60 (d, J=1.89 Hz, 1H) 10.58 (br. s., 1H).

Example 3

N-[5-(3-Chloro-4-cyano-phenyl)-pyridin-3-yl]-4-fluoro-benzene-sulfonamide

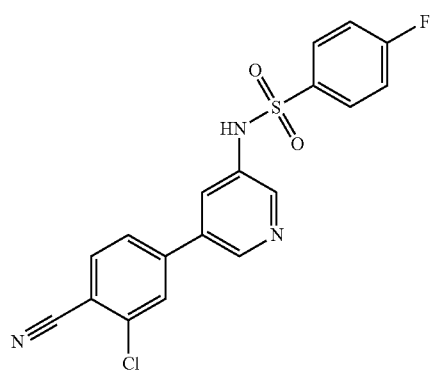 [SMILES: N#Cc1ccc(-c2cncc(NS(=O)(=O)c3ccc(F)cc3)c2)cc1Cl]

According to general General Sulfonylation Procedure 2 in example 1, to a solution of 4-(5-amino-pyridin-3-yl)-2-chloro-benzonitrile (20 mg, 87 μmol, 1 eq) in anhydrous pyridine (500 μl) was added 4-fluoro-benzenesulfonyl chloride (18.6 mg, 96 μmol, 1.1 eq). The product was purified by precipitation in methanol and lyophilized to give N-[5-(3-chloro-4-cyano-phenyl)-pyridin-3-yl]-4-fluoro-benzene-sulfonamide (13.5 mg, >95% purity, yield: 40%).

The isolated product was identified by LC-MS (system 1) and NMR (system 3): ESI-MS m/z: 388 [M+H]$^+$, retention time=2.29 min, $^1$H NMR (500 MHz, DMSO-d$_6$) δ ppm 7.38-7.44 (m, 3H) 7.78 (d, J=1.83 Hz, 1H) 7.79-7.83 (m, 1H) 7.83-7.90 (m, 2H) 8.05 (d, J=1.53 Hz, 1H) 8.10 (d, J=8.24 Hz, 1H) 8.31 (d, J=2.44 Hz, 1H) 8.69 (d, J=1.83 Hz, 1H) 10.78 (s, 1H).

Example 4

N-[5-(3-Chloro-4-cyano-phenyl)-pyridin-3-yl]-4-ethyl-benzene-sulfonamide

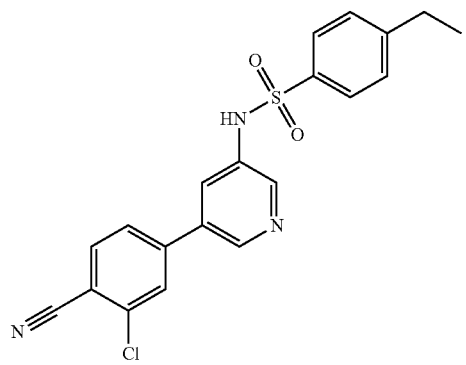 [SMILES: CCc1ccc(S(=O)(=O)Nc2cncc(-c3ccc(C#N)c(Cl)c3)c2)cc1]

According to General Sulfonylation Procedure 2 in example 1, to a solution of 4-(5-amino-pyridin-3-yl)-2-chloro-benzonitrile (20 mg, 87 μmol, 1 eq) in anhydrous pyridine (500 μl) was added 4-ethyl-benzenesulfonyl chloride (15.5 μl, 96 μmol, 1.1 eq).

The product was purified by precipitation in methanol and lyophilized to give N-[5-(3-chloro-4-cyano-phenyl)-pyridin-3-yl]-4-ethyl-benzenesulfonamide (14.3 mg, >95% purity, yield: 41.4%).

The isolated product was identified by LC-MS (system 1) and NMR (system 3): ESI-MS m/z: 398 [M+H]$^+$, retention time=2.54 min, $^1$H NMR (500 MHz, DMSO-d$_6$) δ ppm 1.14 (t, J=7.55 Hz, 3H) 2.63 (q, J=7.63 Hz, 2H) 7.39 (d, J=8.39 Hz, 2H) 7.71 (d, J=8.24 Hz, 2H) 7.76 (d, J=1.68 Hz, 1H) 7.77-7.78 (m, 1H) 8.01 (d, J=1.53 Hz, 1H) 8.09 (d, J=8.09 Hz, 1H) 8.31 (d, J=2.44 Hz, 1H) 8.64 (d, J=1.68 Hz, 1H) 10.70 (br. s., 1H).

Example 5

N-[5-(3-Chloro-4-cyano-phenyl)-pyridin-3-yl]-4-cyano-benzene-sulfonamide

According to General Sulfonylation Procedure 2 in example 1, to a solution of 4-(5-amino-pyridin-3-yl)-2-chloro-benzonitrile (20 mg, 87 μmol, 1 eq) in anhydrous pyridine (500 μl) was added 4-cyano-benzenesulfonyl chloride (19.3 mg, 96 μmol, 1.1 eq). The product was purified by preparative TLC, the plate was eluted with dichloromethane/methanol 95/5, to give (15.5 mg, >95% purity, yield: 39.4%).

The isolated product was lyophilized and identified by LC-MS (system 1) and NMR (system 3): ESI-MS m/z: 395 [M+H]$^+$, retention time=2.20 min, $^1$H NMR (500 MHz, DMSO-d$_6$) δ ppm 7.81 (d, J=8.09 Hz, 1H) 7.84 (br. s., 1H) 7.94-7.97 (m, 2H) 8.03-8.05 (m, 2H) 8.06 (br. s., 1H) 8.10 (d, J=8.24 Hz, 1H) 8.31 (s, 1H) 8.71 (s, 1H) 11.03 (br. s., 1H).

Example 6

N-[5-(3-Chloro-4-cyano-phenyl)-pyridin-3-yl]-4-trifluoromethyl-benzenesulfonamide

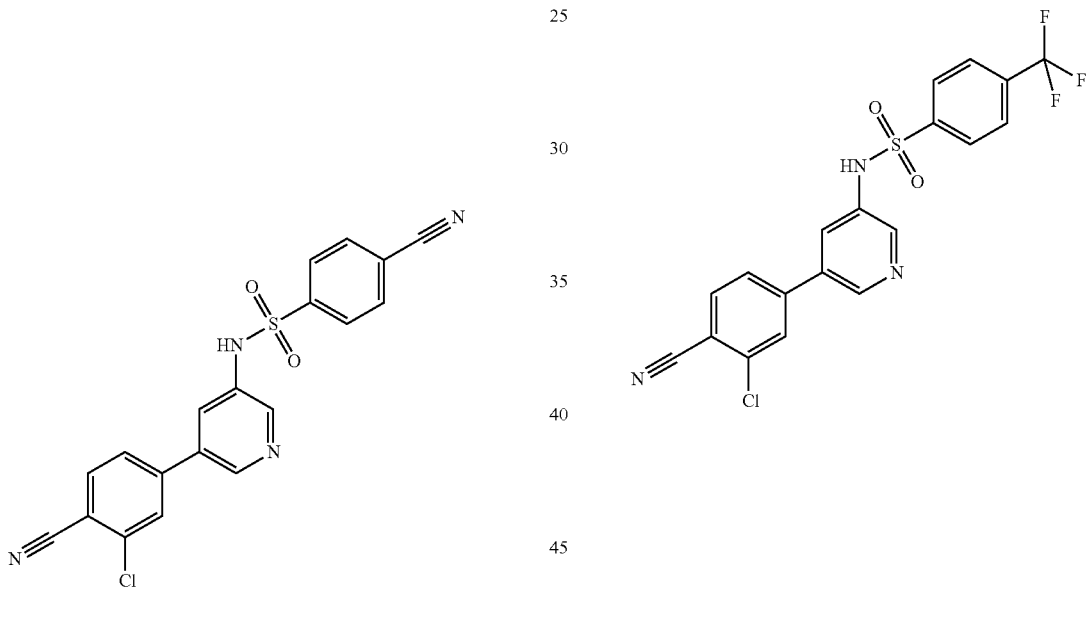

According to General Sulfonylation Procedure 2 in Example 1, to a solution of 4-(5-amino-pyridin-3-yl)-2-chloro-benzonitrile (20 mg, 87 μmol, 1 eq) in anhydrous pyridine (500 μl) was added 4-trifluoromethyl-benzenesulfonyl chloride (23.4 mg, 96 μmol, 1.1 eq).

The crude product was purified by Isco Combiflash® Companion™ flash chromatography system on normal phase (4 g SiO$_2$, flow rate 18 mL/min), eluting with mixtures of dichloromethane/methanol, to give N-[5-(3-chloro-4-cyano-phenyl)-pyridin-3-yl]-4-trifluoromethyl-benzenesulfonamide (15 mg, >95% purity, yield: 40%).

The isolated product was lyophilized and identified by LC-MS (system 1) and NMR (system 3): ESI-MS m/z: 438 [M+H]$^+$, retention time=2.57 min, $^1$H NMR (500 MHz, DMSO-d$_6$) δ ppm 7.80 (dd, J=8.24, 1.53 Hz, 1H) 7.82 (d, J=1.98 Hz, 1H) 7.93-7.98 (m, 2H) 7.98-8.03 (m, 2H) 8.04 (s, 1H) 8.09 (d, J8.09 Hz, 1H) 8.31 (s, 1H) 8.68 (br. s., 1H) 11.00 (br. s., 1H).

Example 7

N-[5-(3-Chloro-4-cyano-phenyl)-pyridin-3-yl]-4-fluoro-2-methyl-benzenesulfonamide

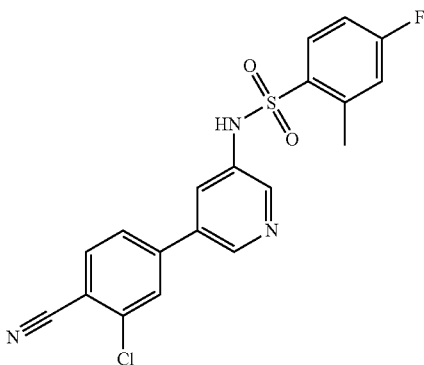 [SMILES: Cc1cc(F)ccc1S(=O)(=O)Nc1cncc(-c2ccc(C#N)c(Cl)c2)c1]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added 4-fluoro-2-methyl-benzenesulfonyl chloride (14 µl, 96 µmol, 1.1 eq).

The product was purified by precipitation in methanol and lyophilized to give N-[5-(3-chloro-4-cyano-phenyl)-pyridin-3-yl]-4-fluoro-2-methyl-benzenesulfonamide (17 mg, >95% purity, yield: 48.7%).

The isolated product was identified by LC-MS (system 1) and NMR (system 3): ESI-MS m/z: 402 [M+H]$^+$, retention time=2.44 min, $^1$H NMR (500 MHz, DMSO-d$_6$) δ ppm 2.61 (s, 3H) 7.17-7.23 (m, 1H) 7.30 (dd, J=9.92, 2.14 Hz, 1H) 7.70 (s, 1H) 7.74 (dd, J=8.09, 1.68 Hz, 1H) 7.99 (d, J=1.53 Hz, 1H) 8.01 (d, J=5.80 Hz, 1H) 8.09 (d, J=8.24 Hz, 1H) 8.33 (d, J=2.14 Hz, 1H) 8.60 (br. s., 1H) 10.94 (br. s., 1H).

Example 8

N-(5-(3-chloro-4-cyanophenyl)pyridin-3-yl)-2,2,2-trifluoroethanesulfonamide

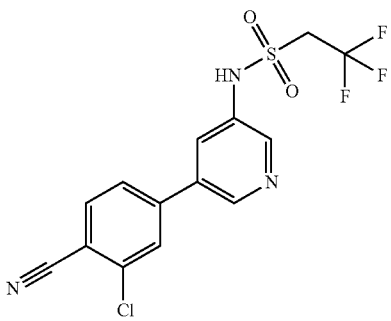 [SMILES: N#Cc1ccc(-c2cncc(NS(=O)(=O)CC(F)(F)F)c2)cc1Cl]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added 2,2,2-trifluoro-ethanesulfonyl chloride (10.6 µl, 96 µmol, 1.1 eq).

The product was purified by preparative TLC, the plate was eluted with dichloromethane/methanol 95/5, to give N-(5-(3-chloro-4-cyanophenyl)pyridin-3-yl)-2,2,2-trifluoroethanesulfonamide (9 mg, >95% purity, yield: 27.6%).

The isolated product was lyophilized and identified by LC-MS (system 1) and NMR (system 3): ESI-MS m/z: 376 [M+H]$^+$, retention time=2.10 min, $^1$H NMR (500 MHz, DMSO-d$_6$) δ ppm 4.75 (q, J=9.66 Hz, 2H) 7.87-7.91 (m, 2H) 8.11-8.14 (m, 1H) 8.14 (s, 1H) 8.46 (d, J=2.44 Hz, 1H) 8.74 (d, J=1.83 Hz, 1H) 10.94 (br. s., 1H).

Example 9

N-[5-(3-Chloro-4-cyano-phenyl)-pyridin-3-yl]-1-phenyl-methanesulfonamide

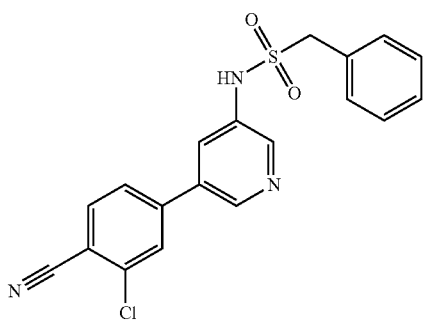 [SMILES: N#Cc1ccc(-c2cncc(NS(=O)(=O)Cc3ccccc3)c2)cc1Cl]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added alpha-toluenesulfonyl chloride (18.3 mg, 96 µmol, 1.1 eq).

The crude product was purified by Isco Combiflash® Companion™ flash chromatography system on normal phase (4 g SiO$_2$, flow rate 18 mL/min), eluting with mixtures of dichloromethane/methanol, to give N-[5-(3-chloro-4-cyano-phenyl)-pyridin-3-yl]-1-phenyl-methanesulfonamide (14.3 mg, >95% purity, yield: 42.8%).

The isolated product was lyophilized and identified by LC-MS (system 1) and NMR (system 2): ESI-MS m/z: 384 [M+H]$^+$, retention time=2.22 min, $^1$H NMR (400 MHz, DMSO-d$_6$) δ ppm 4.65 (s, 2H) 7.29-7.32 (m, 5H) 7.63 (t, J=2.21 Hz, 1H) 7.76 (dd, J=8.15, 1.71 Hz, 1H) 8.00 (d, J=1.64

Hz, 1H) 8.09 (d, J=8.21 Hz, 1H) 8.35 (d, J=2.53 Hz, 1H) 8.61 (d, J=2.02 Hz, 1H) 10.24 (br. s., 1H).

Example 10

N-(5-(3-chloro-4-cyanophenyl)pyridin-3-yl)-2-phenoxyethanesulfonamide

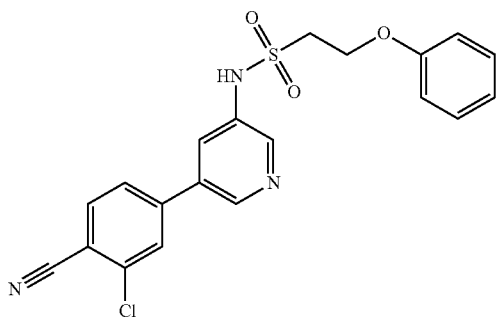 [SMILES: N#Cc1ccc(-c2cncc(NS(=O)(=O)CCOc3ccccc3)c2)cc1Cl]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added 2-phenoxy-ethanesulfonyl chloride (21.14 mg, 96 µmol, 1.1 eq).

The product was purified by preparative TLC, the plate was eluted with dichloromethane/methanol 95/5, to give N-(5-(3-chloro-4-cyanophenyl)pyridin-3-yl)-2-phenoxyethanesulfonamide (8.1 mg, >95% purity, yield: 22.5%).

The isolated product was lyophilized and identified by LC-MS (system 1) and NMR (system 2): ESI-MS m/z: 414 [M+H]$^+$, retention time=2.32 min, $^1$H NMR (400 MHz, DMSO-d$_6$) δ ppm 3.73 (t, J=5.43 Hz, 2H) 4.31 (t, J=5.49 Hz, 2H) 6.75-6.80 (m, 2H) 6.89 (t, J=7.33 Hz, 1H) 7.18-7.24 (m, 2H) 7.77 (dd, J=8.08, 1.77 Hz, 1H) 7.83 (t, J=2.27 Hz, 1H) 8.00 (d, J=1.64 Hz, 1H) 8.07 (d, J=8.21 Hz, 1H) 8.45 (d, J=2.40 Hz, 1H) 8.62 (d, J=2.02 Hz, 1H) 10.38 (br. s., 1H).

Example 11

N-[5-(3-Chloro-4-cyano-phenyl)-pyridin-3-yl]-4-methyl-benzenesulfonamide

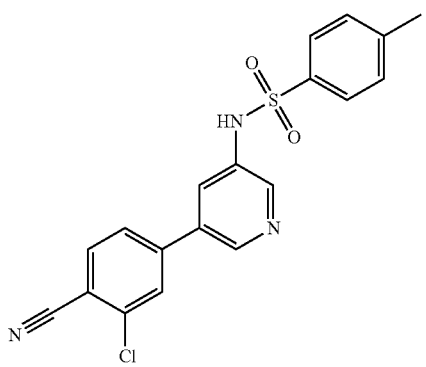 [SMILES: Cc1ccc(S(=O)(=O)Nc2cncc(-c3ccc(C#N)c(Cl)c3)c2)cc1]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added 4-methyl-benzenesulfonyl chloride (18.3 mg, 96 µmol, 1.1 eq).

The crude product was purified by Isco Combiflash® Companion™ flash chromatography system on normal phase (4 g SiO$_2$, flow rate 18 mL/min), eluting with mixtures of dichloromethane/methanol, to give N-[5-(3-chloro-4-cyano-phenyl)-pyridin-3-yl]-4-methyl-benzenesulfonamide (14.8 mg, >95% purity, yield: 44.3%).

The isolated product was lyophilized and identified by LC-MS (system 1) and NMR (system 2): ESI-MS m/z: 384 [M+H]$^+$, retention time=2.35 min, $^1$H NMR (400 MHz, DMSO-d$_6$) δ ppm 2.32 (s, 3H) 7.31-7.36 (m, 2H) 7.64-7.68 (m, 2H) 7.73 (d, J=1.64 Hz, 1H) 7.75 (d, J=2.02 Hz, 1H) 7.99 (d, J=1.52 Hz, 1H) 8.07 (d, J=8.21 Hz, 1H) 8.28 (d, J=2.27 Hz, 1H) 8.62 (d, J=1.77 Hz, 1H) 10.64 (br. s., 1H).

Example 12

N-(5-(3-chloro-4-cyanophenyl)pyridin-3-yl)-1-(2-chlorophenyl)methanesulfonamide

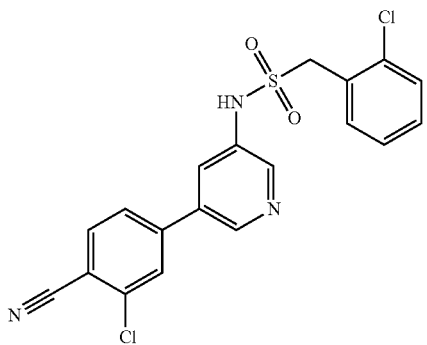 [SMILES: N#Cc1ccc(-c2cncc(NS(=O)(=O)Cc3ccccc3Cl)c2)cc1Cl]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added (2-chloro-phenyl)-methanesulfonyl chloride (21.6 mg, 96 µmol, 1.1 eq).

The crude product was purified by Isco Combiflash® Companion™ flash chromatography system on normal phase (4 g SiO$_2$, flow rate 18 mL/min), eluting with mixtures of dichloromethane/methanol, to give N-[5-(3-chloro-4-cyano-phenyl)-pyridin-3-yl]-1-(2-chloro-phenyl)-methanesulfonamide (15.1 mg, >95% purity, yield: 41.5%).

The isolated product was lyophilized and identified by LC-MS (system 1) and NMR (system 2): ESI-MS m/z: 418 [M+H]$^+$, retention time=2.34 min, $^1$H NMR (400 MHz, DMSO-d$_6$) δ ppm 4.80 (s, 2H) 7.30-7.32 (m, 2H) 7.37-7.39 (m, 1H) 7.47-7.49 (m, 1H) 7.69 (t, J=2.27 Hz, 1H) 7.75 (dd, J=8.08, 1.77 Hz, 1H) 7.98 (d, J=1.77 Hz, 1H) 8.09 (d, J=8.08 Hz, 1H) 8.37 (d, J=2.53 Hz, 1H) 8.61 (d, J=1.89 Hz, 1H) 10.50 (br. s., 1H).

Example 13

N-(5-(3-chloro-4-cyanophenyl)pyridin-3-yl)-1-(4-fluorophenyl)methanesulfonamide

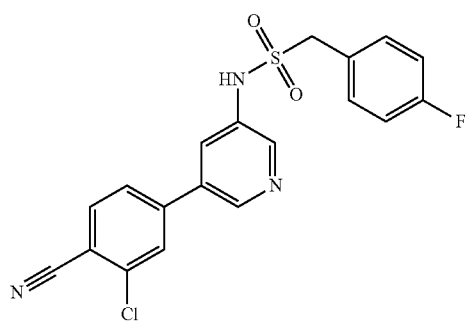 [SMILES: N#Cc1ccc(-c2cncc(NS(=O)(=O)Cc3ccc(F)cc3)c2)cc1Cl]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added (4-fluoro-phenyl)-methanesulfonyl chloride (20 mg, 96 µmol, 1.1 eq).

The crude product was purified by Isco Combiflash® Companion™ flash chromatography system on normal phase (4 g SiO$_2$, flow rate 18 mL/min), eluting with mixtures of dichloromethane/methanol, to give N-[5-(3-chloro-4-cyano-phenyl)-pyridin-3-yl]-1-(4-fluoro-phenyl)-methanesulfonamide (8.2 mg, >95% purity, yield: 23.4%).

The isolated product was lyophilized and identified by LC-MS (system 1) and NMR (system 2): ESI-MS m/z: 402 [M+H]$^+$, retention time=2.24 min, $^1$H NMR (400 MHz, DMSO-d$_6$) δ ppm 4.67 (s, 2H) 7.09-7.16 (m, 2H) 7.29-7.37 (m, 2H) 7.66 (t, J=2.27 Hz, 1H) 7.78 (dd, J=8.15, 1.71 Hz, 1H) 8.02 (d, J=1.64 Hz, 1H) 8.09 (d, J=8.08 Hz, 1H) 8.34 (d, J=2.40 Hz, 1H) 8.61 (d, J=2.02 Hz, 1H) 10.24 (br. s., 1H).

Example 14

Cyclopropanesulfonic acid [5-(3-chloro-4-cyano-phenyl)-pyridin-3-yl]-amide

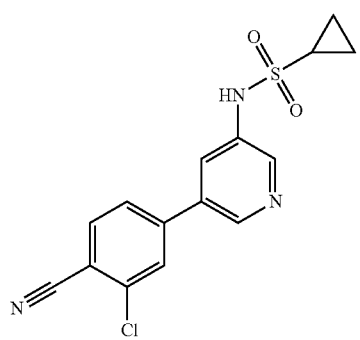 [SMILES: N#Cc1ccc(-c2cncc(NS(=O)(=O)C3CC3)c2)cc1Cl]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added cyclopropanesulfonyl chloride (9.8 µl, 96 µmol, 1.1 eq).

The crude product was purified by Isco Combiflash® Companion™ flash chromatography system on normal phase (4 g SiO$_2$, flow rate 18 mL/min), eluting with mixtures of dichloromethane/methanol, to give cyclopropanesulfonic acid [5-(3-chloro-4-cyano-phenyl)-pyridin-3-yl]-amide (8.5 mg, >95% purity, yield: 29.2%).

The isolated product was lyophilized and identified by LC-MS (system 1) and NMR (system 2): ESI-MS m/z: 334 [M+H]$^+$, retention time=1.90 min, $^1$H NMR (400 MHz, DMSO-d$_6$) δ ppm 0.93-0.99 (m, 4H) 2.80-2.85 (m, 1H) 7.84 (dd, J=8.08, 1.64 Hz, 1H) 7.89 (t, J=2.21 Hz, 1H) 8.08 (d, J=8.08 Hz, 1H) 8.10 (s, 1H) 8.48 (d, J=2.40 Hz, 1H) 8.70 (d, J=1.89 Hz, 1H) 10.15 (br. s., 1H).

Example 15

N-(5-(3-chloro-4-cyanophenyl)pyridin-3-yl)propane-1-sulfonamide

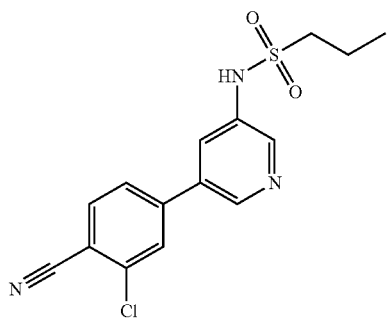 [SMILES: CCCS(=O)(=O)Nc1cncc(-c2ccc(C#N)c(Cl)c2)c1]

According to General Sulfonylation Procedure 2 in Example 1, to a solution of 4-(5-amino-pyridin-3-yl)-2-chloro-benzonitrile (20 mg, 87 µmol, 1 eq) in anhydrous pyridine (500 µl) was added propane-1-sulfonyl chloride (10.8 µl, 96 µmol, 1.eq).

The crude product was purified by Isco Combiflash® Companion™ flash chromatography system on normal phase (4 g SiO$_2$, flow rate 18 mL/min), eluting with mixtures of dichloromethane/methanol, to give N-(5-(3-chloro-4-cyanophenyl)pyridin-3-yl)propane-1-sulfonamide (13.6 mg, >95% purity, yield: 46.5%).

The isolated product was lyophilized and identified by LC-MS (system 1) and NMR (system 2): ESI-MS m/z: 336 [M+H]$^+$, retention time=2.02 min, 1H NMR (400 MHz, DMSO-d$_6$) δ ppm 0.92 (t, J=7.39 Hz, 3H) 1.62-1.69 (m, 2H) 2.90-2.94 (m, 2H) 7.62 (t, J=2.27 Hz, 1H) 7.76 (dd, J=8.15, 1.71 Hz, 1H) 7.98 (d, J=1.39 Hz, 1H) 8.03 (d, J=8.21 Hz, 1H) 8.20 (d, J=2.40 Hz, 1H) 8.28 (d, J=2.02 Hz, 1H) 10.12 (br. s., 1H).

Example 16

N-(5-(3-chloro-4-cyanophenyl)pyridin-3-yl)butane-sulfonamide

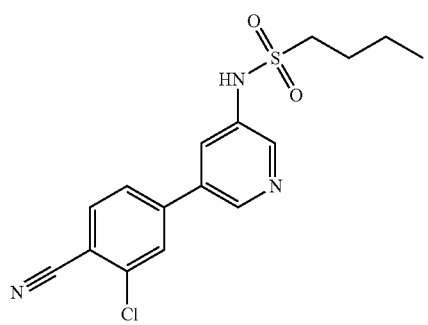 [SMILES: CCCCS(=O)(=O)Nc1cncc(-c2ccc(C#N)c(Cl)c2)c1]

According to General Sulfonylation Procedure 2 in Example 1, to a solution of 4-(5-amino-pyridin-3-yl)-2-chloro-benzonitrile (20 mg, 87 μmol, 1 eq) in anhydrous pyridine (500 μl) was added butane-1-sulfonyl chloride (12.4 mg, 96 μmol, 1.1 eq).

The product was purified by preparative TLC, the plate was eluted with dichloromethane/methanol 95/5, to give N-(5-(3-chloro-4-cyanophenyl)pyridin-3-yl)butane-1-sulfonamide (14.2 mg, >95% purity, yield: 46.6%).

The isolated product was lyophilized and identified by LC-MS (system 1) and NMR (system 3): ESI-MS m/z: 350 [M+H]$^+$, retention time=2.21 min, $^1$H NMR (500 MHz, DMSO-d$_6$) δ ppm 0.84 (t, J=7.32 Hz, 3H) 1.33-1.41 (m, 2H) 1.63-1.70 (m, 2H) 3.24 (t, J=7.72 Hz, 2H) 7.84-7.88 (m, 2H) 8.12 (d, J=8.09 Hz, 1H) 8.11 (d, J=1.68 Hz, 1H) 8.48 (d, J=2.44 Hz, 1H) 8.70 (d, J=1.83 Hz, 1H) 10.24 (br. s., 1H).

Example 17

N-(5-(4-cyano-3-methoxyphenyl)pyridin-3-yl)-2,2,2-trifluoroethanesulfonamide

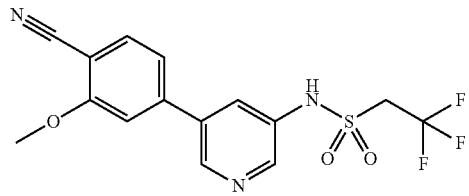 [SMILES: COc1cc(-c2cncc(NS(=O)(=O)CC(F)(F)F)c2)ccc1C#N]

Step 1: synthesis of 2-Methoxy-4-(4,4,5,5-tetramethyl-[1,3,2]dioxaborolan-2-yl)-benzonitrile

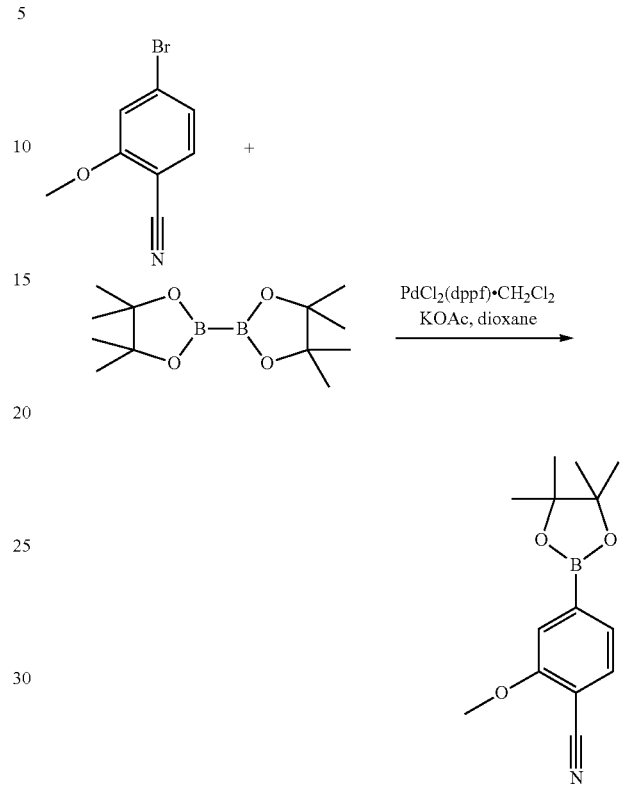

A mixture of 4-Bromo-2-methoxy-benzonitrile (1 g, 4.72 mmol), 4,4,4',4',5,5,5',5'-octamethyl-2,2'-bi(1,3,2-dioxaborolane) (1.198 g, 4.72 mmol), potassium acetate (0.926 g, 9.43 mmol) and PdCl$_2$(dppf).CH$_2$Cl$_2$ adduct (0.193 g, 0.236 mmol) in 1,4-dioxane (10 mL, dry) was heated to 80° C. for 5 h. The mixture was concentrated, and the residue was purified by isco column (ethyl acetate-heptane, v/v, 10%-20%) and yielded a colorless solid (850 mg). $^1$H NMR (400 MHz, CDCl$_3$): δ 1.35 (s, 12H), 3.97 (s, 3H), 7.35 (s, 1H), 7.54 (d, J=7.5 Hz, 1H), 7.42 (d, J=7.5 Hz, 1H).

Step 2: Synthesis of 4-(5-aminopyridin-3-yl)-2-methoxybenzonitrile

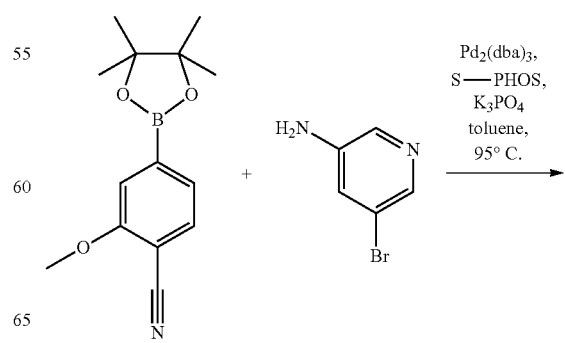

-continued

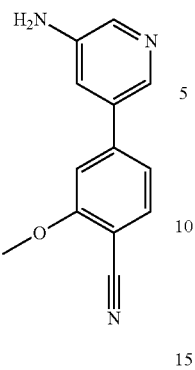

General Suzuki reaction procedure 1 in Example 1 was used here without modification. ESI (M+H) 226.1.

Step 3: Synthesis of N-(5-(4-cyano-3-methoxyphenyl)pyridin-3-yl)-2,2,2-trifluoroethane sulfonamide

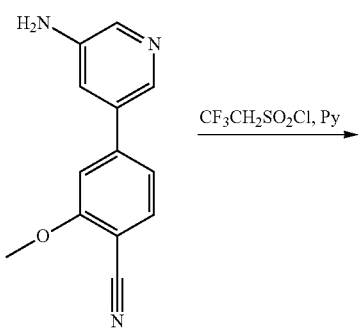

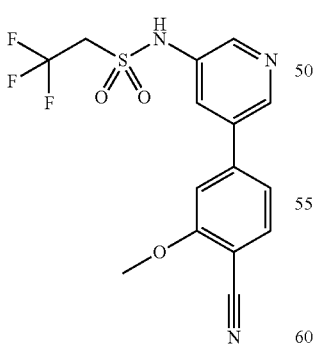

General sulfonylation procedure 1 in Example 1 was used here. ESI-MS m/z: 372.0 [M+H]+, $^1$H NMR (400 MHz, MeOD) δ ppm 4.05 (s, 3H), 4.36 (q, J=9.4 Hz, 2H), 7.35 (dd, J=1.4, 7.9 Hz, 1H), 7.41 (s, 1H), 7.74 (d, J=7.9 Hz, 1H), 8.00 (d, J=2 Hz, 1H), 8.49 (d, J=2 Hz, 1H), 8.68 (d, J=1.7 Hz, 1H).

The following compounds were synthesized in similar manner:

Example 18

N-(5-(4-cyano-3-methoxyphenyl)pyridin-3-yl)ethanesulfonamide

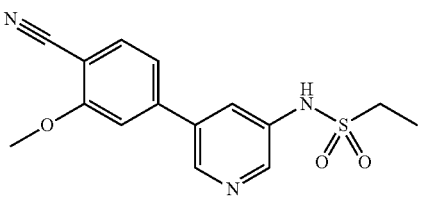 [SMILES: CCS(=O)(=O)Nc1cncc(-c2ccc(C#N)c(OC)c2)c1]

General sulfonylation procedure 1 in Example 1 was used here: ESI-MS m/z: 318.1 [M+H]+, $^1$H NMR (400 MHz, MeOD) δ ppm 1.35 (t, J=7.3 Hz, 3H), 3.22 (q, J=7.3 Hz, 2H), 4.05 (s, 3H), 7.34 (dd, J=1.44, 8 Hz, 1H), 7.40 (s, 1H), 7.74 (d, J=8 Hz, 1H), 7.97 (t, J=2 Hz, 1H), 8.47 (d, J=2 Hz, 1H), 8.62 (d, J=2 Hz, 1H).

Example 19

N-(5-(4-cyano-3-methoxyphenyl)pyridin-3-yl)cyclopropane-sulfonamide

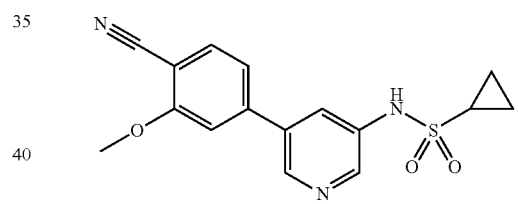

General sulfonylation procedure 1 in Example 1 was used here. ESI-MS m/z: 330.0 [M+H]+, $^1$H NMR (400 MHz, MeOD) δ ppm 0.90-1.10 (m, 4H), 2.60-2.70 (m, 1H), 4.05 (s, 3H), 7.34 (dd, J=1.40, 8 Hz, 1H), 7.41 (s, 1H), 7.74 (d, J=8 Hz, 1H), 8.00 (t, J=2 Hz, 1H), 8.51 (d, J=2 Hz, 1H), 8.65 (d, J=2 Hz, 1.8H).

Example 20

N-((5-(4-cyano-3-methoxyphenyl)pyridin-3-yl)methyl)methane-sulfonamide

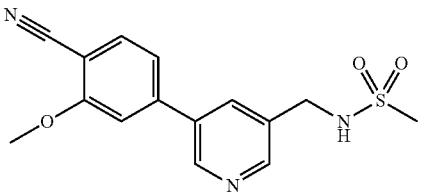

Step 1: Synthesis of 4-(5-Formyl-pyridin-3-yl)-2-methoxy-benzonitrile

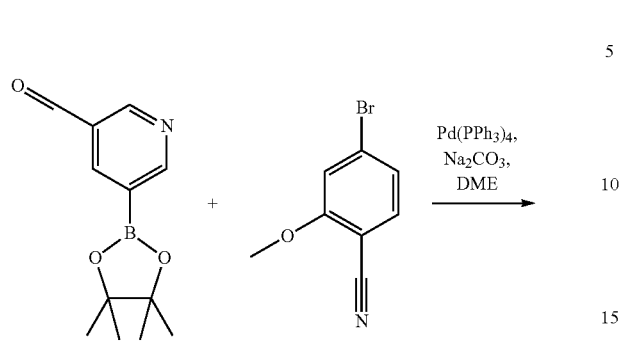

A mixture of 4-bromo-2-methoxybenzonitrile (0.424 g, 2.000 mmol), 5-(4,4,5,5-tetramethyl-1,3,2-dioxaborolan-2-yl)nicotinaldehyde (0.466 g, 2.000 mmol), tetrakis(triphenylphosphine)palladium(0) (0.058 g, 0.050 mmol) and sodium carbonate (2M in water, 2.00 mL, 4.00 mmol) in DME (50 mL) was heated to 90° C. for 6 h. After filtration through a pad of dry $Na_2SO_4$ and concentration, the residue was purified by column and yielded a colorless solid (430 mg). $^1$H NMR (400 MHz, $CDCl_3$): δ 4.04 (s, 3H), 6.99 (s, 1H), 7.27 (d, J=4.7 Hz, 1H), 7.71 (d, J=7.9 Hz, 1H), 8.34 (t, J=2 Hz, 1H), 9.07 (d, J=2.36 Hz, 1H), 9.12 (d, J=1.9 Hz, 1H), 10.22 (s, 1H).

Step 2: Synthesis of N-((5-(4-cyano-3-methoxyphenyl)pyridin-3-yl)methyl)methanesulfonamide

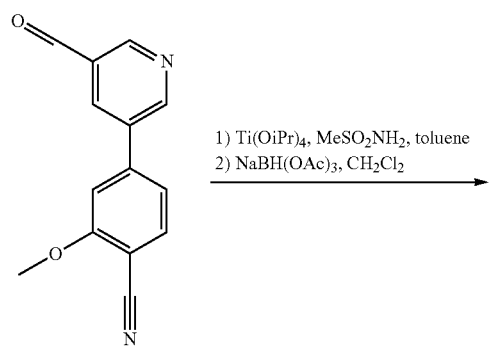

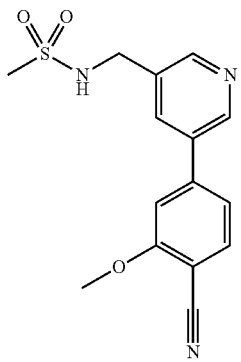

(General reductive amination procedure): Titanium(IV) isopropoxide (0.098 ml, 0.336 mmol) was added dropwise to a mixture of 4-(5-formyl-pyridin-3-yl)-2-methoxy-benzonitrile (40 mg, 0.168 mmol) and methanesulfonamide (23.96 mg, 0.252 mmol) in toluene (10 mL). The resulting mixture was heated to 140° C. (bath temperature) for 3 hr. After concentration, the residue was dissolved in $CH_2Cl_2$ (10 mL). $NaBH(OAc)_3$ (107 mg, 0.504 mmol) was added at room temperature. The resulting mixture was stirred at room temperature overnight (18 h). The reaction was quenched by the addition of saturated $NaHCO_3$ solution (10 mL). The mixture was filtered, and the organic layer was separated. The aqueous layer was extracted with $CH_2Cl_2$ (15 mL×3). The combined extracts were dried over $Na_2SO_4$. After filtration and concentration, the residue was purified by isco column (MeOH—$CH_2Cl_2$, v/v, 15 to 3%) and yielded a colorless solid (31 mg). HRMS 317.08431 M+, $C_{15}H_{15}N_3O_3S$ requires 317.08341, ESI-MS m/z: 318.0 [M+H]$^+$, $^1$H NMR (400 MHz, $CDCl_3$) δ ppm 2.94 (s, 3H), 3.96 (s, 3H), 4.38 (d, J=6.3 Hz, 2H), 4.70 (m, 1H), 7.06 (d, J=1.24 Hz, 1H), 7.16 (m, 1H), 7.60 (d, J=8 Hz, 1H), 7.87 (s, 1H), 8.57 (d, J=2 Hz, 1H), 8.73 (d, J=2 Hz, 1H).

The following compounds were synthesized in similar manner.

Example 21

N-((5-(4-cyano-3-methoxyphenyl)pyridin-3-yl)methyl)ethanesulfonamide

The general reductive amination procedure described in example 20 was used here: HRMS 332.10777 (M+H)$^+$, $C_{16}H_{18}N_3O_3S$ requires 332.0991 $^1$H NMR (400 MHz, $CDCl_3$) δ ppm 1.39 (t, J=7.2 Hz, 3H), 3.07 (q, J=7.2 Hz, 2H), 4.02 (s, 3H), 4.42 (d, J=5.8 Hz, 2H), 4.80 (m, 1H), 7.12 (s, 1H), 7.18 (d, J=8 Hz, 1H), 7.66 (d, J=8 Hz, 1H), 7.94 s, 1H), 8.62 (s, 1H), 8.78 (s, 1H).

Example 22

N-((5-(4-cyano-3-methoxyphenyl)pyridin-3-yl)methyl)-1,1,1-trifluoromethanesulfonamide

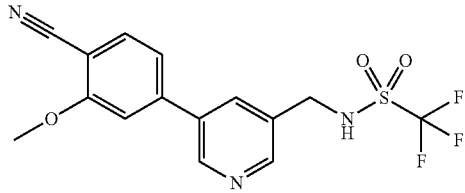 [SMILES: COc1cc(-c2cncc(CNS(=O)(=O)C(F)(F)F)c2)ccc1C#N]

The general reductive amination procedure described in Example 20 was used here: HRMS 371.05582 M+, $C_{15}H_{12}F_3N_3O_3S$ requires 371.05515; ESI-MS m/z: 371.9 [M+H]+, $^1$H NMR (400 MHz, CDCl$_3$): δ 3.96 (s, 3H), 4.51 (s, 2H), 7.04 (s, 1H), 7.13 (d, J=7.6 Hz, 1H), 7.61 (d, J=7.4 Hz, 1H), 7.83 (s, 1H), 8.53 (s, 1H), 8.74 (s, 1H).

Example 23

N-((5-(3-chloro-4-cyanophenyl)pyridin-3-yl)methyl)ethanesulfonamide

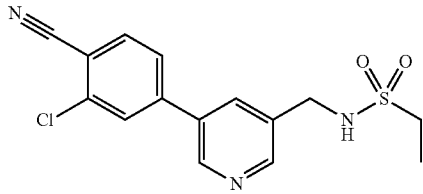 [SMILES: CCS(=O)(=O)NCc1cncc(-c2ccc(C#N)c(Cl)c2)c1]

Step 1: Synthesis of 2-Chloro-4-(5-formyl-pyridin-3-yl)-benzonitrile

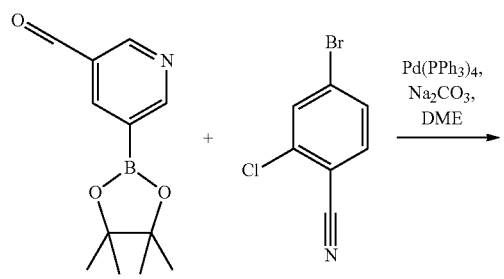

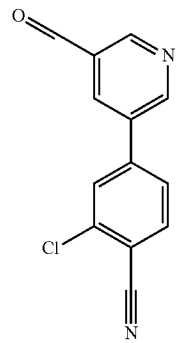

A mixture of 4-bromo-2-chlorobenzonitrile (1.082 g, 5 mmol), 5-(4,4,5,5-tetramethyl-1,3,2-dioxaborolan-2-yl)nicotinaldehyde (1.165 g, 5.00 mmol), Pd(PPh$_3$)$_4$ (0.144 g, 0.125 mmol), sodium carbonate (2.5 mL, 5.00 mmol) in 1,4-dioxane (20 mL) was heated to reflux for 6 h. After cooling to room temperature, the solid was filtered and washed by ethyl acetate and water. After drying under vacuum, yellow powder was collected (1 g). $^1$H NMR (400 MHz, CDCl$_3$): δ 7.63 (dd, J=1.68, 8 Hz, 1H), 7.79 (d, J=1.68 Hz, 1H), 7.83 (d, J=8 Hz, 1H), 8.35 (dd, J=2.24 Hz, 2.04 Hz, 1H), 9.07 (d, J=2.36 Hz, 1H), 9.15 (d, J=1.88 Hz, 1H), 10.22 (s, 1H).

Step 2: Synthesis of N-((5-(3-chloro-4-cyanophenyl)pyridin-3-yl)methyl)ethane sulfonamide

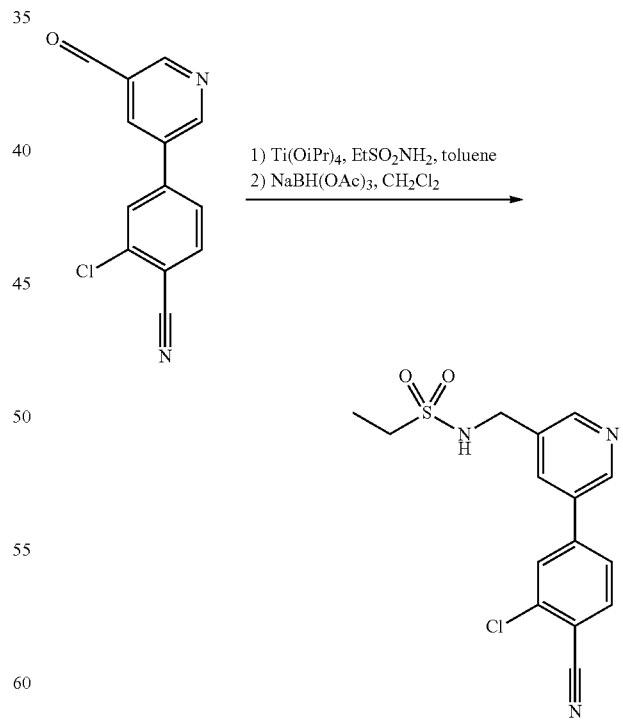

The general reductive amination procedure described in Example 20 was used here: ESI-MS m/z: 336.0 [M+H]+, $^1$H NMR (400 MHz, CDCl$_3$) δ ppm 1.34 (t, J=7.37 Hz, 3H), 3.01 (q, J=7.37 Hz, 2H), 4.37 (d, J=6.3 Hz, 2H), 4.50 (m, 1H), 7.53

(dd, J=1.7, 8 Hz, 1H), 7.67 (d, J=1.7 Hz, 1H), 7.73 (d, J=8 Hz, 1H), 7.89 (s, 1H), 8.58 (d, J=2 Hz, 1H), 8.72 (d, J=2 Hz, 1H).

Example 24

N-((5-(4-cyano-3-ethoxyphenyl)pyridin-3-yl)methyl)ethanesulfonamide

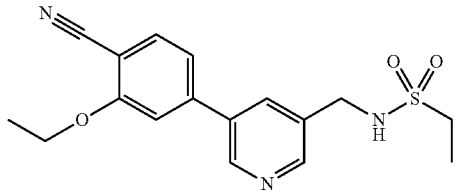 [SMILES: CCOc1cc(-c2cncc(CNS(=O)(=O)CC)c2)ccc1C#N]

Step 1: Synthesis of 4-Bromo-2-ethoxy-benzonitrile

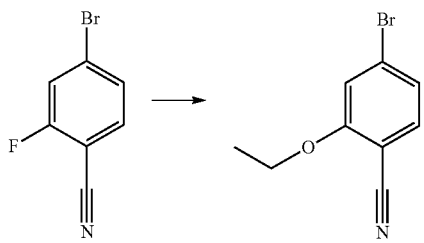

A mixture of 4-Bromo-2-fluoro-benzonitrile (5 g, 25.00 mmol), potassium carbonate (10.37 g, 75.0 mmol), ethanol (6.86 mL, 117 mmol) in DMF (50 mL) was heated at 60° C. for overnight. After filtration and concentration, the redisue was dissolved in ethyl acetate (150 mL), and the solution was washed with water (30 mL) and brine (50 mL). After drying over Na2SO4, filtration and concentration, a light brown solid (5.7 g) was obtained without further purification. $^1$H NMR (400 MHz, CDCl$_3$): δ 1.49 (t, J=7 Hz, 3H), 4.14 (q, J=7 Hz, 2H), 7.11 (d, J=1.7 Hz, 1H), 7.14 (dd, J=8.1, 1.7 Hz, 1H), 7.40 (d, J=8.1 Hz, 1H).

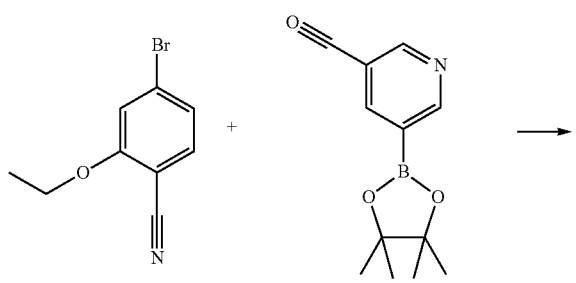

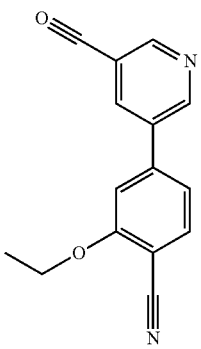

Step 2: Synthesis of 2-ethoxy-4-(5-formylpyridin-3-yl)benzonitrile

A mixture of 4-bromo-2-ethoxybenzonitrile (1.13 g, 5.00 mmol), 5-(4,4,5,5-tetramethyl-1,3,2-dioxaborolan-2-yl)nicotinaldehyde (1.165 g, 5.00 mmol), sodium carbonate (5.00 mL, 10.00 mmol) and Pd(PPh$_3$)$_4$ (1.136 g, 0.125 mmol) in DME (20 mL) was heated to reflux for 6 h. After cooling to room temperature, filtration, drying over Na$_2$SO$_4$, concentration, a colorless solid was obtained. $^1$H NMR (400 MHz, CDCl$_3$): δ 7.14 (d, J=1.5 Hz, 1H), 7.23 (dd, J=8, 1.5 Hz, 1H), 7.70 (d, J 8=Hz, 1H), 8.33 (t, J=2 Hz, 1H), 9.06 (d, J=2 Hz, 1H), 9.11 (d, J=2 Hz, 1H), 10.21 (s, 1H).

Step 3: synthesis of N-((5-(4-cyano-3-ethoxyphenyl)pyridin-3-yl)methyl)ethane sulfonamide

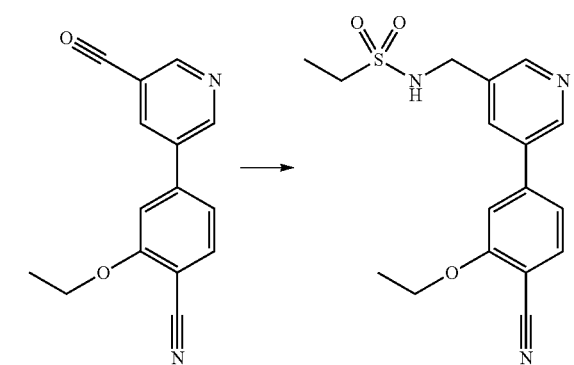

Titanium(IV) isopropoxide (234 μL, 0.800 mmol) was added dropwise to a mixture of 2-ethoxy-4-(5-formylpyridin-3-yl)benzonitrile (101 mg, 0.400 mmol), ethanesulfonamide (52.4 mg, 0.480 mmol) in toluene (20 mL). The resulting mixture was heated at 140° C. for 2 hr. After concentration, the residue was dissolved in CH$_2$Cl$_2$ (10 mL) and sodium triacetoxyborohydride (254 mg, 1.200 mmol) was added at room temperature. The resulting mixture was stirred overnight, and quenched with NaHCO$_3$ solution. After filtration, extraction and concentration, the residue was purified by flash column (MeOH—CH$_2$Cl$_2$, v/v, 1%-3.5%) and yielded a colorless oil (100 mg) which turned to colorless solid after standing. ESI-MS m/z: 317.9 [M+H]$^+$, $^1$H NMR (400 MHz, CDCl$_3$): δ 1.40 (t, J=7.4 Hz, 3H), 1.53 (t, J=7 Hz, 3H), 3.08 (q, J=7.4 Hz, 2H), 4.25 (q, J=7 Hz, 2H), 4.43 (d, J=6.2 Hz, 2H), 4.59 (brs, 1H), 7.10 (d, J=1.4 Hz, 1H), 7.19 (dd, J=8, 1.6 Hz, 1H), 7.66 (d, J=8 Hz, 1H), 7.93 (s, 1H), 8.62 (s, 1H), 8.77 (s, 1H).

Example 25

N-(1-(5-(3-chloro-4-cyanophenyl)pyridin-3-yl)-2-methylpropyl)ethanesulfonamide

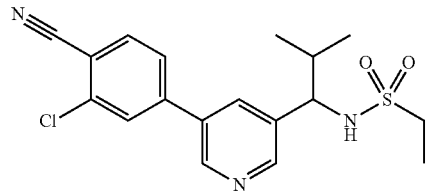

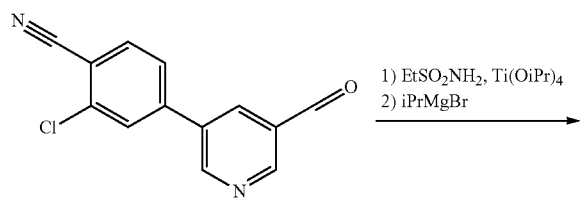

1) EtSO$_2$NH$_2$, Ti(OiPr)$_4$
2) iPrMgBr

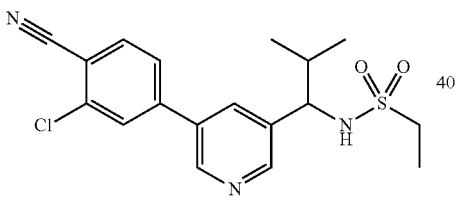

(General Grignard addition reaction procedure): a mixture of 2-Chloro-4-(5-formyl-pyridin-3-yl)-benzonitrile (0.243 g, 1 mmol), titanium(IV) isopropoxide (0.586 mL, 2.000 mmol), ethanesulfonamide (0.109 g, 1.000 mmol) in Toluene (20 mL) was heated to reflux for 4 hr. After concentration, the residue was dissolved in THF (15 mL) and cooled to −40° C. A solution of isopropenylmagnesium bromide (1.500 mL, 3.000 mmol) was added dropwise and the resulting mixture was slowly warmed up to −20° C. and stirred at this temperature for 4 hr. After quenched by NH$_4$Cl solution, filtration, extraction with CH$_2$Cl$_2$, the solution was dried over Na$_2$SO$_4$, and concentrated, the residue was purified by flash column (MeOH—CH$_2$Cl$_2$, v/v, 1%-3%) and yielded a yellow solid (90 mg). Enantiomers were separated by 40% EtOH 60% heptane on a Chiralpak IA column. First peak 14 min (enantiomer 1), second peak 20 min (enantiomer 2). ESI-MS m/z: 378.1 [M+H]$^+$, $^1$H NMR (400 MHz, CDCl$_3$): δ 0.93 (d, J=6.7 Hz, 3H), 1.06 (d, J=6.7 Hz, 3H), 1.21 (t, J=8.0 Hz, 3H), 2.04-2.11 (m, 1H), 2.76-2.91 (m, 2H), 4.36 (t, J=7.4 Hz, 1H), 4.90 (d, J=7.6 Hz, 1H), 7.58 (d, J=8.2 Hz, 1H), 7.72 (s, 1H), 7.77 (s, 1H), 7.78 (d, J=8.2 Hz, 1H), 8.61 (s, 1H), 8.77 (s, 1H).

The following compounds were synthesized in similar manner:

Example 26

N-(1-(5-(4-cyano-3-methoxyphenyl)pyridin-3-yl)ethyl)ethanesulfonamide

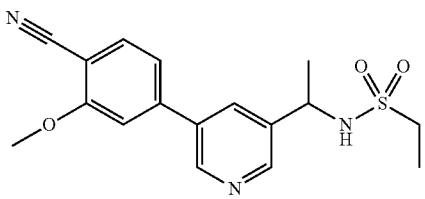 [SMILES: CCS(=O)(=O)NC(C)c1cncc(-c2ccc(C#N)c(OC)c2)c1]

The general Grignard addition reaction procedure described in Example 25 was used here. Two enantiomers were separated by Chiral HPLC (Chiralpak IA column, MeOH 20% in SFC. Flow 40, Pressure 20.00) enantiomer-1: t1=1.47 min, enantiomer-2: t2=2.13 min. HRMS 345.11623 for M+, C$_{17}$H$_{19}$N$_3$O$_3$S requires 345.11471. ESI-MS m/z: 346.0 [M+H]$^+$, $^1$H NMR (400 MHz, CDCl$_3$): δ ppm 1.25 (t, J=7.29 Hz, 3H), 1.58 (d, J=6.76 Hz, 3H), 2.77-2.88 (m, 2H), 3.96 (s, 3H), 4.58 (d, J=5.04 Hz, 1H), 4.71-4.75 (m, 1H), 7.06 (s, 1H), 7.14 (d, J=8 Hz, 1H), 7.6 (d, J=8 Hz, 1H), 7.80 (s, 1H), 8.61 (s, 1H), 8.71 (s, 1H).

Example 27

N-(1-(5-(3-chloro-4-cyanophenyl)pyridin-3-yl)ethyl)ethanesulfonamide

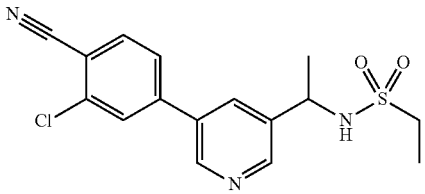 [SMILES: CCS(=O)(=O)NC(C)c1cncc(-c2ccc(C#N)c(Cl)c2)c1]

The general Grignard addition reaction procedure described in Example 25 was used here. Two enantiomers were separated by Chiral HPLC (chiralpak IA-H column, MeOH 20% in SFC. Flow 80, Pressure 130) to enantiomer-1: t1=5 min, enantiomer-2: t2=10 min. ESI-MS m/z: 349.9 [M+H]$^+$, $^1$H NMR (400 MHz, CDCl$_3$): δ 1.46 (t, J=8 Hz, 3H), 1.79 (d, J=8 Hz, 3H), 2.95-3.10 (m, 2H), 4.65-4.70 (m, 1H), 4.90-5.00 (m, 1H), 7.74 (d, J=8 Hz, 1H), 7.88 (s, 1H), 7.94 (d, J=8 Hz, 1H), 8.00 (s, 1H), 8.85 (s, 1H), 8.92 (s, 1H).

Example 28

N-(1-(5-(3-chloro-4-cyanophenyl)pyridin-3-yl)butyl)ethanesulfonamide

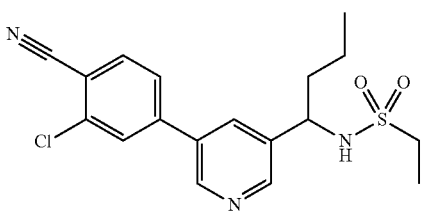 [SMILES: CCCC(NS(=O)(=O)CC)c1cncc(-c2ccc(C#N)c(Cl)c2)c1]

The general Grignard addition reaction procedure described in Example 25 was used here. Two enantiomers were separated by Chiral HPLC (ChiralpaK IA-H column, heptane-Ethanol, v/v, 60:40). enantiomer-1: t1=10 min, enantiomer-2: t2=16.9 min. ESI-MS m/z: 378.2 [M+H]$^+$, $^1$H NMR (400 MHz, MeOD): δ 0.99 (m, 3H), 1.17 (m, 3H), 1.29-1.52 (m, 2H), 1.73-1.91 (m, 2H), 2.79-2.99 (m, 2H), 4.56 (m, 1H), 7.82 (dd, J=1.6, 8 Hz, 1H), 7.94 (d, J=8 Hz, 1H), 8.01 (d, J=1.3 Hz, 1H), 8.62 (s, 1H), 8.80 (d, J=2 Hz, 1H).

Example 29

N-((5-(3-chloro-4-cyanophenyl)pyridin-3-yl)(cyclopropyl)methyl)ethanesulfonamide

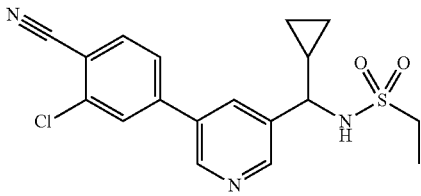 [SMILES: CCS(=O)(=O)NC(c1cncc(-c2ccc(C#N)c(Cl)c2)c1)C1CC1]

Step 1 (Method 1): Synthesis of N-((5-(3-chloro-4-cyanophenyl)pyridin-3-yl)(cyclopropyl)methyl)ethanesulfonamide

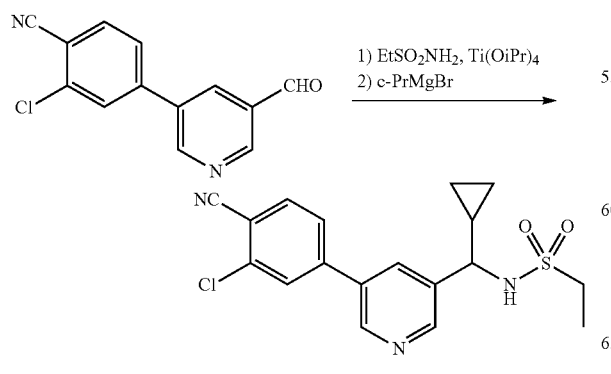

Titanium(IV) isopropoxide (0.365 mL, 1.245 mmol) was added to a mixture of 2-chloro-4-(5-formylpyridin-3-yl)benzonitrile (as prepared in Example 23, step 1; 0.151 g, 0.622 mmol), ethanesulfonamide (0.085 g, 0.778 mmol) in toluene (10 mL) at room temperature. The resulting mixture was heated to reflux for 4 h. After concentration, the residue was dissolved in THF (5 mL), and cooled to −40° C. Cyclopropylmagnesium bromide (3.73 mL, 1.867 mmol) was added dropwise, and the resulting mixture was slowly warmed up to room temperature and stirred overnight. After quenching by saturated NH$_4$Cl solution, the residue was purified by flash column (ethyl acetate-heptane, v/v, 40%-60%) yielded a slightly yellow solid.

Step 1 (Method 2): Synthesis of N-((5-bromopyridin-3-yl)(cyclopropyl)methyl)ethanesulfonamide

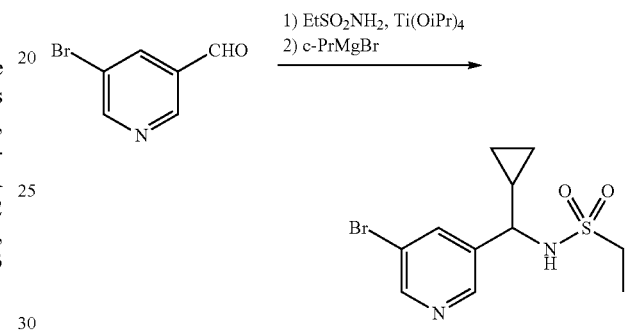

A mixture of 5-bromonicotinaldehyde (372 mg, 2 mmol), ethanesulfonamide (273 mg, 2.500 mmol) and titanium(IV) isopropoxide (1172 μl, 4.00 mmol) in toluene (20 mL) was heated to reflux for 2 h. After concentration, the residue was dissolved in THF (25 mL) and cooled to −40° C. A solution of cyclopropylmagnesium bromide (10 mL, 5.00 mmol) was added dropwise and the resulting mixture was slowly warmed up to −20° C. and stirred at this temperature for 4 h. After quenching by saturated NH$_4$Cl solution, filtration, extraction with CH$_2$Cl$_2$, the solution was dried over Na$_2$SO$_4$, and concentrated. The residue was purified by flash column (ethyl acetate/heptane, v/v, 10%-35%) and yielded the title product as oil (430 mg). $^1$H NMR (400 MHz, CDCl$_3$): δ 0.2-0.3 (m, 1H), 0.4-0.5 (m, 1H), 0.5-0.6 (m, 1H), 0.6-0.7 (m, 1H), 1.0-1.1 (m, 1H), 1.1-1.2 (m, 3H), 2.55-2.75 (m, 2H), 3.6-3.7 (m, 1H), 4.51 (brd, J=4.8 Hz, 1H), 7.73 (s, 1H), 8.42 (s, 1H), 8.51 (s, 1H).

Step 2 (Method 2): Synthesis of N-((5-(3-chloro-4-cyanophenyl)pyridin-3-yl)(cyclopropyl)methyl)ethanesulfonamide

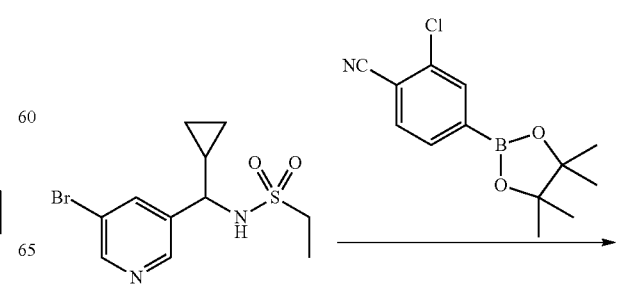

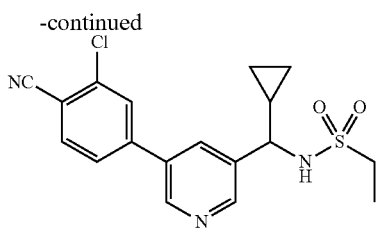

A mixture of N-((5-bromopyridin-3-yl)(cyclopropyl)methyl)ethanesulfonamide (5 g, 15.66 mmol), 2-chloro-4-(4,4,5,5-tetramethyl-1,3,2-dioxaborolan-2-yl)benzonitrile (as prepared in Example 1, step 1; 4.13 g, 15.66 mmol), sodium carbonate (15.66 mL, 31.3 mmol) and PdCl2(dppf).CH$_2$Cl$_2$ adduct (0.320 g, 0.392 mmol) in DMF (100 mL) was heated to 100° C. for 25 min. After concentration, the residue was dissolved into CH$_2$Cl$_2$ and filtered through a pad of Na$_2$SO$_4$. The solution was absorbed into celite and concentrated. The residue was purified by flash column (ethyl acetate/heptane, 30%-50%-80%, v/v) and yielded the title compound as a colorless solid (5.0 g). Chiral separation by chiral HPLC (Chiralpak AD-H using Supercritical fluid chromatography. 25% Methanol at 65 grams per minute with supercritical CO$_2$) afforded enantiomer 1 (S)—N-((5-(3-chloro-4-cyanophenyl)pyridin-3-yl)(cyclopropyl)methyl)ethanesulfonamide (retention time=3 min), and enantiomer 2 (R)—N-((5-(3-chloro-4-cyanophenyl)pyridin-3-yl)(cyclopropyl)methyl)ethanesulfonamide (retention time=4 min). ESI-MS m/z: 376.2 [M+H]$^+$, $^1$H NMR (400 MHz, CDCl$_3$): δ 0.37-0.40 (m, 1H), 0.51-0.55 (m, 1H), 0.57-0.68 (m, 1H), 0.70-0.77 (m, 1H), 1.15-1.27 (m, 3H), 2.70-2.88 (m, 2H), 3.85 (dd, J=5 Hz, 9 Hz, 1H), 4.68 (d, J=5 Hz, 1H), 7.53 (dd, J=1.5 Hz, 8 Hz, 1H), 7.67 (d, J=1.5 Hz, 1H), 7.73 (d, J=8 Hz, 1H), 7.80 (t, J=2 Hz, 1H), 8.67 (d, J=2 Hz, 1H), 8.72 (d, J=2 Hz, 1H).

Example 30

N-((5-(3-chloro-4-cyanophenyl)pyridin-3-yl)(cyclopropyl)methyl)methanesulfonamide

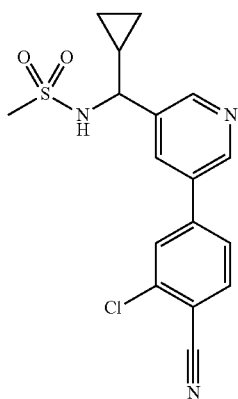 [SMILES: CS(=O)(=O)NC(c1cncc(-c2ccc(C#N)c(Cl)c2)c1)C1CC1]

Titanium isopropoxide (1.16 mL, 3.96 mmol) was added to a mixture of 2-Chloro-4-(5-formyl-pyridin-3-yl)-benzonitrile (480 mg, 1.98 mmol) and methanesulfonamide (188 mg, 1.98 mmol) in toluene (15 mL) at room temperature. The resulting mixture was refluxed for 2 h. After concentration, the residue was dissolved in THF (10 mL) and cooled to −40° C. A solution of c-PrMgBr (0.5 M in THF, 11.9 mL, 5.93 mmol) was added dropwise and the resulting mixture was stirred at −36° C. for 1 h. The reaction was quenched by addition of saturated NH$_4$Cl solution. The resulting mixture was filtered, and the organic layer was separated. After concentration, the residue was purified by flash column (MeOH—CH$_2$Cl$_2$, v/v, 0-3%) to give N-((5-(3-chloro-4-cyanophenyl)pyridin-3-yl)(cyclopropyl)methyl)methanesulfonamide (351 mg, 49%); ESI-MS m/z: 362 [M+1]$^+$, $^1$HNMR (MeOD, 400 MHz) δ 8.83 (d, J=2.0 Hz, 1H), 8.69 (d, J=2.0 Hz, 1H), 8.24 (t, J=2.0 Hz, 1H), 7.93 (4H, s), 3.96 (d, J=9.2 Hz, 1H), 3.06-2.93 (m, 2H), 1.35-1.30 (m, 1H), 1.30 (t, J=7.2 Hz, 1H), 0.81-0.76 (m, 1H), 0.67-0.61 (m, 2H), 0.54-0.49 (m, 1H).

Enantiomers were separated by chiral HPLC (Chiralpak IA-H column, EtOH/Heptane, v/v, 60/40) to enantiomer 1(1$^{st}$ peak, t=12.46 min), enantiomer 2 (2$^{nd}$ peak, t=17.09 min).

Example 31

N-(5-(4-cyano-3-methoxyphenyl)pyridin-3-yl)(cyclopropyl)methyl)ethanesulfonamide

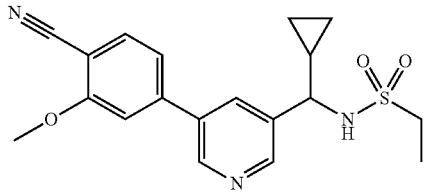 [SMILES: CCS(=O)(=O)NC(c1cncc(-c2ccc(C#N)c(OC)c2)c1)C1CC1]

The general Grignard addition reaction procedure described in Example 25 was used here. Enantiomers were separated by chiral HPLC (Chiralpak AD-H using Supercritical fluid chromatography 15% MeOH:IPA (1:1). ESI-MS m/z: 372.2 [M+H]$^+$, $^1$H NMR (400 MHz, CDCl$_3$): δ 0.3-0.8 (m, 4H), 1.20 (m, 1H), 1.24 (t, J=7 Hz, 3H), 2.72-2.86 (m, 2H), 3.86 (m, 1H), 3.96 (s, 3H), 4.73 (brS, 1H), 7.06 (s, 1H), 7.15 (dd, J=7.8 Hz, 1H), 7.60 (d, J=7.8 Hz, 1H), 7.80 (s, 1H), 8.64 (s, 1H), 8.72 (s, 1H).

Example 32

N-(5-(4-cyano-2-methoxyphenyl)pyridin-3-yl)(cyclopropyl)methyl)ethanesulfonamide

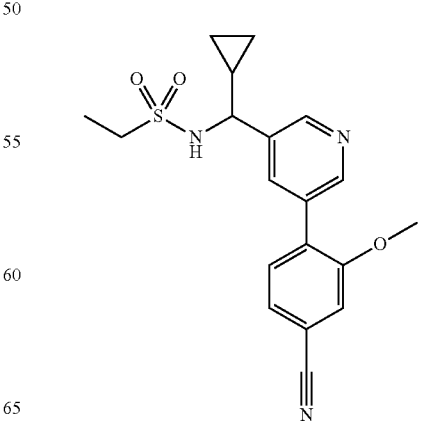

Step 1: Synthesis of 4-(5-Formyl-pyridin-3-yl)-3-methoxy-benzonitrile

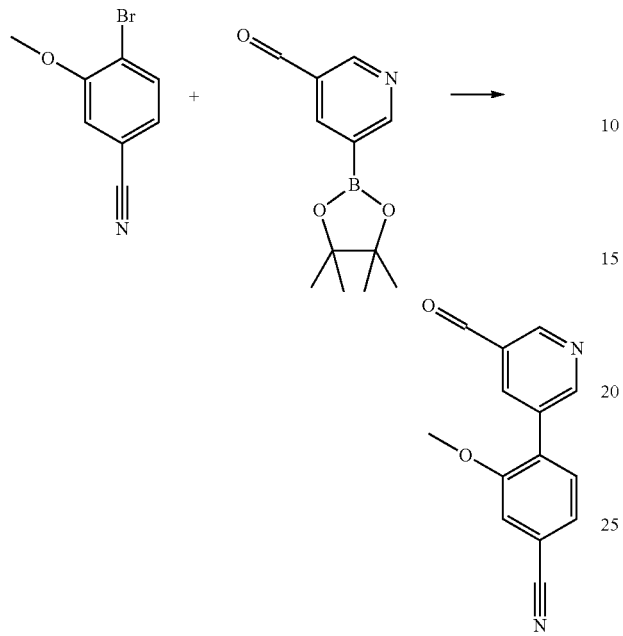

A mixture of 4-bromo-3-methoxy-benzonitrile (400 mg, 1.88 mmol), 5-(4,4,5,5-tetramethyl-[1,3,2]dioxaborolan-2-yl)-pyridine-3-carbaldehyde (440 mg, 1.88 mmol), PdCl$_2$(PPh$_3$)$_2$ (108 mg, 0.15 mmol) and Na$_2$CO$_3$ (2M in water, 1.88 mL, 3.77 mmol) in 1,4-dioxane (8 mL) was heated at 100° C. for 1.5 h. After concentration in vacuo, the resulting residue was purified by flash column to give the title compound (449 mg, 100%) as white solid; ESI-MS m/z: 239 [M+1]$^+$.

Step 2: N-((5-(4-cyano-2-methoxyphenyl)pyridin-3-yl)(cyclopropyl)methyl) ethanesulfonamide

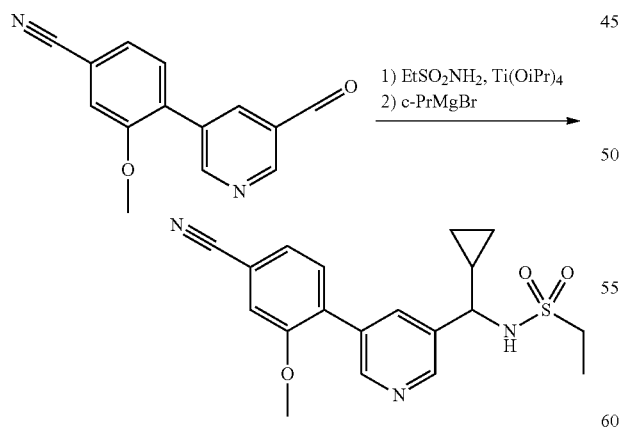

Titanium isopropoxide (1.1 mL, 3.77 mmol) was added to a mixture of 4-(5-formyl-pyridin-3-yl)-3-methoxy-benzonitrile (449 mg, 1.88 mmol) and ethanesulfonamide (226 mg, 2.07 mmol) in toluene (10 mL) at room temperature. The resulting mixture was heated to reflux for 2 h. After concentration, the residue was dissolved in THF (7 mL) and a solution of c-PrMgBr (0.5 M in THF, 18.8 mL, 9.42 mmol) was added dropwise at −40° C. The resulting mixture was stirred at −36° C. for 1 h. Saturated NH$_4$Cl solution was added to the reaction mixture. The resulting mixture was diluted with ethyl acetate and brine and subsequently filtered. The organic layer was separated and concentrated. The residue was purified by flash column (EtOAc/Heptane=0-60%) to give the title compound (182 mg, 26% yield); ESI-MS m/z: 372 [M+1]; $^1$H-NMR (MeOD, 400 MHz) δ 8.59 (1H, d, J=2.0 Hz), 8.57 (1H, d, J=2.0 Hz), 8.07 (1H, t, J=2.0 Hz), 7.54 (1H, d, J=7.6 Hz), 7.49 (1H, s), 7.45 (1H, d, J=7.6 Hz), 7.42 (1H, d, J=8.4 Hz), 3.89 (3H, s), 3.88 (1H, d, J=9.2 Hz), 3.01-2.88 (2H, m), 1.30-1.25 (1H, m), 1.25 (1H, t, J=7.2 Hz), 0.77-0.70 (1H, m), 0.64-0.54 (2H, m), 0.48-0.42 (1H, m)

Enantiomers were separated by chiral HPLC (Chiralpak AD-H column, EtOH/Heptane, v/v, 50/50) to the enantiomer 1 (R)—N-((5-(4-cyano-2-methoxyphenyl)pyridin-3-yl)(cyclopropyl)methyl)ethanesulfonamide (retention time=11.38 min) and the enantiomer 2 (S)—N-((5-(4-cyano-2-methoxyphenyl)pyridin-3-yl)(cyclopropyl)methyl)ethanesulfonamide (retention time=16.62 min).

Example 33

N-((5-(4-cyano-3-fluorophenyl)pyridin-3-yl)(cyclopropyl)methyl)ethanesulfonamide

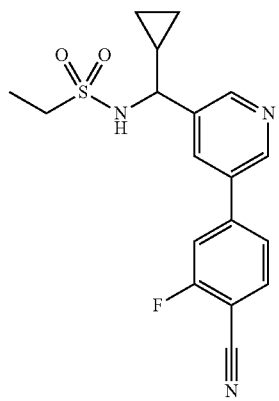 [SMILES: CCS(=O)(=O)NC(c1cncc(-c2ccc(C#N)c(F)c2)c1)C1CC1]

Step 1: Synthesis of 2-Fluoro-4-(5-formyl-pyridin-3-yl)-benzonitrile

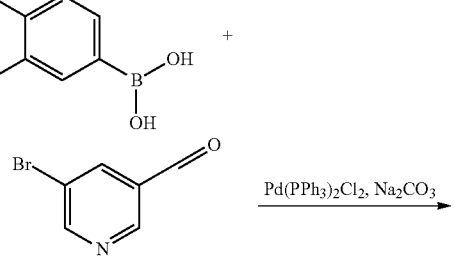

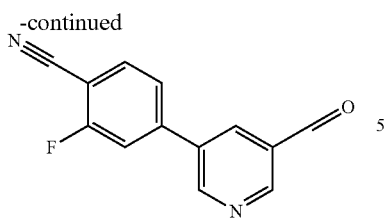

A mixture of 4-cyano-3-fluorophenylboronic acid (0.495 g, 3 mmol), 5-bromonicotinaldehyde (0.558 g, 3.00 mmol), sodium carbonate (2M in water, 3.00 mL, 6.00 mmol), bis(triphenylphosphine)palladium(II) chloride (0.053 g, 0.075 mmol) in DMF (10 mL) was heated to 95° C. for 3 h. After concentration, the residue was dissolved into $CH_2Cl_2$-MeOH and mixed with silica gel and concentrated. After flash column (MeOH—$CH_2Cl_2$, v/v, 0.5%-1%) yielded a colorless solid (170 mg) ESI-MS m/z: 227 [M+1]$^+$.

Step 2: Synthesis of N-((5-(4-cyano-3-fluorophenyl)pyridin-3-yl)(cyclopropyl)-methyl)ethanesulfonamide

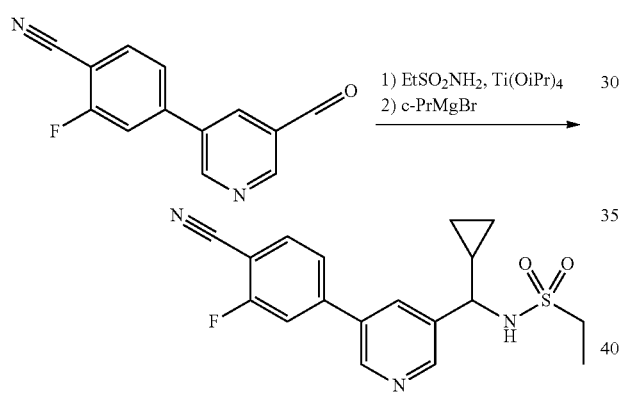

Titanium isopropoxide (0.98 mL, 3.36 mmol) was added to a mixture of 2-fluoro-4-(5-formyl-pyridin-3-yl)-benzonitrile (380 mg, 1.68 mmol) and ethanesulfonamide (183 mg, 1.68 mmol) in toluene (14 mL) at RT. The resulting mixture was heated to reflux for 2 h. After concentration, the residue was dissolved in THF (100 mL) and a solution of c-PrMgBr (0.5 M in THF, 16.8 mL, 8.40 mmol) was added dropwise at −40° C., and the resulting mixture was stirred at −36° C. for 1 h. Saturated $NH_4Cl$ solution was added to the reaction mixture. The resulting mixture was diluted with ethyl acetate and brine, and subsequently filtered. The organic layer was separated to concentrate and purified by flash column (10% MeOH/DCM=0-30%) to give the title compound (185 mg, 30%); ESI-MS m/z: 360 [M+1]$^+$, $^1$HNMR (MeOD, 400 MHz) δ ppm 8.85 (1H, d, J=2.0 Hz), 8.72 (1H, d, J=2.0 Hz), 8.25 (1H, t, J=2.0 Hz), 7.94 (1H, d, J=8.0 Hz), 7.82-7.77 (2H, m), 3.95 (1H, d, J=9.2 Hz), 3.89 (3H, s), 3.07-2.96 (2H, m), 1.34-1.29 (1H, m), 1.31 (1H, t, J=7.2 Hz), 0.81-0.76 (1H, m), 0.67-0.62 (2H, m), 0.55-0.51 (1H, m)

Enantiomers were separated by chiral HPLC (Chiralpak IA-H, EtOH/Heptane, v/v, 70/30) to enantiomer-1 (S)—N-((5-(4-cyano-3-fluorophenyl)pyridin-3-yl)(cyclopropyl)methyl)ethanesulfonamide (retention time=10.51 min), and the enantiomer-2 (R)—N-((5-(4-cyano-3-fluorophenyl)pyridin-3-yl)(cyclopropyl)methyl)ethanesulfonamide (retention time=18.59 min).

Example 34

N-(5-(4-cyano-2-fluorophenyl)pyridin-3-yl)(cyclopropyl)methyl)ethanesulfonamide

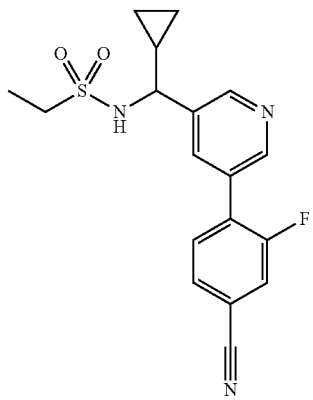 [SMILES: CCS(=O)(=O)NC(c1cncc(-c2ccc(C#N)cc2F)c1)C1CC1]

Step 1: Synthesis of N-((5-bromopyridin-3-yl)(cyclopropyl)methyl)ethane-sulfonamide

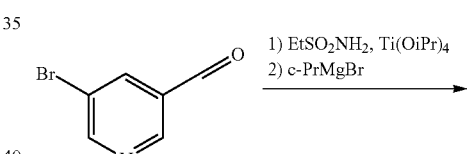

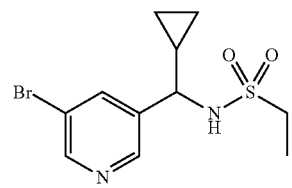

A mixture of 5-bromonicotinaldehyde (1.860 g, 10 mmol), ethanesulfonamide (1.091 g, 10.00 mmol) and titanium(IV) isopropoxide (5.86 mL, 20.00 mmol) in Toluene (20 mL) was heated to reflux for 2 h. After concentration, the residue was dissolved in THF (25 mL) and cooled to −40° C. A solution of cyclopropylmagnesium bromide (50.0 mL, 25.00 mmol) was added dropwise and the resulting mixture was slowly warmed up to −20° C. and stirred at this temperature for 4 h. After quenching with a $NH_4Cl$ solution, filtration and extraction with $CH_2Cl_2$, the solution was dried over $Na_2SO_4$, filtered and concentrated to give a residue which was purified by flash column (ethyl acetate/heptane, v/v, 10%-35%) to yield the title compound (1.5 g). $^1$H NMR (400 MHz, $CDCl_3$): δ 0.2-0.3 (m, 1H), 0.4-0.5 (m, 1H), 0.5-0.6 (m, 1H), 0.6-0.7 (m, 1H), 1.0-1.1 (m, 1H), 1.1-1.2 (m, 3H), 2.55-2.75 (m, 2H), 3.6-3.7 (m, 1H), 4.51 (brd, J=4.8 Hz, 1H), 7.73 (s, 1H), 8.42 (s, 1H), 8.51 (s, 1H).

Step 2: Synthesis of N-((5-(4-cyano-2-fluorophenyl)pyridin-3-yl)(cyclopropyl)methyl)ethanesulfonamide

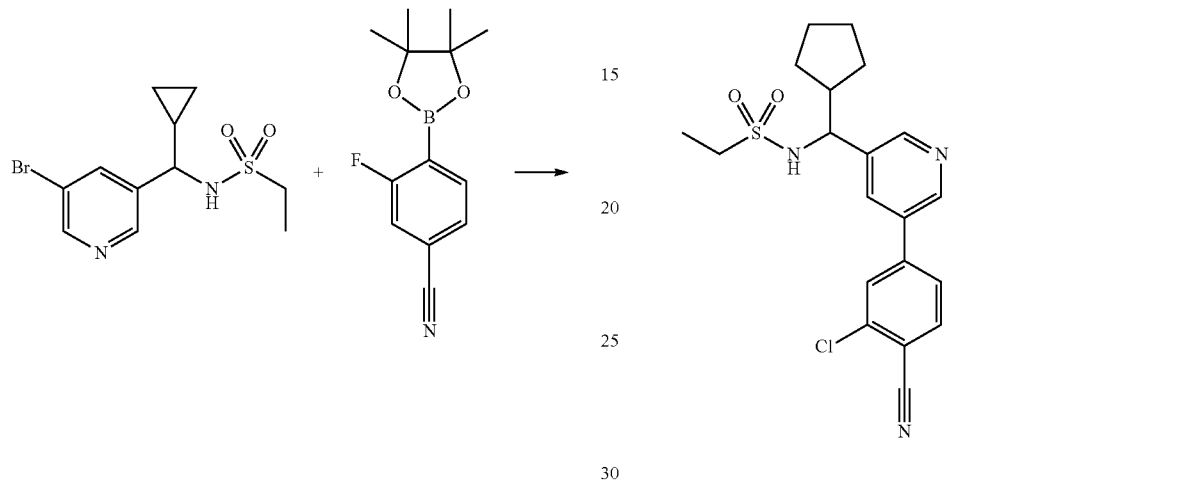

(General Suzuki reaction procedure 2) A mixture of 3-Fluoro-4-(4,4,5,5-tetramethyl-[1,3,2]dioxaborolan-2-yl)-benzonitrile (333 mg, 1.35 mmol), N-((5-bromopyridin-3-yl)(cyclopropyl)methyl)ethanesulfonamide (430 mg, 1.35 mmol), PdCl$_2$(PPh$_3$)$_2$ (77 mg, 0.10 mmol) and Na$_2$CO$_3$ (2M in water, 1.35 mL, 2.70 mmol) in DMF (6 mL) heated at 100° C. under N$_2$ for 2 h. The solvent was removed in vacuo, and the residue was purified by flash column (EtOAc/Heptane, v/v, 0-50%) to give the title compound (270 mg, 56% yield); ESI-MS m/z: 360 [M+1]$^+$. $^1$HNMR (MeOD, 400 MHz) δ 8.72 (1H, d, J=2.0 Hz), 8.71 (1H, d, J=2.0 Hz), 8.17 (1H, bs), 7.83-7.75 (3H, m), 3.95 (1H, d, J=8.8 Hz), 3.52 (3H, s), 3.05-2.92 (2H, m), 1.32-1.28 (1H, m), 1.30 (1H, t, J=7.2 Hz), 0.80-0.76 (1H, m), 0.67-0.61 (2H, m), 0.52-0.48 (1H, m). Enantiomers were separated by chiral HPLC (Chiralpak AS-H, EtOH/Heptane, v/v, 30/70) to the first peak (enantiomer 1, t=9.68 min), and the second peak (enantiomer 2, t=13.68 min).

Example 35

N-((5-(3-chloro-4-cyanophenyl)pyridin-3-yl)(cyclopentyl)methyl)ethanesulfonamide

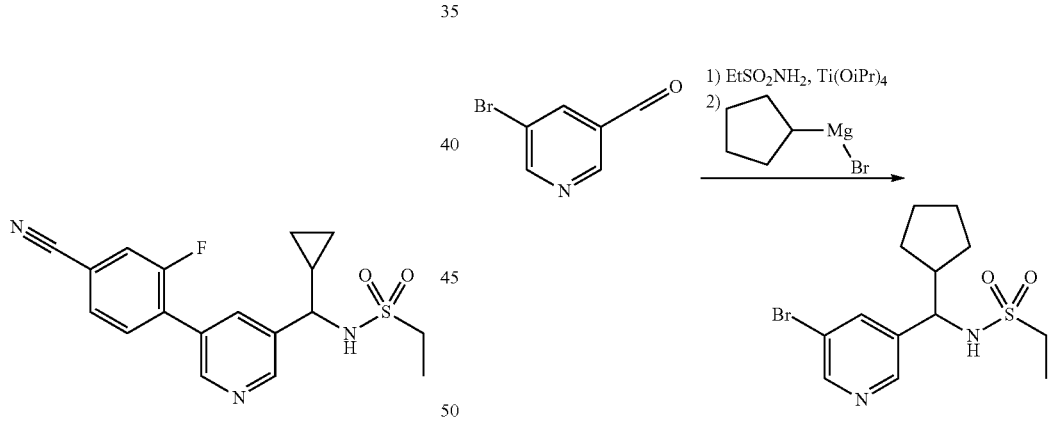

Step 1: Synthesis of N-((5-bromopyridin-3-yl)(cyclopentyl)methyl)ethanesulfonamide A mixture of 5-bromonicotinaldehyde (930 mg, 5 mmol), ethanesulfonamide (546 mg, 5.00 mmol) and titanium(IV) isopropoxide (2930 μl, 10.00 mmol) in toluene (20 mL) was heated to reflux for 4 h. After concentration, the residue was dissolved in THF (25 mL) and cooled to −40° C. A solution of cyclopentylmagnesium bromide (2M in THF, 6.25 mL, 12.5 mmol) was added dropwise and the resulting mixture was slowly warmed up to 0° C. over 4 h. The reaction was quenched with a saturated NH$_4$Cl solution. The mixture was filtered, separated, and extracted with CH$_2$Cl$_2$. The organic pahse was dried over Na$_2$SO$_4$, filtered and concentrated, and the residue was purified by flash column (ethyl acetate/heptane, v/v, 10%-30%) to give a yellow oil (480 mg). ESI-MS m/z: 348.9 [M+1]$^+$; $^1$H NMR (400 MHz, CDCl$_3$): δ 1.13-1.80 (m, 7H), 1.26 (t, J=7.4 Hz, 3H), 1.97-2.05 (m, 1H), 2.20-2.29

(m, 1H), 2.67-2.92 (m, 2H), 4.27 (t, J=8.8 Hz, 1H), 5.59 (brs, 1H), 7.87 (s, 1H), 8.56 (s, 1H), 8.68 (s, 1H).

Step 2: Synthesis of N-((5-(3-chloro-4-cyanophenyl)pyridin-3-yl)(cyclopentyl)methyl)ethanesulfonamide

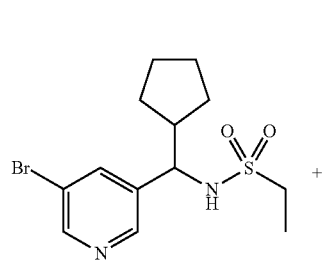 + 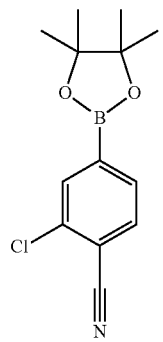 →

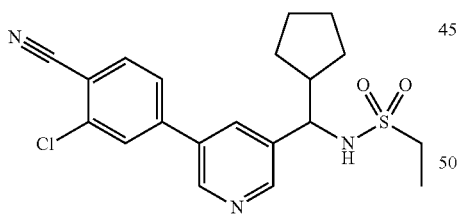

A mixture of 2-chloro-4-(4,4,5,5-tetramethyl-[1,3,2]dioxaborolan-2-yl)-benzonitrile (205 mg, 0.77 mmol), N-((5-bromopyridin-3-yl)(cyclopentyl)methyl)ethane-sulfonamide (270 mg, 0.77 mmol), PdCl$_2$(PPh$_3$)$_2$ (45 mg, 0.06 mmol) and Na$_2$CO$_3$ (2 M in water, 0.97 mL, 1.94 mmol) in DMF (4 mL) was heated at 100° C. for 2 h. The solvent was removed in vacuo. The residue was dissolved in DCM and filtered. The DCM layer was concentrated and purified by flash column (EtOAc/Heptane, v/v, 0-50%) to give the title compound (104 mg, 33%); ESI-MS m/z: 404 [M+1]$^+$; $^1$HNMR (MeOD, 400 MHz) δ 8.80 (1H, d, J=2.0 Hz), 8.61 (1H, d, J=2.0 Hz), 8.15 (1H, t, J=2.0 Hz), 8.01 (1H, d, J=1.6 Hz), 7.94 (1H, d, J=8.0 Hz), 7.82 (1H, dd, J=8.0, 1.6 Hz), 4.29 (1H, d, J=10 Hz), 2.92-2.72 (2H, m), 2.34-2.27 (1H, m), 2.03-1.97 (1H, m), 1.77-1.53 (6H, m), 1.38-1.28 (1H, m), 1.15 (1H, t, J=7.2 Hz).

Example 36

N-((5-(3-chloro-4-cyanophenyl)pyridin-3-yl)(cyclopropyl)methyl)propane-2-sulfonamide

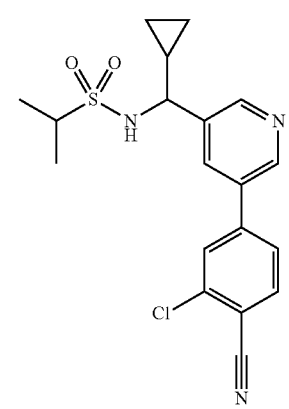 [SMILES: CC(C)S(=O)(=O)NC(c1cncc(-c2ccc(C#N)c(Cl)c2)c1)C1CC1]

Step 1: synthesis of N-((5-bromopyridin-3-yl)(cyclopropyl)methyl)propane-2-sulfonamide

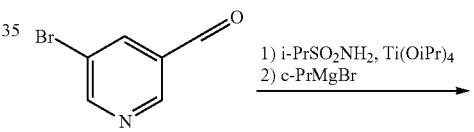

1) i-PrSO$_2$NH$_2$, Ti(OiPr)$_4$
2) c-PrMgBr

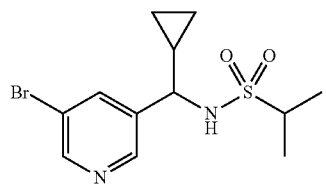

A mixture of 5-bromonicotinaldehyde (0.930 g, 5 mmol), propane-2-sulfonamide (0.616 g, 5.00 mmol) and titanium (IV) isopropoxide (2.93 mL, 10.00 mmol) in toluene (20 mL) was heated to reflux for 4 h. After concentration, the residue was dissolved in THF (25 mL) and cooled to −40° C. A solution of cyclopropylmagnesium bromide (25 mL, 12.50 mmol) was added dropwise and the resulting mixture was slowly warmed up to 0° C. over 4 h. After quenching with a NH$_4$Cl solution, filtration and extraction with CH$_2$Cl$_2$, the organic phase was dried over Na$_2$SO$_4$, filtered and concentrated, to give a residue which was purified by flash column (ethyl acetate/heptane, v/v, 10%-35%) and to give a yellow solid (1.1 g). ESI-MS m/z: 335.0 [M+1]⁺.

Step 2: Synthesis of N-((5-(3-chloro-4-cyanophenyl)pyridin-3-yl)(cyclopropyl)methyl)-propane-2-sulfonamide

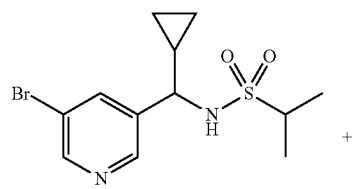

+

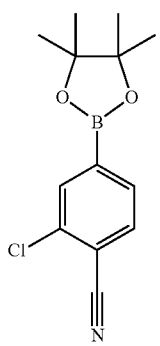

A mixture of 2-chloro-4-(4,4,5,5-tetramethyl-[1,3,2]dioxaborolan-2-yl)-benzonitrile (198 mg, 0.75 mmol), N-((5-bromopyridin-3-yl)(cyclopropyl)methyl)propane-2-sulfonamide (250 mg, 0.75 mmol), PdCl₂(PPh₃)₂ (43 mg, 0.06 mmol) and Na₂CO₃ (2 M in water, 0.94 mL, 1.88 mmol) in DMF (6 mL) was heated at 100° C. for 2 h. After concentration, the resulting residue was dissolved in DCM and filtered. The filtrates were concentrated and purified by flash column (EtOAc/Heptane, v/v, 0-40%) to give the title compound (195 mg, 67%); ESI-MS m/z: 390 [M+1]⁺; ¹H-NMR (MeOD, 400 MHz) δ 8.84 (1H, s), 8.71 (1H, s), 8.25 (1H, s), 8.05 (1H, bs), 7.98 (1H, d, J=8.0 Hz), 7.86 (1H, d, J=8.0 Hz), 3.97 (1H, d, J=9.2 Hz), 3.16-3.09 (1H, m), 1.37-1.33 (1H, m), 1.36 (3H, d, J=7.2 Hz), 1.29 (3H, d, J=7.2 Hz), 0.81-0.76 (1H, m), 0.66-0.63 (2H, m), 0.53-0.48 (1H, m); Enantiomers were separated by chiral HPLC (ChiralPak IA-H, EtOH/Heptane, v/v, 60/40) to give the first peak (enantiomer 1, t=10.11 min) and the second peak (enantiomer 2, t=12.95 min).

Example 37

N-(cyclopropyl(5-(2-methoxyphenyl)pyridin-3-yl)methyl)ethanesulfonamide

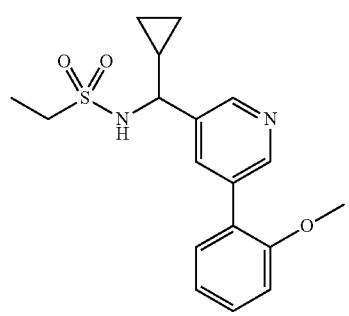

A mixture of 3-methoxyphenylboronic acid (48 mg, 0.31 mmol), N-((5-bromopyridin-3-yl)(cyclopropyl)methyl)ethanesulfonamide (100 mg, 0.31 mmol), PdCl₂(PPh₃)₂ (18 mg, 0.02 mmol) and Na₂CO₃ (2 M in water, 0.39 mL, 0.78 mmol) in DMF (2 mL) was heated at 100° C. for 2 h. After concentration, the resulting residue was dissolved in DCM and filtered. The filtrates were concentrated and purified by flash column (EtOAc/Heptane, v/v, 0-40%) to give the title compound (38 mg, 35%); ESI-MS m/z: 347 [M+1]⁺. ¹H-NMR (MeOD, 400 MHz) δ 8.75 (1H, bs), 8.61 (1H, bs), 8.17 (1H, bs), 7.46 (1H, t, J=8.0 Hz), 7.27 (1H, dd, J=8.0, 2.4 Hz), 7.24 (1H, t, J=2.4 Hz), 7.05 (1H, dd, J=8.0, 2.4 Hz), 3.94 (1H, d, J=9.2 Hz), 3.91 (3H, s), 3.03-2.89 (2H, m), 1.35-1.29

(1H, m), 1.29 (3H, t, J=7.2 Hz), 0.81-0.75 (1H, m), 0.676-0.60 (2H, m), 0.53-0.48 (1H, m)

Example 38

N-((5-(2-chlorophenyl)pyridin-3-yl)(cyclopropyl)methyl)ethanesulfonamide

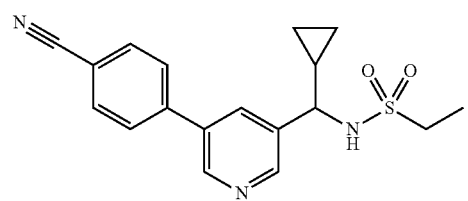 [SMILES: CCS(=O)(=O)NC(c1cncc(-c2ccc(C#N)cc2)c1)C1CC1]

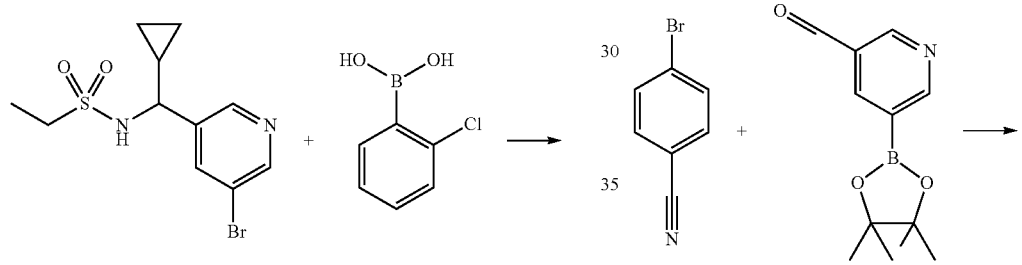

A mixture of 2-chlorophenylboronic acid (24 mg, 0.16 mmol), N-((5-bromopyridin-3-yl)(cyclopropyl)methyl)ethanesulfonamide (50 mg, 0.16 mmol), PdCl$_2$(PPh$_3$)$_2$ (9 mg, 0.01 mmol) and Na$_2$CO$_3$ (2 M in water, 0.16 mL, 0.32 mmol) in DMF (1.5 mL) was heated at 100° C. for 2 h. After concentration, the residue was dissolved in DCM and filtered. The filtrates were concentrated and purified by flash column (EtOAc/Heptane, v/v, 0-40%) to give the title compound (12 mg, 23%); ESI-MS m/z: 351 [M+1]$^+$, $^1$H-NMR (MeOD, 400 MHz) δ 8.65 (1H, d, J=2.0 Hz), 8.55 (1H, d, J=2.0 Hz), 8.04 (1H, t, J=2.0 Hz), 7.61-7.58 (1H, m), 7.48-7.44 (3H, m), 4.29

(1H, d, J=8.8 Hz), 3.02-2.89 (2H, m), 1.34-1.28 (1H, m), 1.28 (1H, t, J=7.2 Hz), 0.80-0.75 (1H, m), 0.67-0.60 (2H, m), 0.51-0.47 (1H, m)

Example 39

N-((5-(4-cyanophenyl)pyridin-3-yl)(cyclopropyl)methyl)ethanesulfonamide

Step 1: synthesis of 4-(5-formylpyridin-3-yl)benzonitrile

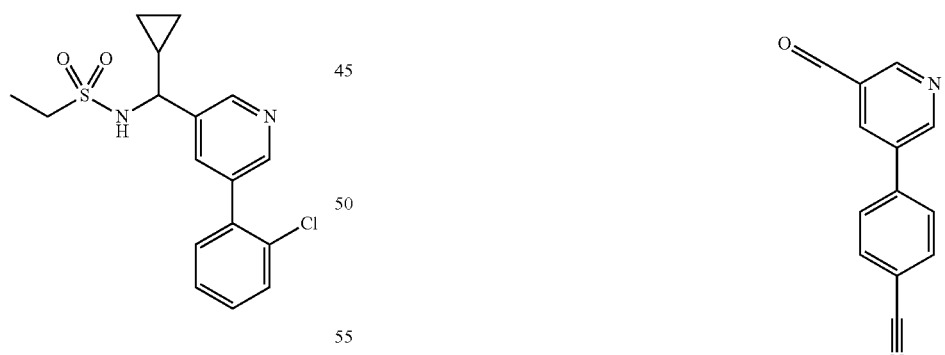

A mixture of 4-cyanophenylboronic acid (735 mg, 5.00 mmol), 5-bromonicotinaldehyde (930 mg, 5.000 mmol), sodium carbonate (5000 µl, 10.00 mmol), bis(triphenylphosphine)palladium(II) chloride (88 mg, 0.125 mmol) in DMF (15 mL, dry) was heated to 120° C. for 3 h. After concentration, the residue was dissolved into CH$_2$Cl$_2$-MeOH, mixed with silica gel and concentrated. Purification by flash column (MeOH—CH$_2$Cl$_2$, v/v, 0%-1%) yielded 4-(5-formylpyridin-3-yl)benzonitrile as colorless solid (550 mg) $^1$H NMR (400

MHz, CDCl$_3$): δ 7.55 (d, J=8.57 Hz, 2H), 7.82 (d, J=8.57 Hz, 2H), 8.36 (s, 1H), 9.08 (d, J=2 Hz, 1H), 9.12 (d, J=2 Hz, 1H), 10.21 (s, 1H).

Step 2: Synthesis of N-((5-(4-cyanophenyl)pyridin-3-yl)(cyclopropyl)methyl)ethanesulfonamide

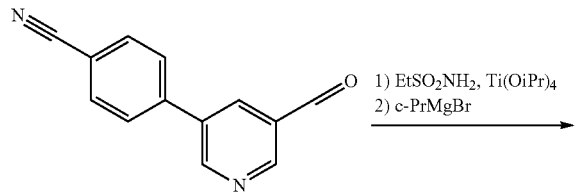

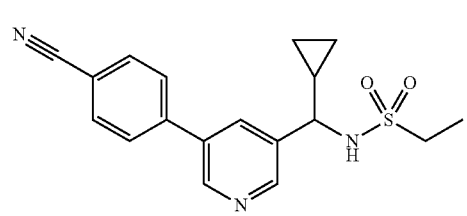

Titanium isopropoxide (0.70 mL, 2.40 mmol) was added to a mixture of 4-(5-formyl-pyridin-3-yl)-benzonitrile (250 mg, 1.20 mmol) and ethanesulfonamide (144 mg, 1.32 mmol) in toluene (10 mL) at room temperature. The resulting mixture was heated to reflux for 2 h. After concentration, the residue was dissolved in THF (10 mL) and cooled to −40° C. c-PrMgBr (0.5 M in THF, 12.0 mL, 6.00 mmol) was added dropwise and the resulting mixture was stirred at −36° C. for 1 h. Saturated NH$_4$Cl solution was then added to the reaction mixture. The resulting solution was diluted with ethyl acetate and brine. The mixture was filtered and the organic layer was separated. After concentration, the residue was purified by flash column (MeOH/DCM, v/v, 0-3%) to give N-((5-(4-cyanophenyl)pyridin-3-yl)(cyclopropyl)methyl)ethanesulfonamide (210 mg, 51%); ESI-MS m/z: 342 [M+1]$^+$, $^1$H-NMR (MeOD, 400 MHz) δ 8.83 (d, J=2.0 Hz, 1H), 8.69 (d, J=2.0 Hz, 1H), 8.24 (t, J=2.0 Hz, 1H), 7.92 (s, 4H), 3.96 (d, J=9.2 Hz, 1H), 3.06-2.93 (m, 2H), 1.35-1.31 (m, 1H), 1.31 (t, J=7.2 Hz, 3H), 0.81-0.76 (m, 1H), 0.67-0.61 (m, 2H), 0.54-0.49 (m, 1H); enantiomers were separated by chiral HPLC (Chiralpak IA-H, EtOH/Heptane, v/v, 70/30) to the first peak (enantiomer 1, t=10.20 min) and the second peak (enantiomer 2, t=15.99 min).

Example 40

N-(2-(5-(3-chloro-4-cyanophenyl)pyridin-3-yl)propan-2-yl)ethanesulfonamide

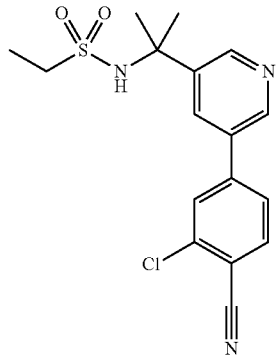 [SMILES: CCS(=O)(=O)NC(C)(C)c1cncc(-c2ccc(C#N)c(Cl)c2)c1]

Step 1: synthesis of N-(2-(5-bromopyridin-3-yl)propan-2-yl)ethanesulfonamide

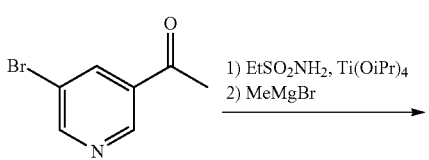

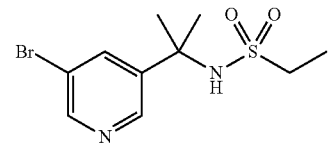

A mixture of 1-(5-bromo-pyridin-3-yl)-ethanone (200 mg, 1.000 mmol), ethanesulfonamide (136 mg, 1.250 mmol) and titanium(IV) isopropoxide (586 μL, 2.0 mmol) in toluene (20 mL) was heated to reflux for 8 h. After concentration, the residue was dissolved in THF (5 mL). A solution of methylmagnesium bromide (1000 μl, 3.00 mmol) was added dropwise at −50° C. The resulting mixture was slowly warmed up to room temperature over a course of 2 h. The mixture was stirred at this temperature overnight and quenched with NH$_4$Cl solution. After filtration, wash with CH$_2$Cl$_2$ and concentration, the residue was purified by flash column (Ethyl acetate/heptane, v/v, 10% to 50%) and yielded a yellow oil (35 mg). ESI-MS m/z: 309.1 [M+1]$^+$, Retention time=1.22 min. $^1$H NMR (400 MHz, CDCl$_3$): δ 1.43 (t, J=7.4 Hz, 3H), 1.84 (s, 6H), 2.98 (q, J=7.4 Hz, 2H), 5.07 (brs, 1H), 8.04 (s, 1H), 8.66 (s, 1H), 8.77 (s, 1H).

Step 2: Synthesis of N-(2-(5-(3-chloro-4-cyanophenyl)pyridin-3-yl)propan-2-yl)ethanesulfonamide

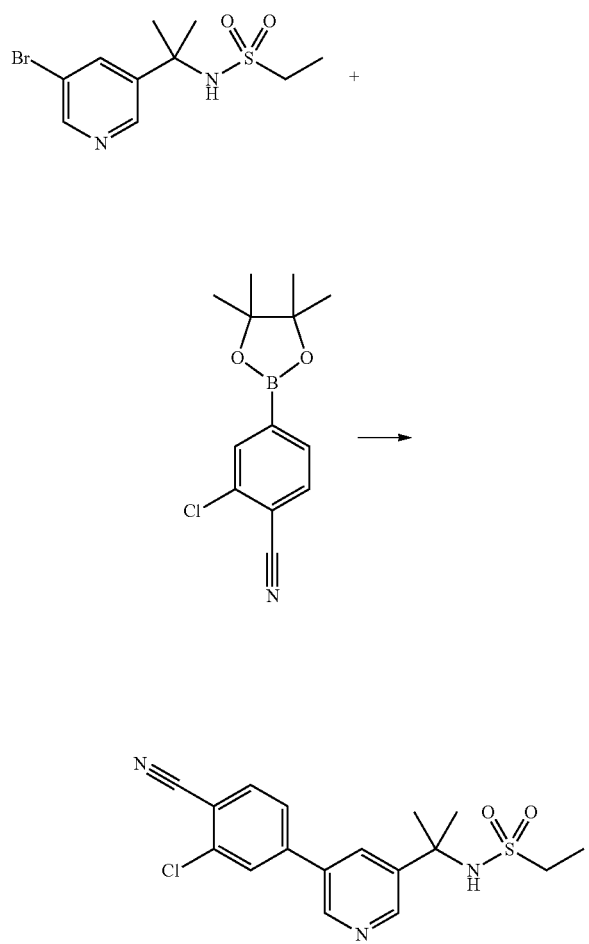

A mixture of N-(2-(5-bromopyridin-3-yl)propan-2-yl)ethanesulfonamide (30 mg, 0.098 mmol), 2-chloro-4-(4,4,5,5-tetramethyl-1,3,2-dioxaborolan-2-yl)benzonitrile (27.0 mg, 0.103 mmol), PdCl$_2$(dppf).CH$_2$Cl$_2$ adduct (1.994 mg, 2.441 µmol) and sodium carbonate (98 µl, 0.195 mmol) in DMF (10 mL) was heated to 100° C. overnight. After concentration, the residue was purified by column (MeOH—CH$_2$Cl$_2$, v/v, 10-20%) yielded the title compound as oil (1 mg). ESI-MS m/z: [M+1]$^+$ 364.0, Retention time=1.40 min. $^1$H NMR (400 MHz, CDCl$_3$): δ 1.31 (t, J=7.37 Hz, 3H), 1.76 (s, 6H), 2.86-2.91 (m, 2H), 4.54 (brs, 1H), 7.52 (dd, J=1.7, 8 Hz, 1H), 7.67 (d, J=1.6 Hz, 1H), 7.72 (d, J=8 Hz, 1H), 7.95 (t, J=2.2 Hz, 1H), 8.67 (d, J=2.2 Hz, 1H), 8.76 (d, J=2.2 Hz, 1H).

Example 41-53

General Procedure for the Suzuki Coupling Reaction Between N-((5-bromopyridin-3-yl)(cyclopropyl)methyl)ethanesulfonamide and boronic acids/esters To each microwave vial, N-((5-bromopyridin-3-yl)(cyclopropyl)methyl)ethanesulfonamide (63 µmol, 1 eq) was dissolved in DMF:H$_2$O (600 µL:100 µL). Then, Na$_2$CO$_3$ (125 µmol, 2 eq) and one boronic acid (69 µmol, 1.1 eq) were added. To the stirred mixture, Pd(PPh$_3$)$_2$C$_2$ (1.25 µmol, 0.02 eq) was added. The reaction was carried out under sealed-vessel microwave heating at 150° C. for 10 minutes using a Biotage Initiator™ (pre-stirring: 10 s, absorption level: very high). The mixture was then allowed to cool to room temperature, the Pd catalyst was filtered off. The mixture was diluted with methanol and the crude product was directly purified by preparative LC-MS (solvent 1: water 0.1% TFA, solvent 2: methanol 0.1% TFA). Isolated products were identified by LC-MS.

| example | Structure | Name ($^1$H NMR) | [M + H]$^+$ | retention time (min) |
|---|---|---|---|---|
| 41 | 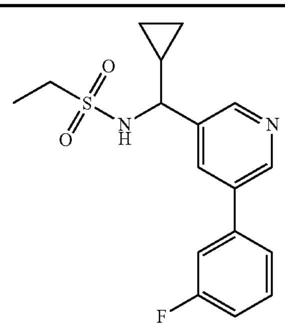 | N-(cyclopropyl(5-(3-fluorophenyl)pyridin-3-yl)methyl)ethanesulfonamide $^1$H NMR (500 MHz, DMSO-d$_6$) δ ppm 0.41-0.64 (m, 4H) 1.06 (t, J = 7.32 Hz, 3H) 1.18-1.27 (m, 1H) 2.77 (dq, J = 14.38, 7.26 Hz, 1H) 2.90 (dq, J = 14.34, 7.27 Hz, 1H) 3.86 (t, J = 8.77 Hz, 1H) 7.28 (t, J = 9.08 Hz, 1H) 7.54-7.67 (m, 3H) 7.95 (d, J = 8.70 Hz, 1H) 8.27 (s, 1H) 8.65 (d, J = 1.07 Hz, 1H) 8.88 (d, J = 1.53 Hz, 1H) | 335 | 2.09 |

-continued

| example | Structure | Name (¹H NMR) | [M + H]⁺ | retention time (min) |
|---|---|---|---|---|
| 42 | 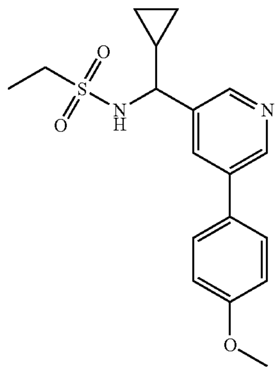 [SMILES: CCS(=O)(=O)NC(c1cncc(-c2ccc(OC)cc2)c1)C1CC1] | N-(cyclopropyl(5-(4-methoxyphenyl)pyridin-3-yl)methyl)ethanesulfonamide ¹H NMR (500 MHz, DMSO-d₆) δ ppm 0.41-0.64 (m, 4H) 1.07 (t, J = 7.32 Hz, 3H) 1.18-1.26 (m, 1H) 2.78 (dq, J = 14.32, 7.23 Hz, 1H) 2.91 (dq, J = 14.32, 7.23 Hz, 1H) 3.82 (s, 3H) 3.87 (t, J = 8.77 Hz, 1H) 7.10 (d, J = 8.85 Hz, 2H) 7.69-7.74 (m, 2H) 7.98 (d, J = 8.70 Hz, 1H) 8.28 (br. s., 1H) 8.59 (d, J = 1.53 Hz, 1H) 8.84 (d, J = 1.53 Hz, 1H) | 347 | 1.93 |
| 43 | 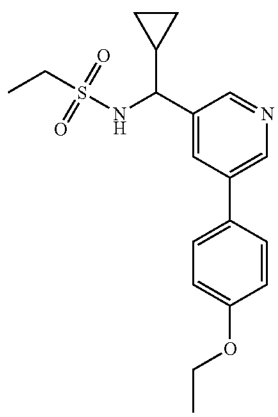 [SMILES: CCOc1ccc(-c2cncc(C(NS(=O)(=O)CC)C3CC3)c2)cc1] | N-(cyclopropyl(5-(4-ethoxyphenyl)pyridin-3-yl)methyl)ethanesulfonamide ¹H NMR (500 MHz, DMSO-d₆) δ ppm 0.42-0.65 (m, 4H) 1.07 (t, J = 7.25 Hz, 3H) 1.18-1.28 (m, 1H) 1.35 (t, J = 6.94 Hz, 3H) 2.78 (dq, J = 14.31, 7.18 Hz, 1H) 2.91 (dq, J = 14.32, 7.23 Hz, 1H) 3.87 (t, J = 8.70 Hz, 1H) 4.09 (q, J = 6.97 Hz, 2H) 7.08 (d, J = 8.70 Hz, 2H) 7.71 (d, J = 8.70 Hz, 2H) 7.98 (d, J = 8.54 Hz, 1H) 8.30 (br. s., 1H) 8.59 (s, 1H) 8.85 (d, J = 1.22 Hz, 1H) | 361 | 2.17 |
| 44 | 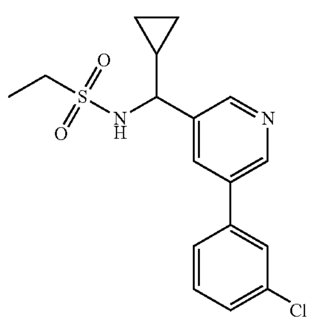 [SMILES: CCS(=O)(=O)NC(c1cncc(-c2cccc(Cl)c2)c1)C1CC1] | N-((5-(3-chlorophenyl)pyridin-3-yl)(cyclopropyl)methyl)-ethanesulfonamide ¹H NMR (500 MHz, DMSO-d₆) δ ppm 0.40-0.64 (m, 4H) 1.06 (t, J = 7.32 Hz, 3H) 1.18-1.28 (m, 1H) 2.78 (dq, J = 14.32, 7.23 Hz, 1H) 2.90 (dq, J = 14.32, 7.23 Hz, 1H) 3.87 (t, J = 8.77 Hz, 1H) 7.49-7.59 (m, 2H) 7.74 (d, J = 7.63 Hz, 1H) 7.85 (s, 1H) 7.96 (d, J = 8.70 Hz, 1H) 8.30 (s, 1H) 8.66 (d, J = 1.83 Hz, 1H) 8.89 (d, J = 1.98 Hz, 1H) | 351 | 2.30 |
| 45 | 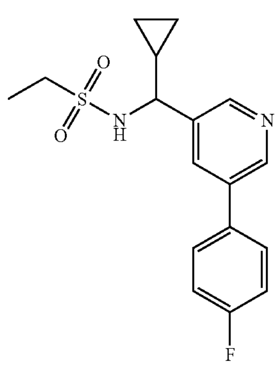 [SMILES: CCS(=O)(=O)NC(c1cncc(-c2ccc(F)cc2)c1)C1CC1] | N-(cyclopropyl(5-(4-fluorophenyl)pyridin-3-yl)methyl)ethanesulfonamide ¹H NMR (500 MHz, DMSO-d₆) δ ppm 0.40-0.65 (m, 4H) 1.06 (t, J = 7.32 Hz, 3H) 1.17-1.26 (m, 1H) 2.77 (dq, J = 14.38, 7.26 Hz, 1H) 2.90 (dq, J = 14.34, 7.27 Hz, 1H) 3.85 (t, J = 8.70 Hz, 1H) 7.37 (t, J = 8.85 Hz, 2H) 7.76-7.83 (m, 2H) 7.96 (d, J = 8.70 Hz, 1H) 8.21 (s, 1H) 8.62 (d, J = 1.83 Hz, 1H) 8.82 (d, J = 1.98 Hz, 1H) | 335 | 2.04 |

-continued

| example | Structure | Name (¹H NMR) | [M + H]⁺ | retention time (min) |
|---|---|---|---|---|
| 46 | 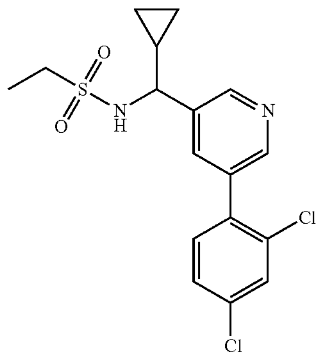 [SMILES: CCS(=O)(=O)NC(c1cncc(-c2ccc(Cl)cc2Cl)c1)C1CC1] | N-(cyclopropyl(5-(2,4-dichlorophenyl)pyridin-3-yl)methyl)ethanesulfonamide ¹H NMR (500 MHz, DMSO-d₆) δ ppm 0.40-0.64 (m, 4H) 1.07 (t, J = 7.32 Hz, 3H) 1.15-1.25 (m, 1H) 2.78 (dq, J = 14.34, 7.27 Hz, 1H) 2.90 (dq, J = 14.34, 7.27 Hz, 1H) 3.85 (t, J = 8.70 Hz, 1H) 7.51-7.54 (m, 1H) 7.59 (dd, J = 8.24, 2.14 Hz, 1H) 7.81 (d, J = 1.98 Hz, 1H) 7.97 (s, 1H) 7.97-8.01 (m, 1H) 8.57 (d, J = 1.98 Hz, 1H) 8.67 (d, J = 1.98 Hz, 1H) | 385 | 2.52 |
| 47 | 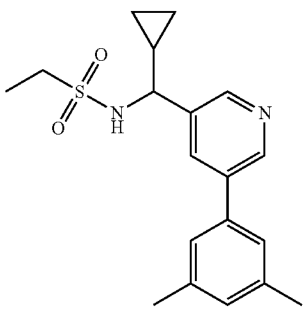 [SMILES: CCS(=O)(=O)NC(c1cncc(-c2cc(C)cc(C)c2)c1)C1CC1] | N-(cyclopropyl(5-(3,5-dimethylphenyl)pyridin-3-yl)methyl)ethanesulfonamide ¹H NMR (500 MHz, DMSO-d₆) δ ppm 0.39-0.65 (m, 4H) 1.07 (t, J = 7.32 Hz, 3H) 1.17-1.26 (m, 1H) 2.35 (s, 6H) 2.77 (dq, J = 14.34, 7.27 Hz, 1H) 2.90 (dq, J = 14.34, 7.27 Hz, 1H) 3.85 (t, J = 8.70 Hz, 1H) 7.08 (s, 1H) 7.36 (s, 2H) 7.98 (d, J = 8.55 Hz, 1H) 8.22 (br. s., 1H) 8.60 (d, J = 1.37 Hz, 1H) 8.81 (d, J = 1.53 Hz, 1H) | 345 | 2.41 |
| 48 | 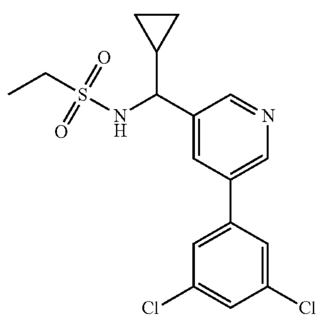 [SMILES: CCS(=O)(=O)NC(c1cncc(-c2cc(Cl)cc(Cl)c2)c1)C1CC1] | N-(cyclopropyl(5-(3,5-dichlorophenyl)pyridin-3-yl)methyl)ethanesulfonamide ¹H NMR (500 MHz, DMSO-d₆) δ ppm 0.39-0.64 (m, 4H) 1.05 (t, J = 7.32 Hz, 3H) 1.18-1.29 (m, 1H) 2.77 (dq, J = 14.32, 7.23 Hz, 1H) 2.89 (dq, J = 14.32, 7.20 Hz, 1H) 3.85 (t, J = 8.70 Hz, 1H) 7.69 (d, J = 1.53 Hz, 1H) 7.87 (d, J = 1.68 Hz, 2H) 7.93 (d, J = 8.85 Hz, 1H) 8.30 (s, 1H) 8.67 (d, J = 1.68 Hz, 1H) 8.91 (d, J = 1.83 Hz, 1H) | 385 | 2.64 |
| 49 | 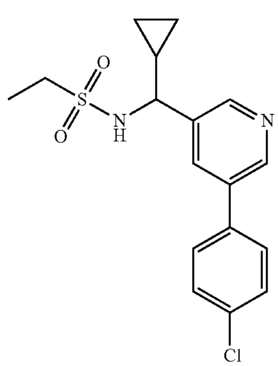 [SMILES: CCS(=O)(=O)NC(c1cncc(-c2ccc(Cl)cc2)c1)C1CC1] | N-((5-(4-chlorophenyl)pyridin-3-yl)(cyclopropyl)methyl)-ethanesulfonamide ¹H NMR (500 MHz, DMSO-d₆) δ ppm 0.41-0.64 (m, 4H) 1.06 (t, J = 7.32 Hz, 3H) 1.17-1.26 (m, 1H) 2.77 (dq, J = 14.32, 7.23 Hz, 1H) 2.90 (dq, J = 14.40, 7.25 Hz, 1H) 3.85 (t, J = 8.70 Hz, 1H) 7.60 (d, J = 8.54 Hz, 2H) 7.78 (d, J = 8.55 Hz, 2H) 7.96 (d, J = 8.70 Hz, 1H) 8.23 (s, 1H) 8.63 (d, J = 1.68 Hz, 1H) 8.84 (d, J = 1.98 Hz, 1H) | 351 | 2.30 |

-continued

| example | Structure | Name (¹H NMR) | [M + H]⁺ | retention time (min) |
|---|---|---|---|---|
| 50 | 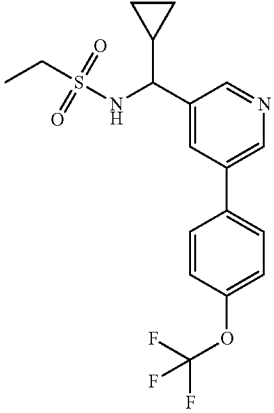 [SMILES: CCS(=O)(=O)NC(c1cncc(-c2ccc(OC(F)(F)F)cc2)c1)C1CC1] | N-(cyclopropyl(5-(4-(trifluoromethoxy)phenyl)pyridin-3-yl)methyl)ethanesulfonamide ¹H NMR (500 MHz, DMSO-d$_6$) δ ppm 0.41-0.65 (m, 4H) 1.07 (t, J = 7.32 Hz, 3H) 1.17-1.26 (m, 1H) 2.78 (dq, J = 14.31, 7.32, 7.21 Hz, 1H) 2.90 (dq, J = 14.34, 7.27 Hz, 1H) 3.86 (t, J = 8.70 Hz, 1H) 7.54 (d, J = 8.24 Hz, 2H) 7.88 (d, J = 8.85 Hz, 2H) 7.97 (d, J = 8.54 Hz, 1H) 8.24 (s, 1H) 8.65 (d, J = 1.83 Hz, 1H) 8.85 (d, J = 2.14 Hz, 1H) | 401 | 2.51 |
| 51 | 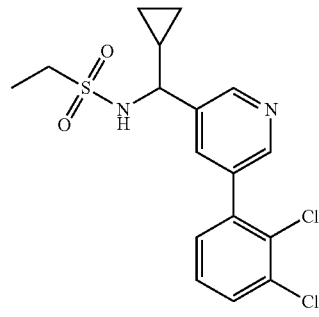 [SMILES: CCS(=O)(=O)NC(c1cncc(-c2cccc(Cl)c2Cl)c1)C1CC1] | N-(cyclopropyl(5-(2,3-dichlorophenyl)pyridin-3-yl)methyl)ethanesulfonamide ¹H NMR (500 MHz, DMSO-d$_6$) δ ppm 0.40-0.64 (m, 4H) 1.07 (t, J = 7.32 Hz, 3H) 1.15-1.24 (m, 1H) 2.73-2.82 (m, 1H) 2.86-2.95 (m, 1H) 3.86 (t, J = 8.70 Hz, 1H) 7.43-7.54 (m, 2H) 7.75 (dd, J = 7.86, 1.60 Hz, 1H) 7.96 (d, J = 8.54 Hz, 1H) 8.01 (s, 1H) 8.58 (d, J = 2.14 Hz, 1H) 8.69 (d, J = 1.83 Hz, 1H) | 385 | 2.44 |
| 52 | 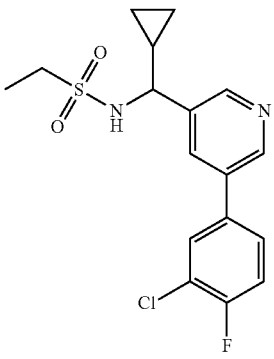 [SMILES: CCS(=O)(=O)NC(c1cncc(-c2ccc(F)c(Cl)c2)c1)C1CC1] | N-((5-(3-chloro-4-fluorophenyl)pyridin-3-yl)(cyclopropyl)methyl)-ethanesulfonamide ¹H NMR (500 MHz, DMSO-d$_6$) δ ppm 0.41-0.64 (m, 4H) 1.05 (t, J = 7.32 Hz, 3H) 1.18-1.28 (m, 1H) 2.77 (dq, J = 14.34, 7.27 Hz, 1H) 2.89 (dq, J = 14.34, 7.27 Hz, 1H) 3.85 (t, J = 8.77 Hz, 1H) 7.59 (t, J = 8.93 Hz, 1H) 7.79 (ddd, J = 8.62, 4.65, 2.29 Hz, 1H) 7.93 (d, J = 8.85 Hz, 1H) 8.02 (dd, J = 7.02, 2.29 Hz, 1H) 8.25 (s, 1H) 8.64 (d, J = 1.98 Hz, 1H) 8.86 (d, J = 2.14 Hz, 1H) | 369 | 2.36 |
| 53 | 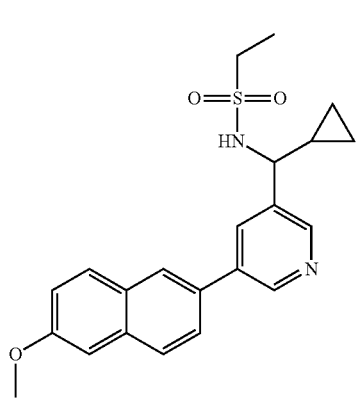 [SMILES: CCS(=O)(=O)NC(c1cncc(-c2ccc3cc(OC)ccc3c2)c1)C1CC1] | N-(cyclopropyl(5-(6-methoxynaphthalen-2-yl)pyridin-3-yl)methyl)ethanesulfonamide ¹HNMR (500 MHz, DMSO-d6) δ ppm 0.44-0.67 (m, 4H), 1.09 (t, J = 7.32 Hz, 3H), 1.22-1.31 (m, 1H), 2.77-2.98 (m, 2H), 3.90 (s, 3H), 3.91-3.94 (m, 1H), 7.24 (dd, J = 8.85, 2.24 Hz, 1H), 7.40 (d, J = 2.29 Hz, 1H), 7.88 (dd, J = 8.55, 1.68 Hz, 1H),7.93 (d, J = 9.00 Hz, 1H), 7.99 (d, J = 8.70 Hz, 1H), 8.28 (s, 1H), 8.47 (br.s, 1H), 8.67 (d, J = 1.53 Hz, 1h), 9.02 (d, J = 1.83 Hz, 1H) | 397 | 2.71 |

| example | Structure | Name (¹H NMR) | [M + H]⁺ | retention time (min) |
|---|---|---|---|---|
| 54 | 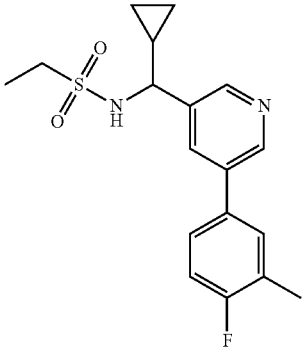 [SMILES: CCS(=O)(=O)NC(c1cncc(-c2ccc(F)c(C)c2)c1)C1CC1] | N-(cyclopropyl(5-(4-fluoro-3-methyl-phenyl)pyridin-3-yl)methyl)ethanesulfonamide ¹H NMR (500 MHz, DMSO-d₆) δ ppm 0.40-0.65 (m, 4H) 1.07 (t, J = 7.32 Hz, 3H) 1.18-1.27 (m, 1H) 2.32 (s, 3H) 2.78 (dq, J = 14.38, 7.21 Hz, 1H) 2.90 (dq, J = 14.40, 7.25 Hz, 1H) 3.86 (t, J = 8.70 Hz, 1H) 7.30 (t, J = 9.08 Hz, 1H) 7.58-7.64 (m, 1H) 7.70 (dd, J = 7.25, 1.75 Hz, 1H) 7.97 (d, J = 8.70 Hz, 1H) 8.26 (s, 1H) 8.63 (d, J = 1.68 Hz, 1H) 8.84 (d, J = 1.98 Hz, 1H) | 349 | 2.13 |
| 55 | 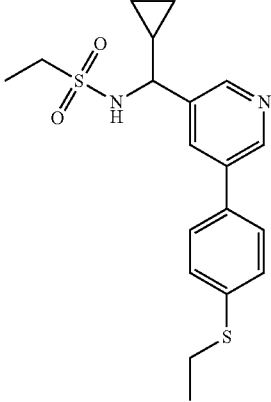 [SMILES: CCSc1ccc(-c2cncc(C(NS(=O)(=O)CC)C3CC3)c2)cc1] | N-(cyclopropyl(5-(4-ethylsulfanyl-phenyl)pyridin-3-yl)methyl)ethanesulfonamide ¹H NMR (500 MHz, DMSO-d₆) δ ppm 0.41-0.65 (m, 4H) 1.07 (t, J = 7.32 Hz, 3H) 1.18-1.24 (m, 1H) 1.27 (t, J = 7.32 Hz, 3H) 2.78 (dq, J = 14.38, 7.26 Hz, 1H) 2.91 (dq, J = 14.32, 7.23 Hz, 1H) 3.05 (q, J = 7.32 Hz, 2H) 3.87 (t, J = 8.70 Hz, 1H) 7.45 (d, J = 8.39 Hz, 2H) 7.71 (d, J = 8.39 Hz, 2H) 7.98 (d, J = 8.70 Hz, 1H) 8.27 (br. s., 1H) 8.62 (d, J = 1.68 Hz, 1H) 8.85 (d, J = 1.83 Hz, 1H) | 377 | 2.32 |
| 56 | 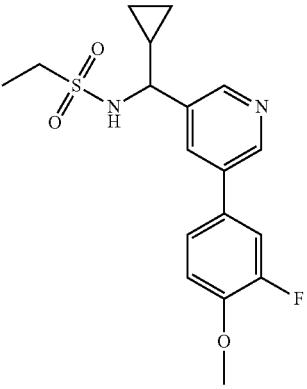 [SMILES: CCS(=O)(=O)NC(c1cncc(-c2ccc(OC)c(F)c2)c1)C1CC1] | N-(cyclopropyl(5-(3-fluoro-4-methoxy-phenyl)pyridin-3-yl)methyl)ethanesulfonamide ¹H NMR (500 MHz, DMSO-d₆) δ ppm 0.41-0.64 (m, 4H) 1.06 (t, J = 7.32 Hz, 3H) 1.17-1.26 (m, 1H) 2.77 (dq, J = 14.34, 7.27 Hz, 1H) 2.90 (dq, J = 14.20, 7.20 Hz, 1H) 3.86 (t, J = 8.77 Hz, 1H) 3.90 (s, 3H) 7.32 (t, J = 8.85 Hz, 1H) 7.58 (d, J = 8.85 Hz, 1H) 7.70 (dd, J = 12.74, 2.06 Hz, 1H) 7.95 (d, J = 8.85 Hz, 1H) 8.28 (br. s., 1H) 8.60 (d, J = 1.68 Hz, 1H) 8.86 (d, J = 1.83 Hz, 1H) | 365 | 1.89 |

-continued

| example | Structure | Name (¹H NMR) | [M + H]⁺ | retention time (min) |
|---|---|---|---|---|
| 57 | 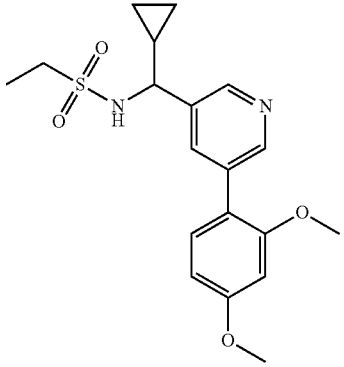 [SMILES: CCS(=O)(=O)NC(c1cncc(-c2ccc(OC)cc2OC)c1)C1CC1] | N-(cyclopropyl(5-(2,4-dimethoxy-phenyl)pyridin-3-yl)methyl)ethanesulfonamide ¹H NMR (500 MHz, DMSO-d₆) δ ppm 0.41-0.65 (m, 4H) 1.10 (t, J = 7.32 Hz, 3H) 1.16-1.25 (m, 1H) 2.81 (dq, J = 14.34, 7.27 Hz, 1H) 2.93 (dq, J = 14.34, 7.27 Hz, 1H) 3.80 (s, 3H) 3.82 (s, 3H) 3.88 (t, J = 8.62 Hz, 1H) 6.69 (dd, J = 8.39, 2.29 Hz, 1H) 6.72 (d, J = 2.29 Hz, 1H) 7.35 (d, J = 8.39 Hz, 1H) 8.01 (d, J = 8.39 Hz, 1H) 8.20 (br. s., 1H) 8.58 (d, J = 1.53 Hz, 1H) 8.68 (s, 1H) | 377 | 1.75 |
| 58 | 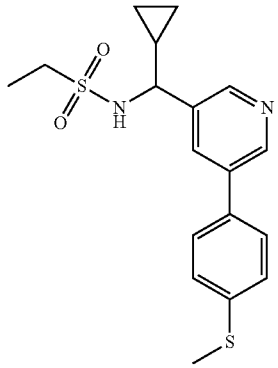 [SMILES: CCS(=O)(=O)NC(c1cncc(-c2ccc(SC)cc2)c1)C1CC1] | N-(cyclopropyl(5-(4-methylsulfanyl-phenyl)pyridin-3-yl)methyl)ethanesulfonamide ¹H NMR (500 MHz, DMSO-d₆) δ ppm 0.39-0.66 (m, 4H) 1.07 (t, J = 7.25 Hz, 3H) 1.16-1.27 (m, 1H) 2.52 (s, 3H) 2.71-2.82 (m, 1H) 2.90 (dq, J = 14.38, 7.26 Hz, 1H) 3.85 (t, J = 8.70 Hz, 1H) 7.41 (d, J = 8.39 Hz, 2H) 7.71 (d, J = 8.39 Hz, 2H) 7.97 (d, J = 8.70 Hz, 1H) 8.24 (br. s., 1H) 8.60 (d, J = 1.68 Hz, 1H) 8.83 (d, J = 1.68 Hz, 1H) | 363 | 2.30 |
| 59 | 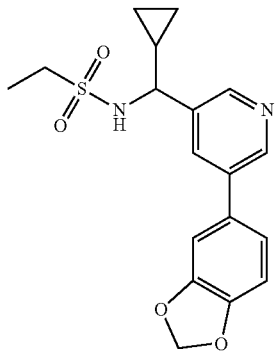 [SMILES: CCS(=O)(=O)NC(c1cncc(-c2ccc3c(c2)OCO3)c1)C1CC1] | N-(cyclopropyl(5-benzo-[1,3]-dioxol-5-yl-pyridin-3-yl)methyl)ethanesulfonamide ¹H NMR (500 MHz, DMSO-d₆) δ ppm 0.39-0.63 (m, 4H) 1.05 (t, J = 7.25 Hz, 3H) 1.17-1.24 (m, 1H) 2.75 (dq, J = 14.36, 7.32 Hz, 1H) 2.88 (dq, J = 14.34, 7.27 Hz, 1H) 3.83 (t, J = 8.70 Hz, 1H) 6.09 (s, 2H) 7.07 (d, J = 8.09 Hz, 1H) 7.22-7.26 (m, 1H) 7.35 (d, J = 1.68 Hz, 1H) 7.93 (d, 1H) 8.15 (br. s., 1H) 8.55 (d, J = 1.68 Hz, 1H) 8.77 (d, J = 1.83 Hz, 1H) | 361 | 1.95 |
| 60 | 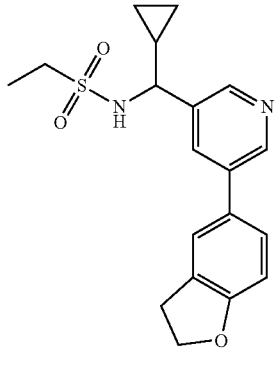 [SMILES: CCS(=O)(=O)NC(c1cncc(-c2ccc3c(c2)CCO3)c1)C1CC1] | N-(cyclopropyl(5-(2,3-dihydro-benzofuran-5-yl)pyridin-3-yl)methyl)ethanesulfonamide ¹H NMR (500 MHz, DMSO-d₆) δ ppm 0.42-0.65 (m, 4H) 1.07 (t, J = 7.32 Hz, 3H) 1.18-1.27 (m, 1H) 2.79 (dq, J = 14.38, 7.26 Hz, 1H) 2.91 (dq, J = 14.38, 7.26 Hz, 1H) 3.26 (t, J = 8.70 Hz, 2H) 3.87 (t, 1H) 4.60 (t, J = 8.70 Hz, 2H) 6.92 (d, J = 8.24 Hz, 1H) 7.49-7.54 (m, 1H) 7.66 (s, 1H) 7.98 (d, J = 8.55 Hz, 1H) 8.31 (br. s., 1H) 8.59 (d, J = 1.37 Hz, 1H) 8.83 (d, J = 1.68 Hz, 1H) | 359 | 1.94 |

-continued

| example | Structure | Name (¹H NMR) | [M + H]⁺ | retention time (min) |
|---|---|---|---|---|
| 61 | 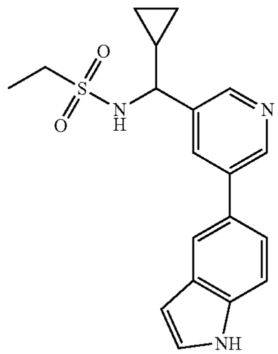 [SMILES: CCS(=O)(=O)NC(c1cncc(-c2ccc3[nH]ccc3c2)c1)C1CC1] | N-(cyclopropyl(5-(1H-indol-5-yl)pyridin-3-yl)methyl)ethanesulfonamide ¹H NMR (500 MHz, DMSO-d₆) δ ppm 0.43-0.67 (m, 4H) 1.10 (t, J = 7.25 Hz, 3H) 1.21-1.29 (m, 1H) 2.82 (dq, J = 14.32, 7.13 Hz, 1H) 2.94 (dq, J = 14.30, 7.20 Hz, 1H) 3.92 (t, J = 8.62 Hz, 1H) 6.54 (br. s., 1H) 7.43 (t, J = 2.59 Hz, 1H) 7.48-7.52 (m, 1H) 7.53-7.57 (m, 1H) 7.97 (s, 1H) 8.03 (d, J = 8.55 Hz, 1H) 8.46 (br. s., 1H) 8.61 (s, 1H) 8.94 (s, 1H) 11.28 (br. s., 1H) | 356 | 1.27 |
| 62 | 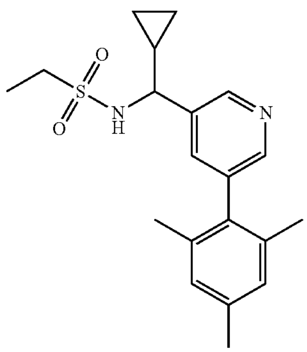 [SMILES: CCS(=O)(=O)NC(c1cncc(-c2c(C)cc(C)cc2C)c1)C1CC1] | N-(cyclopropyl(5-(2,4,6-trimethyl-phenyl)pyridin-3-yl)methyl)ethanesulfonamide ¹H NMR (500 MHz, DMSO-d₆) δ ppm 0.37-0.63 (m, 4H) 1.04 (t, J = 7.25 Hz, 3H) 1.15-1.24 (m, 1H) 1.93 (d, J = 5.34 Hz, 6H) 2.21 (s, 3H) 2.73 (dq, J = 14.40, 7.25 Hz, 1H) 2.87 (dq, J = 14.42, 7.30 Hz, 1H) 3.85 (t, J = 8.62 Hz, 1H) 6.97 (s, 2H) 7.69 (br. s., 1H) 7.92 (d, J = 8.70 Hz, 1H) 8.28 (d, J = 1.07 Hz, 1H) 8.61 (d, J = 1.68 Hz, 1H) | 359 | 2.56 |
| 63 | 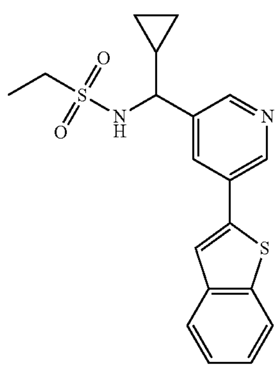 [SMILES: CCS(=O)(=O)NC(c1cncc(-c2cc3ccccc3s2)c1)C1CC1] | N-(cyclopropyl(5-benzo[b]thiophen-2-yl-pyridin-3-yl)methyl)ethanesulfonamide ¹H NMR (500 MHz, DMSO-d₆) δ ppm 0.42-0.66 (m, 4H) 1.10 (t, J = 7.32 Hz, 3H) 1.18-1.27 (m, 1H) 2.79 (dq, J = 14.32, 7.23 Hz, 1H) 2.93 (dq, J = 14.34, 7.27 Hz, 1H) 3.87 (t, 1H) 7.38-7.45 (m, J = 7.15, 7.15, 7.15, 7.15, 1.30 Hz, 2H) 7.88-7.92 (m, 1H) 8.00 (s, 1H) 8.03 (d, J = 8.39 Hz, 2H) 8.26 (s, 1H) 8.61 (d, J = 1.83 Hz, 1H) 8.94 (d, J = 2.14 Hz, 1H) | 373 | 2.59 |
| 64 | 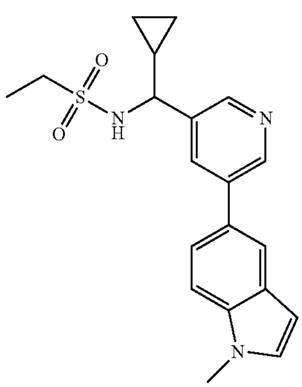 [SMILES: CCS(=O)(=O)NC(c1cncc(-c2ccc3c(ccn3C)c2)c1)C1CC1] | N-(cyclopropyl(5-(1-methyl-1H-indol-5-yl)pyridin-3-yl)methyl)ethanesulfonamide ¹H NMR (500 MHz, DMSO-d₆) δ ppm 0.44-0.66 (m, 4H) 1.09 (t, J = 7.32 Hz, 3H) 1.20-1.30 (m, 1H) 2.81 (dq, J = 14.34, 7.27 Hz, 1H) 2.93 (dq, J = 14.34, 7.27 Hz, 1H) 3.84 (s, 3H) 3.91 (t, J = 8.70 Hz, 1H) 6.53 (d, J = 3.05 Hz, 1H) 7.41 (d, J = 3.05 Hz, 1H) 7.54-7.63 (m, 2H) 7.97 (s, 1H) 8.03 (d, J = 8.39 Hz, 1H) 8.43 (br. s., 1H) 8.60 (s, 1H) 8.93 (s, 1H) | 370 | 2.09 |

| example | Structure | Name (¹H NMR) | [M + H]⁺ | retention time (min) |
|---|---|---|---|---|
| 65 | 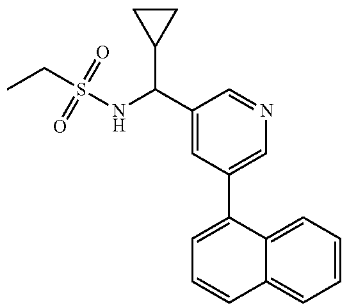 [SMILES: CCS(=O)(=O)NC(c1cncc(-c2cccc3ccccc23)c1)C1CC1] | N-(cyclopropyl(5-naphtalen-1-yl-pyridin-3-yl)methyl)ethanesulfonamide ¹H NMR (500 MHz, DMSO-d₆) δ ppm 0.44-0.65 (m, 4H) 1.11 (t, J = 7.32 Hz, 3H) 1.19-1.28 (m, 1H) 2.83 (dq, J = 14.34, 7.27 Hz, 1H) 2.95 (dq, J = 14.34, 7.27 Hz, 1H) 3.91 (t, J = 8.62 Hz, 1H) 7.49-7.66 (m, 4H) 7.74 (d, J = 8.39 Hz, 1H) 7.98 (d, J = 8.55 Hz, 1H) 8.01-8.07 (m, 3H) 8.62 (d, J = 1.53 Hz, 1H) 8.72 (d, J = 1.68 Hz, 1H) | 367 | 2.48 |

Example 66

N-(5-(6-chloro-1-methyl-1H-benzo[d]imidazol-2-yl)pyridin-3-yl)methyl)ethanesulfonamide

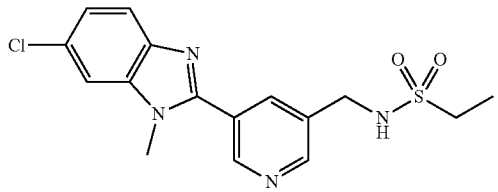 [SMILES: CCS(=O)(=O)NCc1cncc(-c2nc3ccc(Cl)cc3n2C)c1]

Step 1: Synthesis of 6-chloro-1-methyl-1H-benzo[d]imidazole

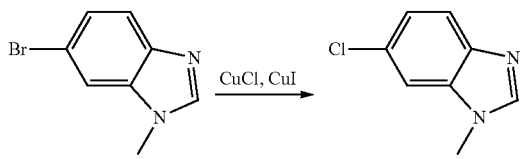

A microwave flask was charged with copper(I) chloride (1.87 g, 18.95 mmol), copper(I) iodide (0.36 g, 1.895 mmol) and 6-bromo-1-methyl-benzimidazole (2.00 g, 9.48 mmol), and the vial was flushed with nitrogen. NMP (18 mL) was added. The flask was heated under microwave irradiation to 200° C. for 1.5 h. The mixture was diluted with ethyl acetate (1.5 L) and a 9:1 saturated aqueous ammonium chloride-ammonium hydroxide solution was added (0.25 L). The mixture was stirred vigorously for 15 min and filtered through celite. The two phases were separated and the organic phase was washed with water (0.2 L*5). The combined organic phase was dried over MgSO₄, filtered and concentrated to give a moist pale brown solid, contaminated with NMP. The solid was redissolved in ethyl acetate and washed with water. The organic phase was dried over MgSO₄, filtered and concentrated to give 6-chloro-1-methyl-1H-benzo[d]imidazole. ESI-MS: m/z 167.1, (M+H)⁺.

Step 2: Synthesis of 6-chloro-2-iodo-1-methyl-1H-benzo[d]imidazole

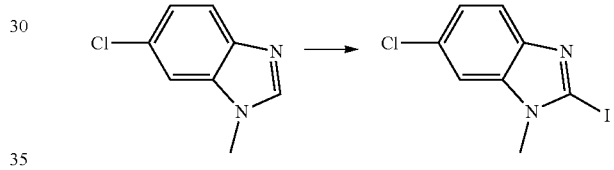

A flask charged with a solution of 6-chloro-1-methyl-1H-benzo[d]imidazole (2 g, 12 mmol) in THF (100 mL) was cooled to −78° C. and 1.8M LDA in THF/hexanes/ethylbenzene (9.34 mL, 16.81 mmol) was added dropwise, and the mixture was stirred at −78° C. for 1 h. A solution of 1,2-diiodoethane (3.72 g, 13.2 mmol) in THF (50 mL) was added dropwise and the mixture was stirred at −78° C. for 1 h. Water (0.3 mL) was added followed by silica gel (20 g) and the mixture was concentrated in vacuo. The residue was purified by silica chromatography eluting with EtOAc in heptane (v/v, 10 to 50%) to give 6-chloro-2-iodo-1-methyl-1H-benzo[d]imidazole. ¹H NMR (400 MHz, DMSO-d₆) δ ppm 3.76 (s, 3H) 7.19 (dd, J=8.59, 2.02 Hz, 1H) 7.58 (d, J=8.59 Hz, 1H) 7.78 (d, J=2.02 Hz, 1H).

Step 3: Synthesis of 5-(6-chloro-1-methyl-1H-benzo[d]imidazol-2-yl)nicotinaldehyde

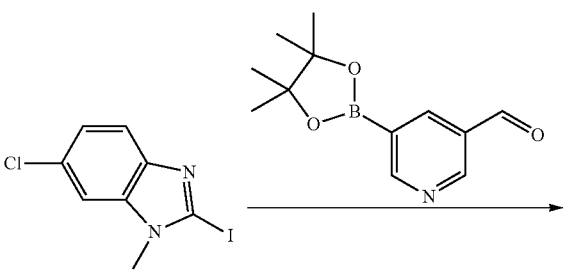

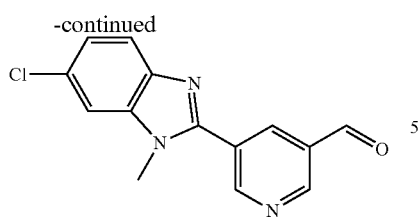

A flask was charged with 6-chloro-2-iodo-1-methyl-1H-benzo[d]imidazole (627 mg, 2.145 mmol), DMF (10 mL), 2M aqueous sodium carbonate (2.145 mL, 4.29 mmol) and 5-(4,4,5,5-tetramethyl-1,3,2-dioxaborolan-2-yl)nicotinaldehyde (1 g, 4.29 mmol). Nitrogen was bubbled through the mixture for 10 min and polymer bound Pd(PPh$_3$)$_4$ (1.19 g, 0.107 mmol) was added. The mixture was heated to 160° C. under micro-wave irradiation for 30 min. The mixture was filtered through a thin pad of celite, which was washed with EtOAc (100 mL). The filtrate was poured into water (200 mL) and extracted with EtOAc (500 mL). The organic phase was washed with water (50 mL), dried over Na$_2$SO$_4$ and concentrated. The residue was purified by silica chromatography eluting with 20 to 100% EtOAc in heptane to give 5-(6-chloro-1-methyl-1H-benzo[d]imidazol-2-yl)nicotinaldehyde. ESI-MS: m/z 272.1 (M+H)$^+$.

Step 4: synthesis of N-((5-(6-chloro-1-methyl-1H-benzo[d]imidazol-2-yl)pyridin-3-yl)methyl)ethanesulfonamide

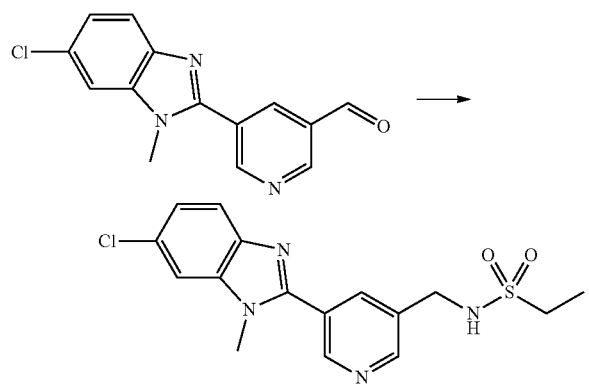

A flask was charged with 5-(6-chloro-1-methyl-1H-benzo[d]imidazol-2-yl)nicotinaldehyde (100 mg, 0.368 mmol), ethanesulfonamide (80 mg, 0.736 mmol) and toluene (3 mL), and titanium isopropoxide (157 mg, 0.552 mmol) was added dropwise. The mixture was stirred at 120° C. overnight. The mixture was concentrated in vacuo and the residue was taken up in DCM (20 mL) and MeOH (20 mL), and NaBH$_4$ (0.0557 g, 1.47 mmol) was added at 0° C. The mixture was stirred at 0° C. for 30 min. Water (1 mL) was added and the mixture was stirred for 5 min. DMF (5 mL) was added and the suspension was filtered. The filtrate was purified by Xbridge RP 18 eluting with a 20 to 70% ACN-water gradient to give the title compound. HRMS: (ESI) m/z 365.0839 [(M+H)$^+$ Calcd for C16H18ClN4O2S 365.0834]. $^1$H NMR (400 MHz, DMSO-d$_6$) δ ppm 1.21 (t, J=7.33 Hz, 3H) 3.06 (q, J=7.33 Hz, 2H) 3.92 (s, 3H) 4.33 (s, 2H) 7.30 (dd, J=8.46, 2.15 Hz, 1H) 7.73 (d, J=8.59 Hz, 1H) 7.77 (s, 1H) 7.86 (d, J=2.02 Hz, 1H) 8.25 (t, J=2.02 Hz, 1H) 8.72 (d, J=2.02 Hz, 1H) 8.97 (d, J=2.27 Hz, 1H).

Example 67

Ethanesulfonic acid [5-(6-chloro-1-methyl-1H-pyrrolo[2,3-b]pyridin-2-yl)-pyridin-3-yl methyl]-amide

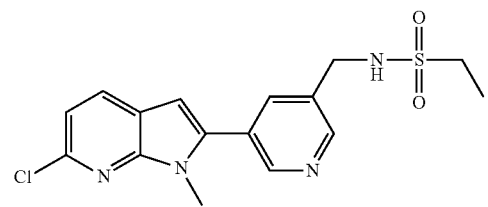 [SMILES: CCS(=O)(=O)NCc1cncc(-c2cc3ccc(Cl)nc3n2C)c1]

Step 1: Synthesis of 6-chloro-1-methyl-1H-pyrrolo[2,3-b]pyridine

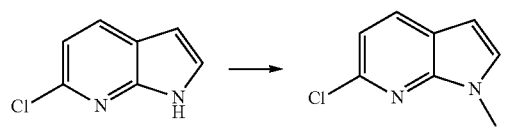

To a solution of 6 chloro-7-aza indole (1.00 g, 6.55 mmol) in DMF (30 mL) at 0° C. was added sodium hydride (0.524 g, 13.11 mmol) and the mixture was stirred at 0° C. for 20 min. Methyl iodide (0.512 mL, 8.19 mmol) was added at 0° C. and the mixture was warmed to room temperature and stirred for 2 h. The reaction was stopped, quenched with water and extracted with ethyl acetate. The organic layer was washed with water. It was then dried over sodium sulfate and concentrated in vacuo to give 1.01 g of the desires product as a brown color oil. ESI-MS: m/z 167.0 (M+H)

Step 2: Synthesis of 6-Chloro-N-methyl-7-aza indole-2-boronic acid

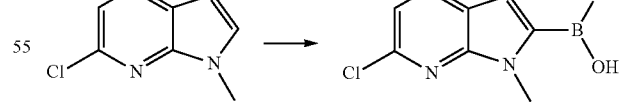

To a solution of 6-chloro-1-methyl-1H-pyrrolo[2,3-b]pyridine (1.02 g, 6.12 mmol)) in THF (60 mL) at −78° C. was added 1.7 M t-BuLi in pentane (9.00 mL, 15.31 mmol) and the mixture was stirred at −78° C. for 2 h. Trimethyl borate (1.026 mL, 9.18 mmol) was added at −78° C. and the mixture was allowed to warm to room temperature, and stirred at room temperature overnight. Water (2 mL) was added and the mixture was concentrated in vacuo. The solid was subjected to high vacuum overnight to afford 2.1 g of 6-chloro-N-methyl-7-aza indole-2-boronic acid. ESI-MS: m/z 211.1 (M+H)+

Step 3: Synthesis of 5-(6-chloro-1-methyl-1H-pyrrolo[2,3-b]pyridin-2-yl)-pyridine-3-carbaldehyde

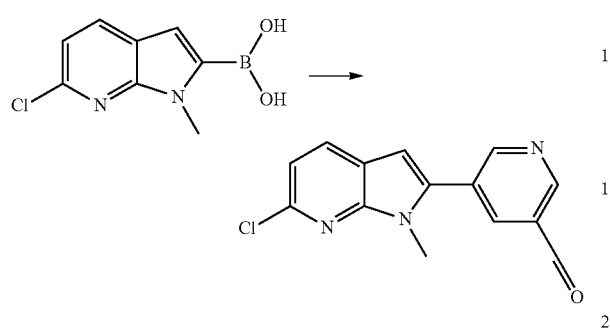

To 6-chloro-N-methyl-7-aza indole-2-boronic acid (1.00 g, 4.75 mmol) in dioxane (40 mL) under $N_2$ was added 5 bromo-3-pyridine carbaldehyde (0.589 g, 3.17 mmol), aqueous $Na_2CO_3$ (2M, 4.75 mL, 9.50 mmol) and polymer bound $Pd(PPh_3)_4$ (1.760 g, 0.158 mmol).

The reaction was stirred for 2 hours at 85° C. The reaction mixture was cooled to room temperature. The solids were filtered off and the precipitate was washed thoroughly with methanol. The filtrate was concentrated in vacuo to give a brown color oil. The crude was purified by silica gel flash chromatography using DCM-MeOH (90-10, v/v) to afford pure product 5-(6-Chloro-1-methyl-1H-pyrrolo[2,3-b]pyridin-2-yl)-pyridine-3-carbaldehyde as a solid. ESI-MS: m/z 272.1 (M+H)+

Step 4: Synthesis of ethanesulfonic acid [5-(6-chloro-1-methyl-1H-pyrrolo[2,3-b]pyridin-2-yl)-pyridin-3-ylmethyl]-amide

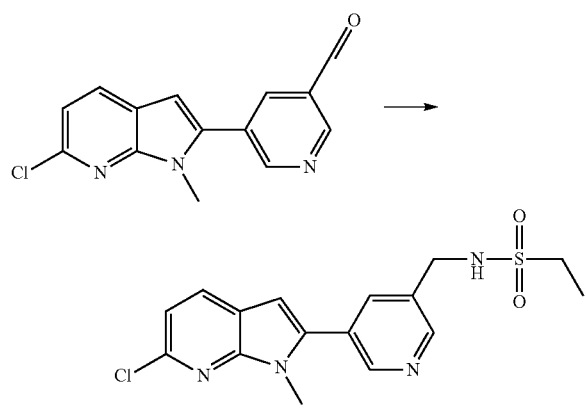

A 25 mL flask was charged with 5-(6-Chloro-1-methyl-1H-pyrrolo[2,3-b]pyridin-2-yl)-pyridine-3-carbaldehyde (91 mg, 0.335 mmol), ethane sulfonamide (73.1 mg, 0.670 mmol) and toluene (5 mL). Titanium(IV) isopropoxide (0.147 mL, 0.502 mmol) was added dropwise. The mixture was stirred at 120° C. overnight. The mixture was concentrated in vacuo. The residue was taken up in DCM (5 mL) and MeOH (5 mL) and sodium borohydride (50.7 mg, 1.340 mmol) was added at 0° C. The mixture was stirred at 0° C. for 30 min. Water (1 mL) was added and the mixture was stirred for 5 min, then concentrated in vacuo. DMF (5 mL) was added and the suspension was filtered. The filtrate was purified by Xbridge RP 18 eluting with a 5 to 95% ACN-water gradient to afford ethanesulfonic acid [5-(6-chloro-1-methyl-1H-pyrrolo[2,3-b]pyridin-2-yl)-pyridin-3-ylmethyl]-amide. ESI-MS: m/z 365.2 (M+H)$^1$H NMR (400 MHz, MeOD) δ ppm 1.38 (t, J=7.3 Hz, 2H), 3.23 (q, J=7.4 Hz, 2H), 4.08-4.17 (m, 2H), 4.59 (dd, J=8.8, 7.3 Hz, 2H), 7.10 (d, J=8.3 Hz, 1H), 7.53 (dd, J=8.6, 2.3 Hz, 1H), 7.63 (d, J=2.3 Hz, 1H), 7.92 (t, J=2.1 Hz, 1H), 8.40 (d, J=2.5 Hz, 1H), 8.56 (d, J=2.0 Hz, 2H)

HRMS: (ESI) m/z 365.08373 [(M+H)+ Calcd for $C_{16}H_{17}ClN_4O_2S$ 365.08335].

Example 68

Ethanesulfonic acid [5-(6-chloro-1-methyl-1H-pyrrolo[3,2-c]pyridin-2-yl)-pyridin-3-ylmethyl]-amide Step 1: Synthesis of 2-chloro-5-iodo-pyridin-4-ylamine A 100 mL round bottom flask was charged with 2-chloro-4-amino pyridine (3.0 g, 23.34 mmol), sodium acetate (11.49 g, 140 mmol) and acetic acid (60 mL). To this iodine monochloride (3.98 g, 24.50 mmol) was added and the reaction mixture stirred at 60° C. for 2 h. The reaction was cooled to room temperature and quenched with 1N saturated sodium bis-sulfite solution and extracted with DCM. The organic layer was dried over sodium sulfate and concentrated in vacuo. The crude was purified by silica gel flash chromatography using DCM-MeOH:95-5. 2-Chloro-5-iodo-pyridin-4-ylamine was obtained as a white color solid. ESI-MS: m/z 255.0 (M+H)+

Step 2: Synthesis of 5-ethynyl-nicotinic acid methyl ester

-continued

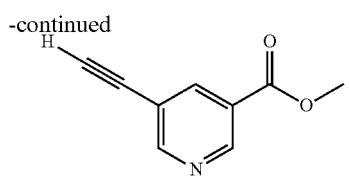

To methyl 5-bromonicotinate (3.0 g, 13.89 mmol) in TEA (50 mL) under $N_2$ was added ethynyltrimethylsilane (5.83 mL, 41.7 mmol), copper(I) iodide (0.132 g, 0.694 mmol) and bis(triphenylphosphine)palladium(II) chloride (0.487 g, 0.694 mmol). The reaction was stirred at 50° C. for 1 h. The reaction was cooled to room temperature and filtered to remove the solids. The precipitate was washed thoroughly with ethyl acetate. The filtrate was then washed with water twice and extracted with ethyl acetate. The organic layer was dried over sodium sulfate and concentrated in vacuo to afford a black color solid. Assuming 100% conversion this was taken on to next step for TMS removal. The crude was dissolved in MeOH (50 mL) and potassium carbonate (0.480 g, 3.47 mmol) was added to it. The reaction mixture was stirred for 30 min. The solids were filtered off, the filtrate was concentrated in vacuo. The crude was purified by silica gel flash chromatography using DCM-MeOH: 90-10 to give pure product 5-Ethynyl-nicotinic acid methyl ester as a light yellow solid. ESI-MS: m/z 162.1 $(M+H)^+$ Step 3: Synthesis of 5-(4-amino-6-chloro-pyridin-3-ylethynyl)-nicotinic acid methyl ester

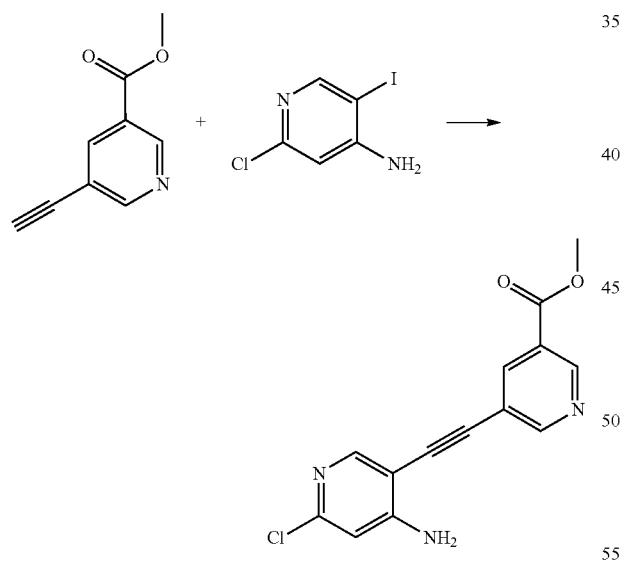

A 250 mL round bottom flask flushed with $N_2$ was charged with 2-chloro-5-iodo-pyridin-4-ylamine (1.00 g, 3.93 mmol), 5-ethynyl-nicotinic acid methyl ester (0.633 g, 3.93 mmol), copper(I) iodide (0.037 g, 0.196 mmol), bis(triphenylphosphine)palladium(II) chloride (0.138 g, 0.196 mmol) and triethyl amine (50 mL). The reaction mixture was stirred at 100° C. for 3 h. The reaction was cooled to room temperature, filtered and the precipitate washed thoroughly with ethyl acetate. The filtrate was washed with water twice. The organic layer was dried over sodium sulfate and concentrated in vacuo to afford crude product 5-(4-amino-6-chloro-pyridin-3-yl-ethynyl)-nicotinic acid methyl ester as a brown solid which was taken onto next step without any purification. ESI-MS: m/z 288.0 $(M+H)^+$ Step 4: synthesis of 5-(6-chloro-1-methyl-1H-pyrrolo[3,2-c]pyridin-2-yl)-nicotinic acid methyl ester

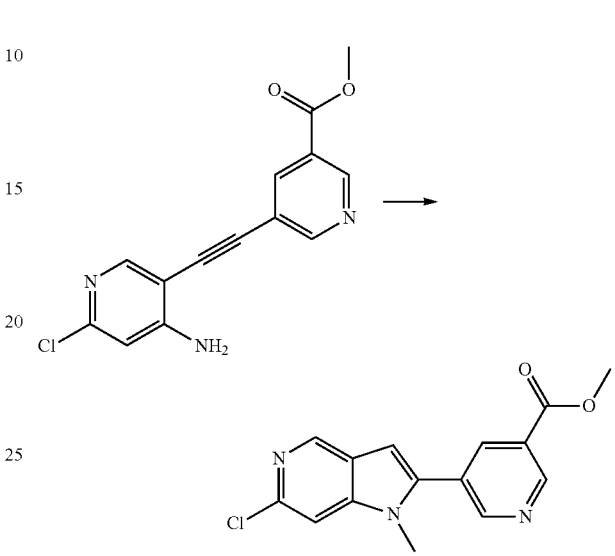

To 5-(4-amino-6-chloro-pyridin-3-ylethynyl)-nicotinic acid methyl ester (0.950 mg, 3.30 µmol) in NMP (15 mL) was added KO$^t$Bu (1.112 mg, 9.91 µmol) and the reaction was left to stir overnight at room temperature. The reaction was cooled to 0° C. and methyl iodide (0.619 µl, 9.91 µmol) was added. The reaction mixture was stirred for 30 min. The reaction was quenched with water and extracted with ethyl acetate twice. The combined organic layer was washed with water thrice, dried over sodium sulfate and concentrated in vacuo to afford desired product 5-(6-chloro-1-methyl-1H-pyrrolo[3,2-c]pyridin-2-yl)-nicotinic acid methyl ester as a brown color oil which was taken onto next step without further purification. ESI-MS: m/z 302.0 $(M+H)^+$ Step 5: Synthesis of 5-(6-chloro-1-methyl-1H-pyrrolo[3,2-c]pyridin-2-yl)-pyridin-3-yl]-methanol

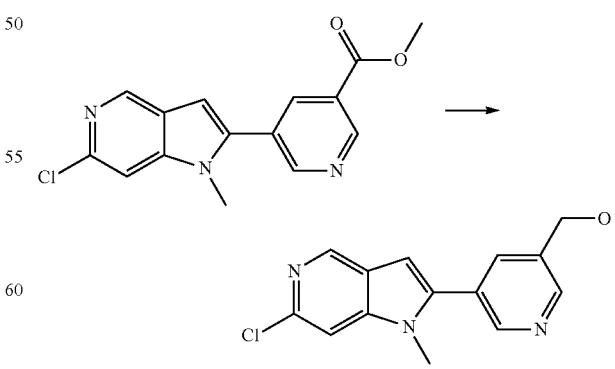

To 5-(6-chloro-1-methyl-1H-pyrrolo[3,2-c]pyridin-2-yl)-nicotinic acid methyl ester (0.780 g, 2.59 mmol) in THF (10 mL) at 0° C. was added LAH (5.17 mL, 5.17 mmol). The reaction mixture was stirred at room temperature for 45 min. The reaction mixture was quenched with water (1 mL), then washed with 2N NaOH solution (2 mL) and extracted with DCM twice. The organic layer was dried over sodium sulfate and concentrated in vacuo. The crude was purified by silica gel flash chromatography using DCM-MeOH: 90-10 to give 5-(6-chloro-1-methyl-1H-pyrrolo[3,2-c]pyridin-2-yl)-pyridin-3-yl]-methanol as a light yellow solid. ESI-MS: m/z 274.1 (M+H)+

Step 6: Synthesis of 5-(6-Chloro-1-methyl-1H-pyrrolo[3,2-c]pyridin-2-yl)-pyridine-3-carbaldehyde

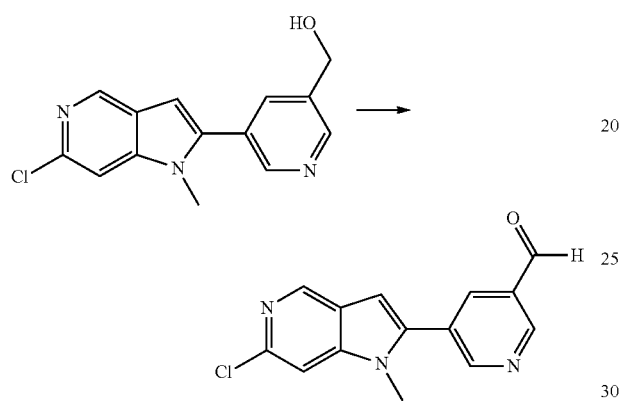

To 5-(6-chloro-1-methyl-1H-pyrrolo[3,2-c]pyridin-2-yl)-pyridin-3-yl]-methanol (128 mg, 0.468 mmol) in dioxane (5 ml) was added manganese dioxide (407 mg, 4.68 mmol). The reaction mixture was refluxed overnight. The reaction was cooled to room temperature and filtered through celite. The celite layer was washed thoroughly with MeOH. The filtrate was concentrated in vacuo to afford pure product 5-(6-Chloro-1-methyl-1H-pyrrolo[3,2-c]pyridin-2-yl)-pyridine-3-carbaldehyde as a yellow solid. ESI-MS: m/z 272.0 (M+H)+

Step 7: Synthesis of ethanesulfonic acid [5-(6-chloro-1-methyl-1H-pyrrolo[3,2-c]pyridin-2-yl)-pyridin-3-ylmethyl]-amide

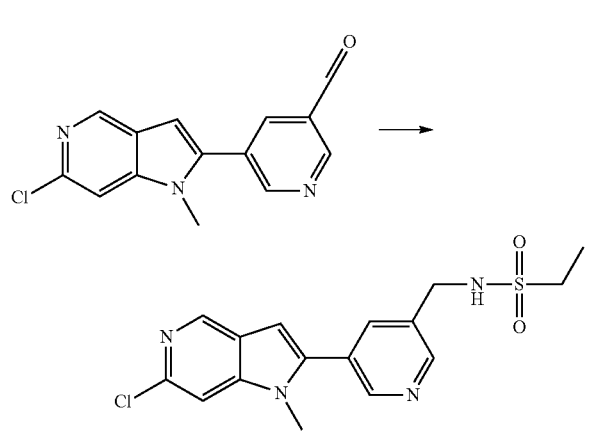

A procedure similar to Example 55 was used here. ESI-MS: m/z 365.1 (M+H)+ 1HNMR (400 MHz, MeOD) δ ppm 1.38 (t, J=7.5 Hz, 3H), 3.15 (q, J=7.3 Hz, 3H), 3.83 (s, 3H), 4.44 (s, 2H), 6.91 (s, 1H), 7.66 (s, 1H), 8.14 (t, J=1.9 Hz, 1H), 8.67 (s, 1H), 8.69 (d, J=2.0 Hz, 1H), 8.75 (d, J=2.0 Hz, 1H) HRMS: (ESI) m/z 365.08448 [(M+H)+ Calcd for $C_{16}H_{17}ClN_4O_2S$ 365.08338].

Example 69

N-((5-(3-chloro-4-cyanophenyl)pyridin-3-yl)(cyclopropyl)methyl)-N-methylethanesulfonamide

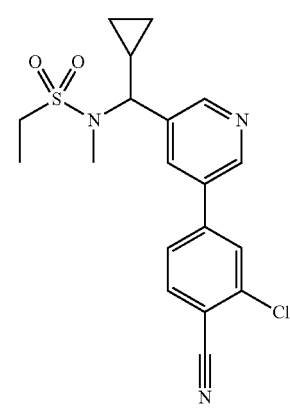 [SMILES: CCS(=O)(=O)N(C)C(c1cncc(-c2ccc(C#N)c(Cl)c2)c1)C1CC1]

Step 1: Synthesis of N-((5-bromopyridin-3-yl)(cyclopropyl)methyl)-N-methylethanesulfonamide

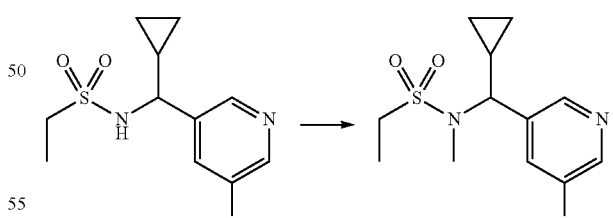

Iodomethane (0.059 mL, 0.940 mmol) was added to a mixture of N-((5-bromopyridin-3-yl)(cyclopropyl)methyl)ethanesulfonamide (200 mg, 0.627 mmol) and potassium carbonate (130 mg, 0.940 mmol) in DMF (6 mL) at room temperature. The resulting mixture was heated at 60° C. for 24 h. The reaction mixture was diluted with EtOAc and water, and the mixture was washed with $H_2O$ and brine. The organic layer was separated and dried over anhydrous $Na_2SO_4$. After filtration and concentration, the residue was purified by flash column to give 32 mg of N-((5-bromopyridin-3-yl)(cyclopropyl)methyl)-N-methylethanesulfonamide. ESI-MS: m/z 334.9 (M+H)+.

Step 2: Synthesis of N-((5-(3-chloro-4-cyanophenyl)pyridin-3-yl)(cyclopropyl)methyl)-N-methylethanesulfonamide

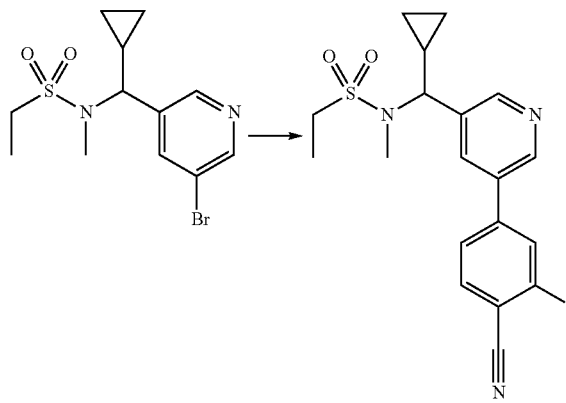

Similar Suzuki coupling condition in example 34 was used here. ESI-MS: m/z 390.1 (M+H)+; $^1$H NMR (400 MHz, MeOD) δ ppm 0.44-0.50 (m, 1H), 0.61-0.67 (m, 1H), 0.79-0.91 (m, 2H), 1.35 (t, J=7.6 Hz, 3H), 1.60-1.69 (m, 1H), 2.86 (s, 3H), 3.19 (q, J=7.6 Hz, 2H), 4.31 (d, J=10.4 Hz, 1H), 7.81 (dd, J=8, 1.6 Hz, 1H), 7.94 (d, J=8 Hz, 1H), 8.01 (d, J=1.6 Hz, 1H), 8.25 (t, J=1.6 Hz, 1H), 8.79 (d, J=1.6 Hz, 1H), 8.82 (d, J=1.6 Hz, 1H).

Example 70

2-Chloro-4-[5-(1,1-dioxo-isothiazolidin-2-ylmethyl)-pyridin-3-yl]-benzonitrile

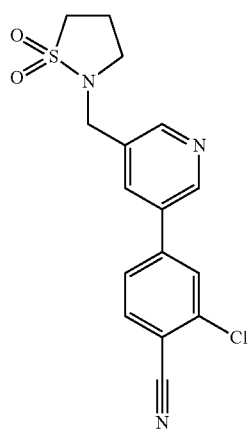 [SMILES: N#Cc1ccc(-c2cncc(CN3CCCS3(=O)=O)c2)cc1Cl]

Step 1: synthesis of 3-bromo-5-(1,1-dioxo-isothiazolidin-2-ylmethyl)-pyridine

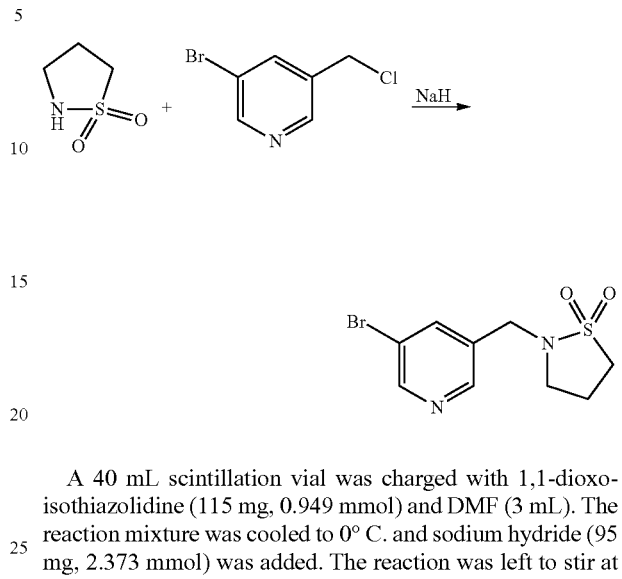

A 40 mL scintillation vial was charged with 1,1-dioxo-isothiazolidine (115 mg, 0.949 mmol) and DMF (3 mL). The reaction mixture was cooled to 0° C. and sodium hydride (95 mg, 2.373 mmol) was added. The reaction was left to stir at room temperature for 20 min followed by the addition of 3-bromo-5-(chloromethyl)pyridine hydrochloride (277 mg, 1.139 mmol). The reaction was stirred at room temperature for 3 h, then quenched with water and extracted with ethyl acetate. The organic layer was washed with water twice, dried over sodium sulfate and concentrated in vacuo. The crude was purified by silica gel flash chromatography using heptane-ethyl acetate (60-40, v/v) to afford 3-bromo-5-(1,1-dioxo-isothiazolidin-2-ylmethyl)-pyridine as a colorless oil. MS (ESI) m/z 292.9 (M+H)+

Step 2: synthesis of 2-chloro-4-[5-(1,1-dioxo-isothiazolidin-2-ylmethyl)-pyridin-3-yl]-benzonitrile

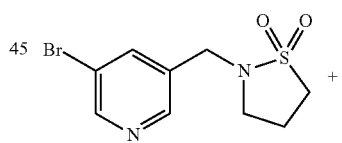

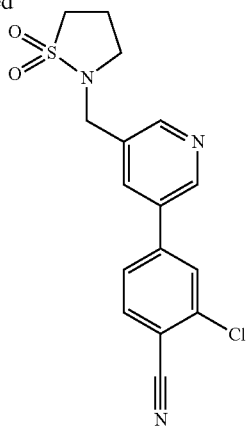

To 2-chloro-4-(4,4,5,5-tetramethyl-[1,3,2]dioxaborolan-2-yl)-benzonitrile (217 mg, 0.824 mmol) in DMF (4 mL) were added 3-bromo-5-(1,1-dioxo-isothiazolidin-2-ylmethyl)-pyridine (200 mg, 0.687 mmol) and 2M aqueous sodium carbonate (0.687 mL, 1.374 mmol). The reaction mixture was flushed and evacuated with $N_2$ thrice followed by the addition of $PdCl_2(dppf) \cdot CH_2Cl_2$ adduct (28.0 mg, 0.034 mmol). The reaction mixture was stirred at 100° C. for 1 hour. The reaction was cooled to room temperature, diluted with ethyl acetate and washed with water thrice. The organic layer was separated, dried over sodium sulfate and concentrated in vacuo. The crude was dissolved in DMF (5 mL) and purified using Xbridge C18 eluting with a 10 to 100% ACN-water to afford 2-chloro-4-[5-(1,1-dioxo-isothiazolidin-2-ylmethyl)-pyridin-3-yl]-benzonitrile as a white solid. HRMS: (ESI) m/z 348.0575 [(M+H)$^+$ Calcd for $C_{16}H_{14}ClN_3O_2S$ 348.0573]. $^1$H NMR (400 MHz, MeOD) δ ppm 2.33-2.47 (m, 2H), 3.24-3.33 (m, 4H), 4.37 (s, 2H), 7.87 (dd, J=8.2, 1.6 Hz, 1H), 7.97 (d, J=8.1 Hz, 1H), 8.06 (d, J=1.5 Hz, 1H), 8.22 (t, J=2.1 Hz, 1H), 8.68 (d, J=2.0 Hz, 1H), 8.87 (d, J=2.3 Hz, 1H).

Example 71

Ethanesulfonic acid {[5-(3-chloro-4-cyano-phenyl)-pyridin-3-yl]-cyclopropyl-methyl}-ethyl-amide

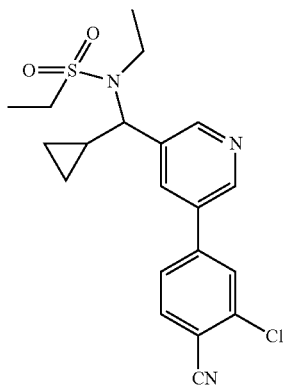 [SMILES: CCN(C(c1cncc(-c2ccc(C#N)c(Cl)c2)c1)C1CC1)S(=O)(=O)CC]

A 40 mL scintillation vial was charged with ethanesulfonic acid {[5-(3-chloro-4-cyano-phenyl)-pyridin-3-yl]-cyclopropyl-methyl}-amide (0.075 g, 0.200 mmol) and DMF (3 mL). The reaction mixture was cooled to 0° C. and sodium hydride (0.012 g, 0.299 mmol) was added. The reaction was left to stir at room temperature for 20 min followed by the addition of iodoethane (0.050 g, 0.319 mmol). The reaction was stirred at room temperature overnight. The reaction was quenched with water (0.5 mL) and filtered. The filtrate was dissolved in DMF (3 mL) and purified using Xbridge C18 eluting with a 10 to 100% ACN-water to afford pure product ethanesulfonic acid {[5-(3-chloro-4-cyano-phenyl)-pyridin-3-yl]-cyclopropyl-methyl}-ethyl-amide as a white color solid. HRMS: (ESI) m/z 404.1190 [(M+H)$^+$ Calcd for $C_{20}H_{22}ClN_3O_2S$ 404.1199]. $^1$H NMR (400 MHz, MeOD) δ ppm 0.52-0.68 (m, 1H), 0.71-0.82 (m, 1H), 0.91-1.05 (m, 2H), 1.22 (t, J=7.1 Hz, 3H), 1.43 (t, J=7.5 Hz, 3H), 1.60-1.88 (m, 1H), 3.28 (q, J=7.3 Hz, 2H), 3.39-3.51 (m, 1H), 3.55-3.66 (m, 1H), 4.32 (d, J=10.6 Hz, 1H), 7.93 (dd, J=8.1, 1.8 Hz, 1H), 8.06 (d, J=8.3 Hz, 1H), 8.15 (d, J=1.5 Hz, 1H), 8.87 (s, 1H), 9.04 (d, J=1.8 Hz, 1H), 9.14 (d, J=1.8 Hz, 1H).

Examples 72-74 were prepared according to the procedure described in Example 71

Example 72

Ethanesulfonic acid {[5-(3-chloro-4-cyano-phenyl)-pyridin-3-yl]-cyclopropyl-methyl}-(3-methyl-butyl)-amide

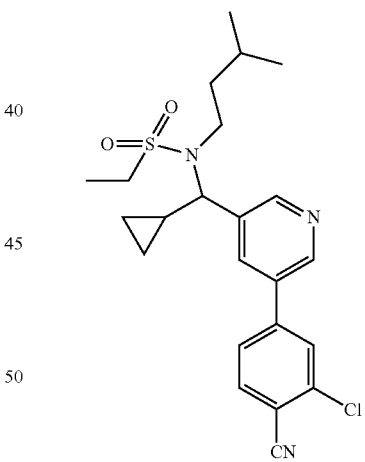

HRMS: (ESI) m/z 446.1660 [(M+H)$^+$ Calcd for $C_{23}H_{28}ClN_3O_2S$ 446.1669].

$^1$H NMR (400 MHz, MeOD) δ ppm 0.56-0.69 (m, 1H), 0.72-0.82 (m, 1H), 0.87 (d, J=6.3 Hz, 3H), 0.89 (d, J=6.3 Hz, 3H), 0.93-1.08 (m, 2H), 1.32-1.40 (m, 1H), 1.43 (t, J=7.3 Hz, 3H), 1.50-1.62 (m, 2H), 1.67-1.80 (m, 1H), 3.28 (q, J=7.3 Hz, 2H), 3.37-3.44 (m, 1H), 3.54-3.60 (m, 1H), 4.31 (d, J=10.4

Hz, 1H), 7.92 (dd, J=8.1, 1.8 Hz, 1H), 8.06 (d, J=8.1 Hz, 1H), 8.14 (d, J=1.5 Hz, 1H), 8.85 (s, 1H), 9.04 (d, J=1.8 Hz, 1H), 9.13 (d, J=2.0 Hz, 1H).

Example 73

({[5-(3-Chloro-4-cyano-phenyl)-pyridin-3-yl]-cyclopropyl-methyl}-ethanesulfonyl-amino)-acetic acid methyl ester

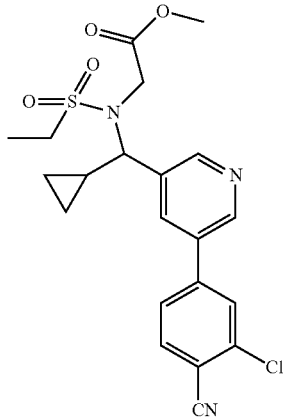 [SMILES: CCS(=O)(=O)N(CC(=O)OC)C(c1cncc(-c2ccc(C#N)c(Cl)c2)c1)C1CC1]

HRMS: (ESI) m/z 448.1088 [(M+H)$^+$ Calcd for $C_{21}H_{22}ClN_3O_4S$ 448.1098]. $^1$H NMR (400 MHz, MeOD) δ ppm 0.55-0.60 (m, 1H), 0.76-0.81 (m, 1H), 0.87-0.91 (m, 2H), 1.38 (t, J=7.3 Hz, 3H), 1.54-1.61 (m, 1H), 3.34 (q, J=7.3 Hz, 2H), 3.66 (s, 3H), 4.27 (d, J=18.7 Hz, 1H), 4.36 (d, J=10.4 Hz, 1H), 4.38 (d, J=18.7 Hz, 1H), 7.92 (dd, J=8.2, 1.6 Hz, 1H), 8.02 (d, J=8.3 Hz, 1H), 8.14 (d, J=1.5 Hz, 1H), 8.94-8.96 (m, 1H), 9.05 (d, J=2.0 Hz, 1H), 9.09 (d, J=2.0 Hz, 1H)

Example 74

Ethanesulfonic acid {[5-(3-chloro-4-cyano-phenyl)-pyridin-3-yl]-cyclopropyl-methyl}-isobutyl-amide

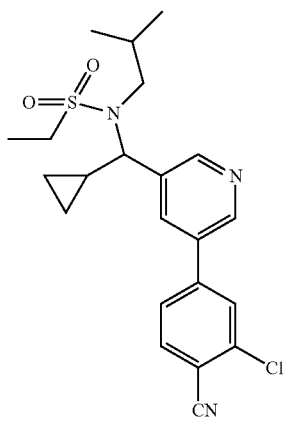 [SMILES: CCS(=O)(=O)N(CC(C)C)C(c1cncc(-c2ccc(C#N)c(Cl)c2)c1)C1CC1]

HRMS: (ESI) m/z 432.1503 [(M+H)$^+$ Calcd for $C_{22}H_{26}ClN_3O_2S$ 432.1512].
$^1$H NMR (400 MHz, MeOD) δ ppm 0.38-0.56 (m, 1H), 0.71-0.80 (m, 1H), 0.85 (d, J=6.6 Hz, 3H), 0.87 (d, J=6.6 Hz, 3H), 0.92-1.01 (m, 2H), 1.42 (t, J=7.5 Hz, 3H), 1.70-1.88 (m, 2H), 3.11 (dd, J=14.3, 8.7 Hz, 1H), 3.19-3.29 (m, 2H), 3.36-3.37 (m, 1H), 4.25 (d, J=10.6 Hz, 1H), 7.88 (dd, J=8.1, 1.8 Hz, 1H), 8.02 (d, J=8.1 Hz, 1H), 8.08 (d, J=1.5 Hz, 1H), 8.62 (s, 1H), 8.97 (d, J=4.3 Hz, 2H).

Example 75

Ethanesulfonic acid {[5-(3-chloro-4-cyano-phenyl)-pyridin-3-yl]-cyclopropyl-methyl}-(2-hydroxy-ethyl)-amide

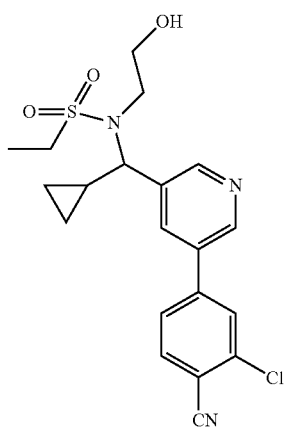 [SMILES: CCS(=O)(=O)N(CCO)C(c1cncc(-c2ccc(C#N)c(Cl)c2)c1)C1CC1]

A 40 mL scintillation vial was charged with ({[5-(3-chloro-4-cyano-phenyl)-pyridin-3-yl]-cyclopropyl-methyl}-ethanesulfonyl-amino)-acetic acid methyl ester (130 mg, 0.290 mmol) in THF (5 mL). The reaction mixture was cooled to 78° C. and lithium aluminium hydride (1M in THF, 0.726 mL, 0.726 mmol) was added. The reaction was left to stir at −78° C. for 1 h. The reaction was quenched with water (1 mL), warmed to room temperature and concentrated in vacuo. The crude was dissolved in DMSO (4 mL) and purified using Xbridge C18 eluting with a 10 to 100% ACN-water to afford ethanesulfonic acid {[5-(3-chloro-4-cyano-phenyl)-pyridin-3-yl]-cyclopropyl-methyl}-(2-hydroxy-ethyl)-amide as a white solid.

HRMS: (ESI) m/z 420.1130 [(M+H)$^+$ Calcd for $C_{20}H_{22}ClN_3O_3S$ 420.1148].
$^1$H NMR (400 MHz, MeOD) δ ppm 0.48-0.59 (m, 1H), 0.70-0.79 (m, 1H), 0.85-1.02 (m, 2H), 1.40 (t, J=7.3 Hz, 3H), 1.66-1.79 (m, 1H), 3.29 (q, J=7.3 Hz, 2H), 3.41-3.49 (m, 1H), 3.54-3.63 (m, 2H), 3.63-3.71 (m, 1H), 4.27 (d, J=10.4 Hz, 1H), 7.87 (dd, J=8.1, 1.8 Hz, 1H), 7.98 (d, J=8.1 Hz, 1H), 8.06 (d, J=1.8 Hz, 1H), 8.41 (t, J=1.9 Hz, 1H), 8.85 (d, J=2.0 Hz, 1H), 8.89 (d, J=2.0 Hz, 1H)

Example 76

N-(1-(5-(3-chloro-4-cyanophenyl)pyridin-3-yl)cyclopropyl)ethane-sulfonamide

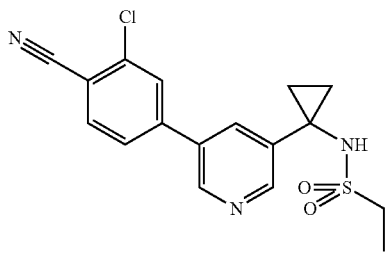 [SMILES: CCS(=O)(=O)NC1(c2cncc(-c3ccc(C#N)c(Cl)c3)c2)CC1]

Step 1: synthesis of methyl 2-(5-bromopyridin-3-yl)acetate

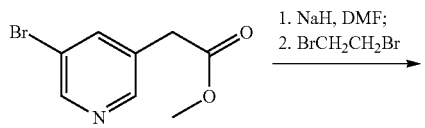

To a suspension of 2-(5-bromopyridin-3-yl)acetic acid (5 g, 23.14 mmol) in MeOH (100 mL) was added thionyl chloride (1.858 mL, 25.5 mmol) at 0° C., and the mixture was stirred at 0° C. for 2 h. The mixture was concentrated in vacuo, re-dissolved in DCM (100 mL) and MeOH (10 mL), and saturated NaHCO₃ in water (5 mL) was added, followed with NaHCO₃ (10 g). To the mixture was added silica gel (10 g) and the mixture was concentrated. The residue was purified by silica chromatography eluting with 0-50% EtOAc-heptane to give methyl 2-(5-bromopyridin-3-yl)acetate. ¹H NMR (400 MHz, DMSO-d₆) δ ppm 3.64 (s, 3H), 3.80 (s, 2H), 8.01 (dd, J=2.0 Hz, 1H), 8.48 (d, J=1.8 Hz, 1H), 8.61 (d, J=2.3 Hz, 1H).

Step 2: synthesis of methyl 1-(5-bromopyridin-3-yl)cyclopropanecarboxylate

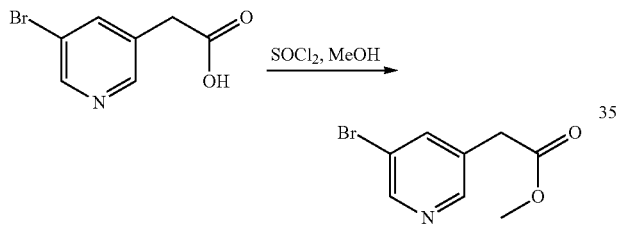

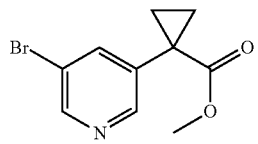

To a solution of methyl 2-(5-bromopyridin-3-yl)acetate (4.8 g, 20.86 mmol) in DMF (100 mL) was added 60% NaH in mineral oil (1.1 g, 45.9 mmol), and the mixture was stirred at 0° C. for 15 min. A solution of 1,2-dibromoethane (3.92 g, 20.86 mmol) in DMF (20 mL) was added and the mixture was stirred at room temperature for 1 h. Two other portions of 60% NaH in mineral oil (200 and 450 mg) were added sequentially, until conversion was complete. The mixture was poured into EtOAc (1 L) and washed with water (60 mL), dried over Na₂SO₄ and concentrated in vacuo to give an oil which was used in next step without further purification.

Step 3: synthesis of potassium 1-(5-bromopyridin-3-yl)cyclopropanecarboxylate

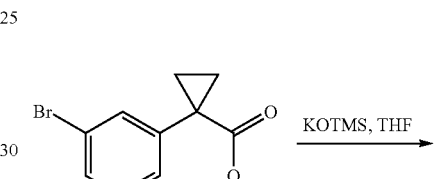

To a solution of methyl 1-(5-bromopyridin-3-yl)cyclopropanecarboxylate (1 g, 3.9 mmol) in THF (40 mL) was added 90% KOTMS (0.557 g, 3.9 mmol), and the mixture was stirred at room temperature overnight. The mixture was filtered and washed with THF to give potassium 1-(5-bromopyridin-3-yl)cyclopropanecarboxylate. ¹H NMR (400 MHz, DMSO-d₆) δ ppm 0.63-0.69 (m, 2H), 1.09-1.15 (m, 2H), 7.79-7.80 (m, 1H), 8.34-8.37 (m, 2H).

Step 4: synthesis of 1-(5-(3-chloro-4-cyanophenyl) pyridin-3-yl)cyclopropanecarboxylic acid

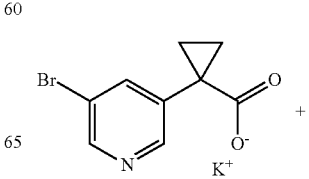

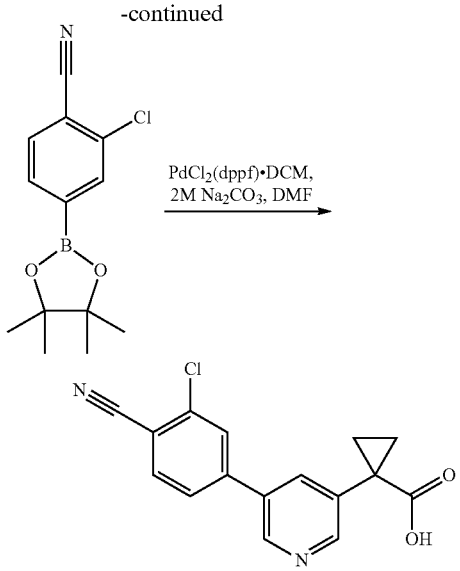

To a suspension of potassium 1-(5-bromopyridin-3-yl)cyclopropanecarboxylate (28 mg, 0.1 mmol), 2-chloro-4-(4,4,5,5-tetramethyl-1,3,2-dioxaborolan-2-yl)benzonitrile (26 mg, 0.1 mmol), PdCl$_2$(dppf).CH$_2$Cl$_2$ (4.08 mg, 5.0 mmol) in DMF (1 mL) was added 2M Na$_2$CO$_3$ (0.1 mL, 0.2 mmol), and the mixture was heated to 100° C. for 2 h. The mixture was concentrated and purified by silica chromatography eluting with a 0-10% MeOH-DCM gradient to give 1-(5-(3-chloro-4-cyanophenyl)pyridin-3-yl)cyclopropanecarboxylic acid. MS: (ESI) m/z 299.0, 301.0 (M+H)$^+$.

Step 5: synthesis of 4-(5-(1-aminocyclopropyl)pyridin-3-yl)-2-chlorobenzonitrile

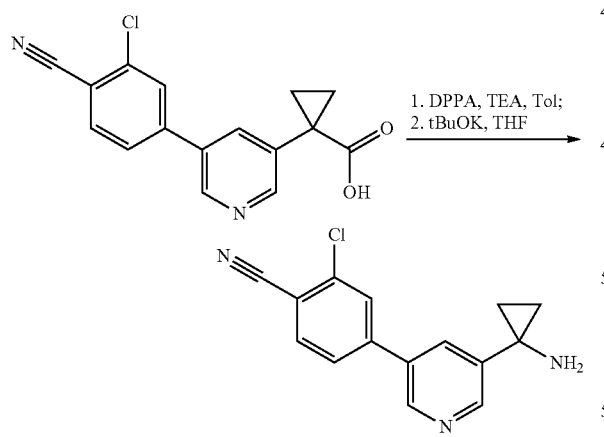

To a solution of 1-(5-(3-chloro-4-cyanophenyl)pyridin-3-yl)cyclopropanecarboxylic acid (900 mg, 3.01 mmol) in toluene (50 mL) was added TEA (0.63 mL, 4.52 mmol) and diphenylphosphoryl azide (0.977 mL, 4.52 mmol), and the mixture was heated to 100° C. for 4 h. The mixture was then cooled to room temperature and concentrated in vacuo. The residue was re-dissolved in THF (100 mL) and a solution of KOtBu (2.03 g, 18.08 mmol) in THF (40 mL) was added. The mixture was stirred at 0° C. for 1 h. The mixture was then warmed to room temperature overnight. Silica gel (10 g) was added and the mixture was concentrated in vacuo. The residue was purified by silica chromatography eluting with a 0-10% MeOH-DCM gradient to give 4-(5-(1-aminocyclopropyl)pyridin-3-yl)-2-chlorobenzonitrile. m/z 270.0, 272.0 (M+H)$^+$.

Step 6: synthesis of N-(1-(5-(3-chloro-4-cyanophenyl)pyridin-3-yl)cyclopropyl)ethanesulfonamide

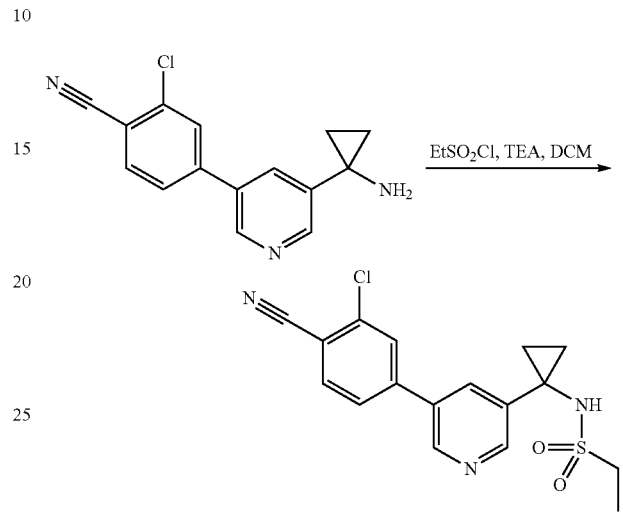

To a solution of 4-(5-(1-aminocyclopropyl)pyridin-3-yl)-2-chlorobenzonitrile (70 mg, 0.26 mmol) in DCM (3 mL) at room temperature was added TEA (0.109 mL, 0.779 mmol) and EtSO$_2$Cl (74 μL, 0.779 mmol) dropwise, and the mixture was stirred at room temperature for 1 h. The mixture was concentrated in vacuo, re-dissolved in DMF (3 mL) and filtered. The filtrate was purified by Xbridge Phenyl followed by Xbridge C18 eluting with 20-80% ACN-water gradient to give N-(1-(5-(3-chloro-4-cyanophenyl)pyridin-3-yl)cyclopropyl)ethanesulfonamide. HRMS: (ESI) m/z 362.0712 [(M+H)$^+$ Calcd for C$_{17}$H$_{16}$ClN$_3$O$_2$S 362.0725]. $^1$H NMR (400 MHz, CHLOROFORM-d) δ ppm 1.28 (t, J=7.3 Hz, 3H), 1.32-1.38 (m, 2H), 1.49-1.54 (m, 2H), 2.90 (q, J=7.4 Hz, 2H), 7.60 (dd, J=8.1, 1.8 Hz, 1H), 7.74 (d, J=1.8 Hz, 1H), 7.79 (d, J=8.1 Hz, 1H), 8.01 (t, J=2.3 Hz, 1H), 8.67 (d, J=2.3 Hz, 1H), 8.72 (d, J=2.3 Hz, 1H).

Example 77

N-((4-chloro-5-(3-chloro-4-cyanophenyl)pyridin-3-yl)(cyclopropyl)methyl)-N-methylmethanesulfonamide (LHV599)

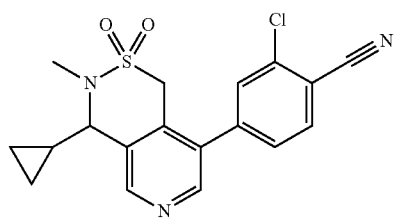 [SMILES: CN1C(C2CC2)c2cncc(-c3ccc(C#N)c(Cl)c3)c2CS1(=O)=O]

Step 1: synthesis of
N-(cyclopropylmethylene)methanesulfonamide

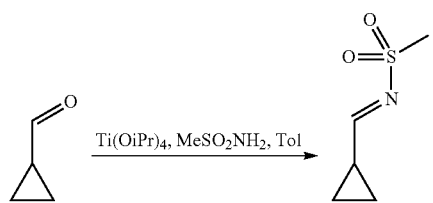

To a solution of cyclopropanecarbaldehyde (0.374 mL, 5 mmol) and methanesulfonamide (0.523 g, 5.5 mmol) in toluene (15 mL) was added titanium(IV) isopropoxide (2.93 mL, 10 mmol), and the mixture was heated to 100° C. for 1 day. The mixture was cooled to room temperature and concentrated in vacuo. The residue was placed under high vacuum for 30 min to give a biphasic mixture. The top layer was discarded. The residue was used in next step without further purification.

Step 2: synthesis of N-((5-bromo-4-chloropyridin-3-yl)(cyclopropyl)methyl)-N-methylmethanesulfonamide

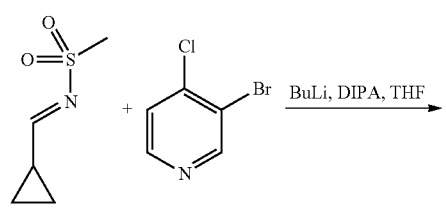

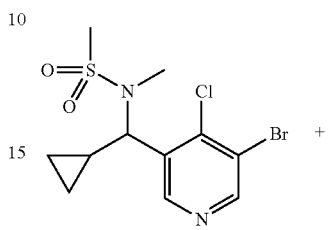

To a solution of DIPA (1.71 mL, 12 mmol) in THF (50 mL) at −78° C. was added 1.6M BuLi (7.5 mL, 12.0 mmol) and the mixture was stirred at −78° C. for 2 h. The LDA solution was cannulated into a solution of 3-bromo-4-chloropyridine (2.117 g, 11 mmol) in THF (50 mL) at −78° C., and the mixture was stirred at −78° C. for 1 h. A solution of N-(cyclopropylmethylene)methanesulfonamide (10 mmol, crude mixture) in THF (50 mL) was added and the mixture was stirred at −78° C. for 1 h. A solution of MeI (0.625 mL, 10 mmol) in THF (10 mL) was added, and the mixture was warmed to room temperature and stirred overnight. Water (0.5 mL) was added and the mixture was concentrated in vacuo. The residue was purified by silica gel chromatography eluting with a 0-50% EtOAc-heptane gradient to give N-((5-bromo-4-chloropyridin-3-yl)(cyclopropyl)methyl)-N-methylmethanesulfonamide. MS (ESI): m/z 353.0, 355.0 (M+H)$^+$.

Step 3: synthesis of N-((4-chloro-5-(3-chloro-4-cyanophenyl)pyridin-3-yl)(cyclopropyl)methyl)-N-methylmethanesulfonamide

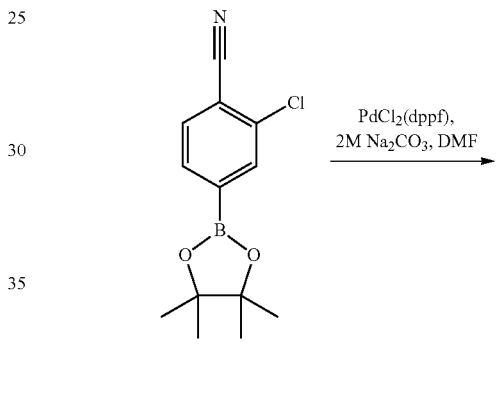

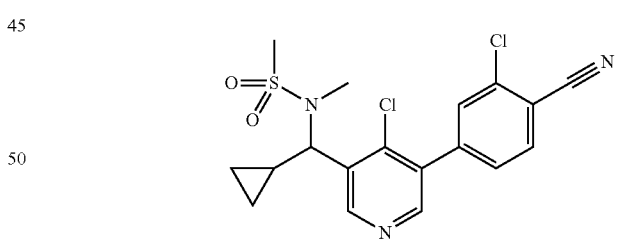

To a solution of N-((5-bromo-4-chloropyridin-3-yl)(cyclopropyl)methyl)-N-methylmethanesulfonamide (1.03 g, 2.9 mmol) and 2-chloro-4-(4,4,5,5-tetramethyl-1,3,2-dioxaborolan-2-yl)benzonitrile (2.29 g, 8.7 mmol) in DMF (20 mL) was added PdCl$_2$(dppf).CH$_2$Cl$_2$ (118 mg, 0.145 mmol) and 2M Na$_2$CO$_3$ in water (2.9 mL, 5.8 mmol), and the mixture was heated to 85° C. for 7 h. The mixture was cooled to room temperature, poured into water (100 mL), extracted with EtOAc (200 mL*3), washed with water (20 mL*3) and dried over Na$_2$SO$_4$. The mixture was purified by silica gel chromatography eluting with a 0-50% EtOAc-heptane gradient to give N-((4-chloro-5-(3-chloro-4-cyanophenyl)pyridin-3-yl)

(cyclopropyl)methyl)-N-methylmethanesulfonamide. MS (ESI): m/z 410.1, 412.1 (M+H)+.

Step 4: synthesis of 2-chloro-4-(4-cyclopropyl-3-methyl-2,2-dioxo-1,2,3,4-tetrahydro-2-thia-3,6-diaza-naphthalen-8-yl)-benzonitrile

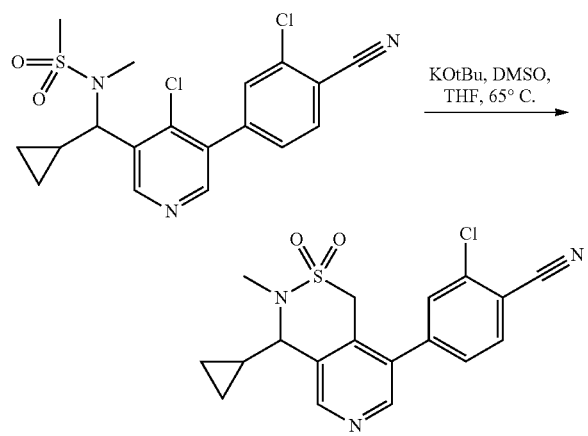

To a solution of N-((4-chloro-5-(3-chloro-4-cyanophenyl)pyridin-3-yl)(cyclopropyl)methyl)-N-methylmethanesulfonamide (51 mg, 0.124 mmol) in THF (10 mL) and DMSO (0.1 mL) was added 1M KOtBu in THF (0.37 mL, 0.37 mmol), and the mixture was heated to 65° C. for 10 min under microwave irradiation. The mixture was quenched with MeOH (2 mL) and concentrated. The residue was purified by Xbridge C18 eluting with 20-100% ACN-water to give 2-chloro-4-(4-cyclopropyl-3-methyl-2,2-dioxo-1,2,3,4-tetrahydro-2-thia-3,6-diaza-naphthalen-8-yl)-benzonitrile HRMS: (ESI) m/z 374.0731 [(M+H)+ Calcd for $C_{18}H_{16}ClN_3O_2S$ 374.0725].

$^1$H NMR (400 MHz, DMSO-$d_6$) δ ppm −0.79--0.69 (m, 1H), 0.12-0.21 (m, 1H), 0.29-0.41 (m, 2H), 0.99-1.11 (m, 1H), 2.86 (s, 3H), 3.98 (d, J=9.1 Hz, 1H), 4.71-4.84 (m, 2H), 7.35 (d, J=4.8 Hz, 1H), 7.63 (dd, J=8.0, 1.6 Hz, 1H), 7.84 (d, J=1.3 Hz, 1H), 8.07 (d, J=8.3 Hz, 1H), 8.57 (d, J=5.1 Hz, 1H).

Example 78

N-((5-(6-cyanonaphthalen-2-yl)pyridin-3-yl)(cyclopropyl)methyl)ethane-sulfonamide

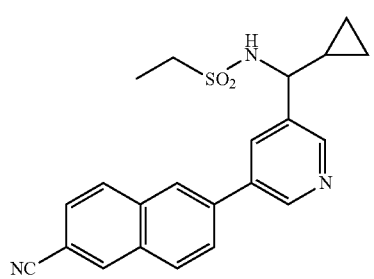 [SMILES: CCS(=O)(=O)NC(c1cncc(-c2ccc3cc(C#N)ccc3c2)c1)C1CC1]

Step 1: Synthesis of 6-bromo-2-naphthamide

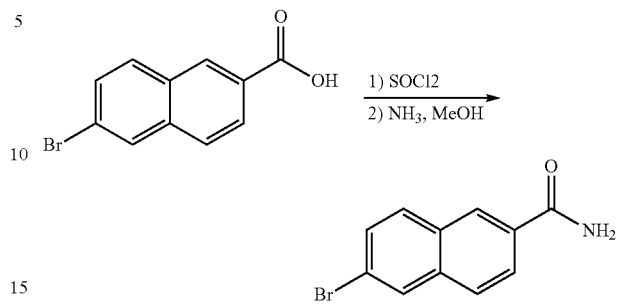

6-bromo-2-naphthoic acid (2 g, 7.97 mmol) was stirred in thionyl chloride (13.28 ml) at 70° C. for 16 h. After concentration in vacuo, the residue was rediluted in $CH_2Cl_2$ and concentrated again. To the acid chloride intermediate was added ammonia in MeOH (7 M, 13.66 ml, 96 mmol) and the mixture was stirred at room temperature for 3 h. The mixture was then concentrated. The residue was taken up in AcOEt, filtered, rinsed with AcOEt and then dried over $MgSO_4$, filtered and concentrated in vacuo. The title compound (1.802 g, 90%) was isolated as a beige solid. LC-MS (M+1) 251.9, t=1.34 min.

Step 2: Synthesis of 6-bromo-2-naphthonitrile

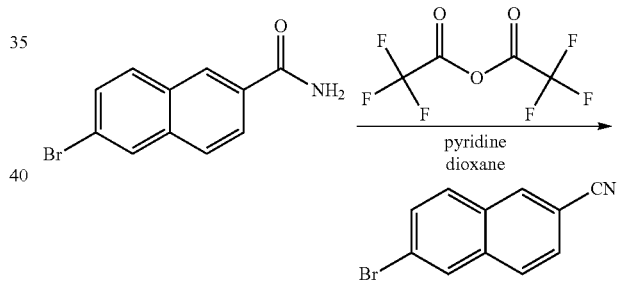

To 6-bromo-2-naphthamide (1 g, 4.00 mmol) in dioxane (8.00 ml) at 0° C. was added pyridine (0.647 ml, 8.00 mmol) and then TFAA (0.621 ml, 4.40 mmol) dropwise. The reaction was stirred at room temperature for 3 h. The mixture was quenched with H2O and extracted with EtOAc two times, dried over magnesium sulfate, filtered, concentrated. The title compound (653 mg, 70%) was isolated as a beige solid, and used as is for the next step.

Step 3: Synthesis of 6-(4,4,5,5-tetramethyl-1,3,2-dioxaborolan-2-yl)-2-naphthonitrile

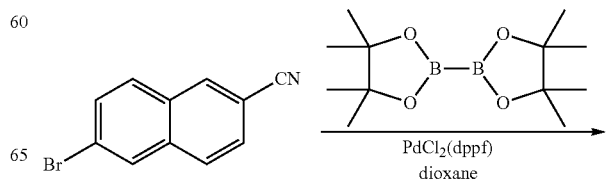

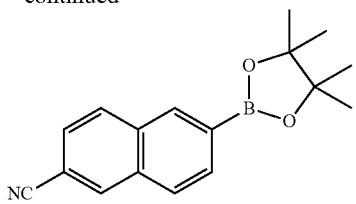

A mixture of 6-bromo-2-naphthonitrile (653 mg, 2.81 mmol), bis(pinacolato)diboron (857 mg, 3.38 mmol), potassium acetate (552 mg, 5.63 mmol) and PdC$_2$(dppf).CH$_2$Cl$_2$ adduct (115 mg, 0.141 mmol) in 1,4-dioxane (9.379 mL) was heated to 100° C. for 1 h. The mixture was concentrated, and the residue was purified via Biotage (0-10% EtOAc/heptane; SNAP50 column) giving the title compound (466 mg, 59%) as beige solid. $^1$H NMR (400 MHz, chloroform-d) δ ppm 1.33 (s, 12H) 7.53 (dd, J=8.53, 1.58 Hz, 1H) 7.80 (d, J=8.27 Hz, 1H) 7.83-7.92 (m, 2H) 8.15 (s, 1H) 8.32 (s, 1H).

Step 4: Synthesis of N-((5-(6-cyanonaphthalen-2-yl)pyridin-3-yl)(cyclopropyl)methyl)ethane-sulfonamide

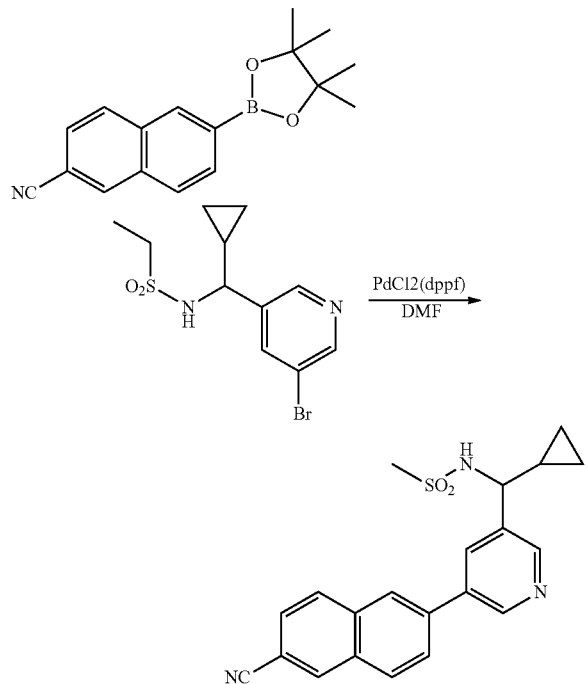

A mixture of 6-(4,4,5,5-tetramethyl-1,3,2-dioxaborolan-2-yl)-2-naphthonitrile (335 mg, 1.200 mmol), N-((5-bromopyridin-3-yl)(cyclopropyl)methyl)ethanesulfonamide (319 mg, 1 mmol), sodium carbonate (2 M) in water (1.000 mL, 2.000 mmol), PdCl$_2$(dppf).CH$_2$Cl$_2$ adduct (40.8 mg, 0.050 mmol) in DMF (4.000 mL) was heated to 100° C. for 30 min. The mixture was quenched with saturated aqueous NaHCO$_3$ and extracted with EtOAc two times, dried over magnesium sulfate, filtered, concentrated. The residue was purified via Biotage (10-100% EtOAc/heptane; SNAP25 column) giving the title compound (106 mg, 27%) as a white solid $^1$H NMR (400 MHz, MeOD) S ppm 0.43-0.55 (m, 1H) 0.56-0.69 (m, 2H) 0.69-0.83 (m, 1H) 1.28 (t, J=7.36 Hz, 3H) 1.25-1.39 (m, 1H) 2.82-3.10 (m, 2H) 3.95 (d, J=9.09 Hz, 1H) 7.73 (dd, J=8.53, 1.45 Hz, 1H) 8.00 (dd, J=8.59, 1.71 Hz, 1H) 8.15 (s, 1H) 8.17 (s, 1H) 8.28-8.35 (m, 2H) 8.44 (s, 1H) 8.65 (d, J=2.02 Hz, 1H) 8.90 (d, J=2.08 Hz, 1H). LC-MS (M+1) 392.2. Enantiomers were separated by chiral HPLC (IA 21×250 mm, flow rate: 14 mL/min, 60% heptane 20% methanol 20% ethanol) and yielded enantiomer-1 with retention time (14.10 min) and enantiomer-2 with retention time (18.16 min).

Examples 79-83 were prepared using the same procedure as described in step 4 of example 78. The syntheses of corresponding intermediates were as described below. Synthesis of 2-methyl-4-(4,4,5,5-tetramethyl-1,3,2-dioxaborolan-2-yl)benzonitrile

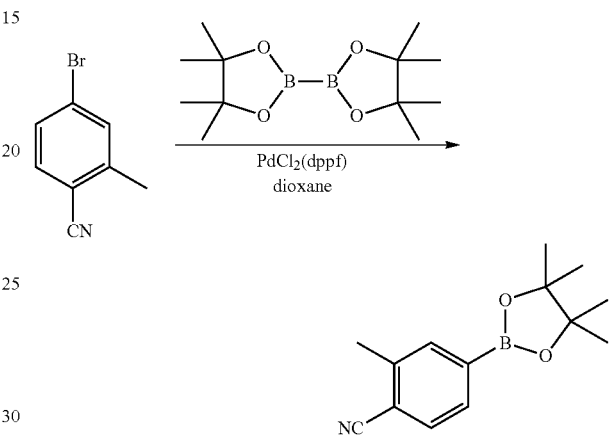

A mixture of 4-bromo-2-methylbenzonitrile (1 g, 5.10 mmol), bis(pinacolato)diboron (1.554 g, 6.12 mmol), potassium acetate (1.001 g, 10.20 mmol) and PdCl$_2$(dppf).CH$_2$Cl$_2$ adduct (0.208 g, 0.255 mmol) in 1,4-dioxane (12.75 ml) was heated to 80° C. for 5 h. The mixture was concentrated, and the residue was purified via Biotage (0-10% EtOAc/heptane; SNAP50 column) giving compound 2-methyl-4-(4,4,5,5-tetramethyl-1,3,2-dioxaborolan-2-yl)benzonitrile as a white solid (860 mg, 69%). $^1$H NMR (400 MHz, chloroform-d) d ppm 1.28 (s, 12H) 2.38-2.52 (m, 3H) 7.51 (d, J=7.64 Hz, 1H) 7.55-7.64 (m, 1H) 7.67 (s, 1H).

Synthesis of 5-cyanobenzofuran-2-ylboronic acid

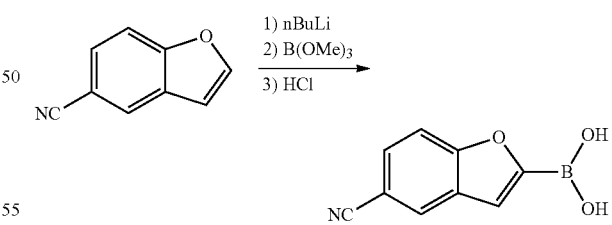

To benzofuran-5-carbonitrile (500 mg, 3.49 mmol) in THF (9.98 mL) at −78° C. was added nBuLi 1.6M in hexanes (2.401 mL, 3.84 mmol) dropwise. The mixture was stirred for 30 min at this temperature, and then trimethyl borate (0.858 mL, 7.68 mmol) was added dropwise. The mixture was stirred for 20 min, and then HCl 2N (11.52 mL, 23.05 mmol) was added. The bath was removed, and stirring continued for 30 min. The mixture was diluted with water and extracted with EtOAc three times, dried over magnesium sulfate, filtered, concentrated. Crude 5-cyanobenzofuran-2-ylboronic acid (623 mg, 87%) was then dried and used as is for the next step.

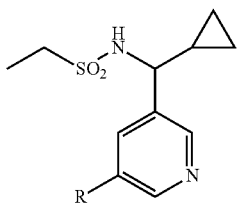

| Example | R | Name | Characterization | Chiral HPLC |
|---|---|---|---|---|
| 79 | quinolin-6-yl | N-(cyclopropyl(5-(quinolin-6-yl)pyridin-3-yl)methyl)ethane-sulfonamide | $^1$H NMR (400 MHz, MeOD) δ ppm 0.46-0.53 (m, 1H) 0.58-0.67 (m, 2H) 0.72-0.81 (m, 1H) 1.21-1.37 (m, 1H) 1.29 (t, J = 7.33 Hz, 3H) 2.88-3.08 (m, 2H) 3.95 (d, J = 9.09 Hz, 1H) 7.61 (dd, J = 8.34, 4.36 Hz, 1H) 8.11-8.20 (m, 2H) 8.28-8.34 (m, 2H) 8.47-8.52 (m, 1H) 8.64 (d, J = 2.08 Hz, 1H) 8.87-8.92 (m, 2H). LC-MS (M + 1) 392.2, t = 1.51 min. | |
| 80 | 4-cyano-3-methylphenyl | Enantiomer-1: (R)-N-((5-(4-cyano-3-methylphenyl)pyridin-3-yl)(cyclopropyl)methyl)ethane-sulfonamide Enantiomer-2: (S)-N-((5-(4-cyano-3-methylphenyl)pyridin-3-yl)(cyclopropyl)methyl)ethane-sulfonamide | $^1$H NMR (400 MHz, MeOD) δ ppm 0.43-0.50 (m, 1H) 0.56-0.65 (m, 2H) 0.69-0.82 (m, 1H) 1.26 (t, J = 7.33 Hz, 3H) 1.27-1.27 (m, 1H) 2.63 (t, J = 0.82 Hz, 3H) 2.87-3.06 (m, 2H) 3.91 (d, J = 9.16 Hz, 1H) 7.65-7.70 (m, 1H) 7.74-7.78 (m, 1H) 7.80 (d, J = 8.08 Hz, 1H) 8.18 (t, J = 2.21 Hz, 1H) 8.62-8.66 (m, 1H) 8.77 (d, J = 2.21 Hz, 1H). LC-MS (M + 1) 356.1, t = 1.43 min. | AS-H (21 × 250 mm 18 mL/min 80% heptane 20% ethanol) retention times for enatiomer-1 (11.58 min) and enatiomer-2 (15.08 min) |
| 81 | 5-cyanobenzofuran-2-yl | N-((5-(5-cyanobenzofuran-2-yl)pyridin-3-yl)(cyclopropyl)methyl)ethane-sulfonamide | $^1$H NMR (400 MHz, MeOD) δ ppm 0.41-0.54 (m, 1H) 0.54-0.70 (m, 2H) 0.70-0.83 (m, 1H) 1.18-1.38 (m, 1H) 1.28 (t, J = 7.33 Hz, 3H) 2.83-3.12 (m, 2H) 3.92 (d, J = 9.22 Hz, 1H) 7.54 (dd, J = 0.76, 0.19 Hz, 1H) 7.70 (dd, J = 8.59, 1.64 Hz, 1H) 7.71-7.84 (m, J = 8.59 Hz, 1H) 8.04-8.19 (m, 1H) 8.41 (t, J = 2.08 Hz, 1H) 8.64 (d, J = 2.08 Hz, 1H) 9.04 (d, J = 2.08 Hz, 1H). LC-MS (M + 1) 382.1, t = 1.50 min. | IA (21 × 250 mm 14 mL/min 40% heptane 60% ethanol) retention times for enantiomer-1: (12.94 min) and enantiomer-2: (16.92 min) |
| 82 | benzo[d]thiazol-5-yl | N-((5-(benzo[d]thiazol-5-yl)pyridin-3-yl)(cyclopropyl)methyl)ethane-sulfonamide | $^1$H NMR (400 MHz, MeOD) δ ppm 0.40-0.56 (m, 1H) 0.56-0.70 (m, 2H) 0.70-0.83 (m, 1H) 1.17-1.40 (m, 4H) 2.79-3.08 (m, 2H) 3.94 (d, J = 9.03 Hz, 1H) 7.84 (dd, J = 8.40, 1.77 Hz, 1H) 8.23 (d, J = 8.40 Hz, 1H) 8.25-8.32 (m, 1H) 8.38 (d, J = 1.45 Hz, 1H) 8.62 (d, J = 2.08 Hz, 1H) 8.84 (d, J = 2.15 Hz, 1H) 9.33 (s, 1H). LC-MS (M + 1) 374.1, t = 1.29 min. | |

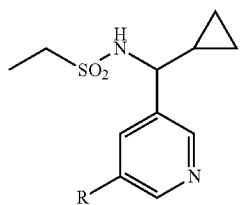

| Example | R | Name | Characterization | Chiral HPLC |
|---|---|---|---|---|
| 83 | benzofuran-5-yl | N-((5-(benzofuran-5-yl)pyridin-3-yl)(cyclopropyl)methyl)ethanesulfonamide | ¹H NMR (400 MHz, MeOD) δ ppm 0.41-0.56 (m, 1H) 0.56-0.68 (m, 2H) 0.68-0.84 (m, 1H) 1.22-1.39 (m, 4H) 2.83-3.09 (m, 2H) 3.91 (d, J = 9.09 Hz, 1H) 6.94 (dd, J = 2.21, 0.82 Hz, 1H) 7.52-7.71 (m, 2H) 7.82 (d, J = 2.21 Hz, 1H) 7.88-7.99 (m, 1H) 8.07-8.25 (m, 1H) 8.55 (d, J = 2.08 Hz, 1H) 8.75 (d, J = 2.15 Hz, 1H). LC-MS (M + 1) 357.1, t = 1.39 min. | |

Example 84

N-(5-(4-cyano-3-methyl phenyl)pyridin-3-yl)(4-fluorophenyl)methyl)ethane-sulfonamide

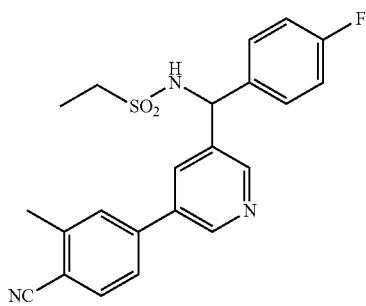 [SMILES: CCS(=O)(=O)NC(c1ccc(F)cc1)c1cncc(-c2ccc(C#N)c(C)c2)c1]

Step 1: Synthesis of N-((5-bromopyridin-3-yl)(4-fluorophenyl)methyl)ethanesulfonamide

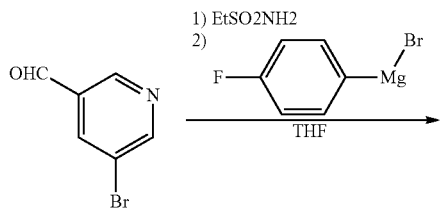

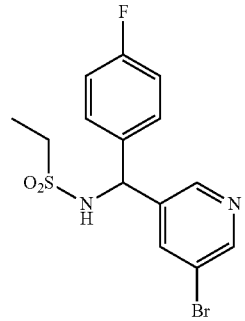

A mixture of 5-bromo-pyridine-3-carbaldehyde (0.930 g, 5 mmol), ethanesulfonamide (0.682 g, 6.25 mmol) and titanium(IV) isopropoxide (2.93 ml, 10.00 mmol) in toluene (10 mL) was heated to 100° C. for 4 h. After concentration, the residue was dissolved in THF (12.5 ml), and (4-fluorophenyl) magnesium bromide (1 M in THF, 12.50 mL, 12.50 mmol) was added dropwise at −78° C. The mixture was stirred at −78° C. for 45 min. The mixture was quenched with saturated NH₄Cl and extracted with EtOAc two times, dried over magnesium sulfate, filtered, and concentrated. The residue was purified via Biotage (10-40% AcOEt/heptane; SNAP25 column) giving the title compound (986 mg, 53%) as a beige solid. LC-MS (M+1) 375.0.

Step 2: Synthesis of N-((5-(4-cyano-3-methylphenyl)pyridin-3-yl)(4-fluorophenyl)methyl)ethane-sulfonamide

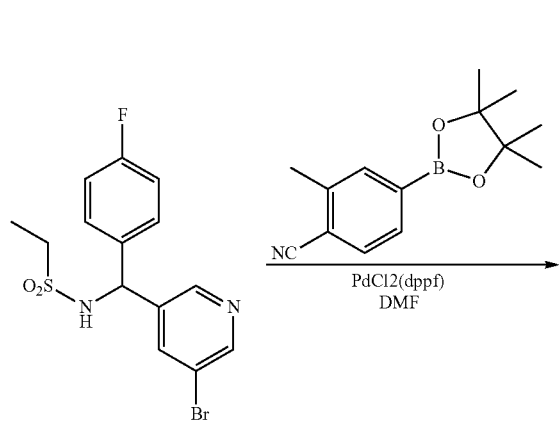

The title compound (413 mg, yield 75%) was obtained following the procedure described in step 4 of example 78. $^1$H NMR (400 MHz, MeOD) δ ppm 1.19 (t, J=7.39 Hz, 3H) 2.61 (s, 3H) 2.92-3.00 (m, 2H) 5.89 (s, 1H) 7.06-7.22 (m, 2H) 7.37-7.51 (m, 2H) 7.57-7.69 (m, 1H) 7.69-7.75 (m, 1H) 7.78 (d, J=8.02 Hz, 1H) 8.12 (td, J=2.15, 0.63 Hz, 1H) 8.55 (d, J=2.08 Hz, 1H) 8.78 (d, J=2.21 Hz, 1H). LC-MS (M+1) 410.3.

Example 85

N-(1-(5-(4-cyano-3-methyl phenyl)pyridin-3-yl)-2,2,2-trifluoroethyl)ethane-sulfonamide

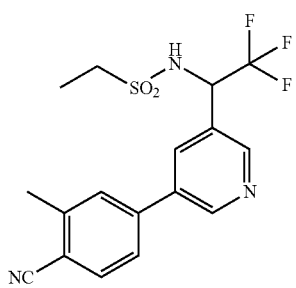 [SMILES: CCS(=O)(=O)NC(c1cncc(-c2ccc(C#N)c(C)c2)c1)C(F)(F)F]

Step 1: Synthesis of N-((5-bromopyridin-3-yl)methylene)-2-methylpropane-2-sulfinamide

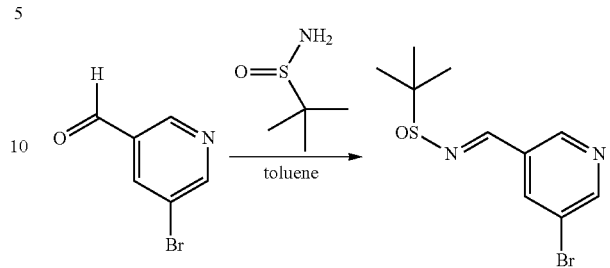

A mixture of 5-bromo-pyridine-3-carbaldehyde (2 g, 10.75 mmol), 2-methylpropane-2-sulfinamide (1.434 g, 11.83 mmol) and titanium(IV) isopropoxide (12.60 ml, 43.0 mmol) in toluene (53.8 ml) was stirred for 16 h at room temperature. Brine was added and the precipitate removed and washed with AcOEt. The organic layer was dried over MgSO4, filtered and concentrated to give the title compound that was used as is for the next step. LC-MS (M+1) 291.0.

Step 2: Synthesis of N-(1-(5-bromopyridin-3-yl)-2,2,2-trifluoroethyl)-2-methylpropane-2-sulfinamide

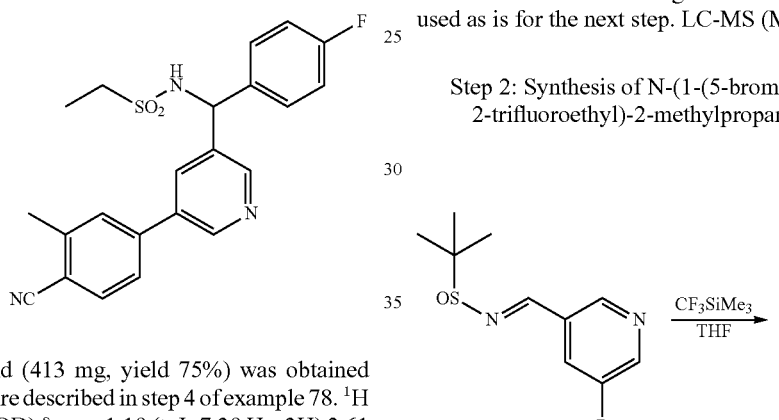

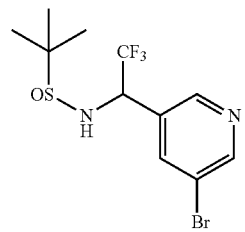

A mixture of N-((5-bromopyridin-3-yl)methylene)-2-methylpropane-2-sulfinamide (10.75 mmol) and tetrabutylammonium difluorotriphenylsilicate(IV) (6.38 g, 11.83 mmol) in THF (53.8 ml) was cooled to −78° C. Then (trifluoromethyl)trimethylsilane 2M solution in THF (6.45 ml, 12.90 mmol) was added dropwise, and the mixture stirred at −78° C. for 2 h. Brine was added and the precipitate removed and washed with AcOEt. The filtrates were dried over MgSO$_4$, filtered and concentrated. The residue was purified via Biotage (0-15%

MeOH/CH₂Cl₂; SNAP50 column) giving the title compound (2.96 g, 77%) as a light yellow solid. LC-MS (M+1) 361.0.

Step 3: Synthesis of 1-(5-bromopyridin-3-yl)-2,2,2-trifluoroethanamine

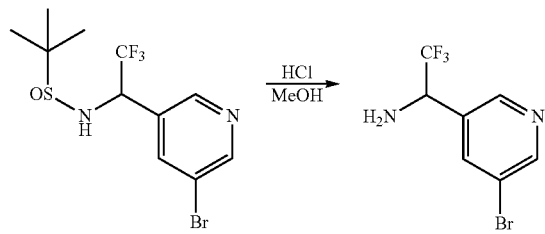

To N-(1-(5-bromopyridin-3-yl)-2,2,2-trifluoroethyl)-2-methylpropane-2-sulfinamide (1.5 g, 4.18 mmol) in MeOH (8.35 ml) was added HCl 4N in dioxane (2.088 ml, 8.35 mmol) dropwise, and the mixture stirred at room temperature for 16 h. Concentrated, and then the mixture was quenched with saturated NaHCO₃ and extracted with EtOAc two times, dried over magnesium sulfate, filtered, concentrated. The title compound was isolated as a light yellow oil used as is for next step. LC-MS (M+1) 257.0, t=1.05 min

Step 4: Synthesis of 4-(5-(1-amino-2,2,2-trifluoroethyl)pyridin-3-yl)-2-methylbenzonitrile

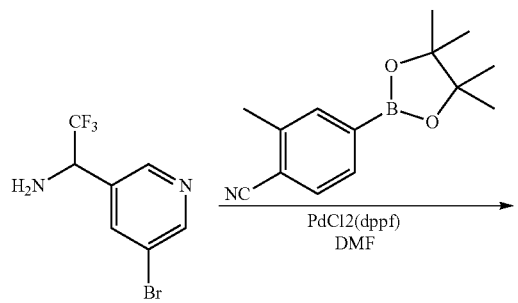

The title compound (322 mg, 53%) was obtained following the procedure described above for in step 4 of example 78. LC-MS (M+1) 292.2.

Step 5: Synthesis of N-(1-(5-(4-cyano-3-methyl phenyl)pyridin-3-yl)-2,2,2-trifluoroethyl)ethane-sulfonamide

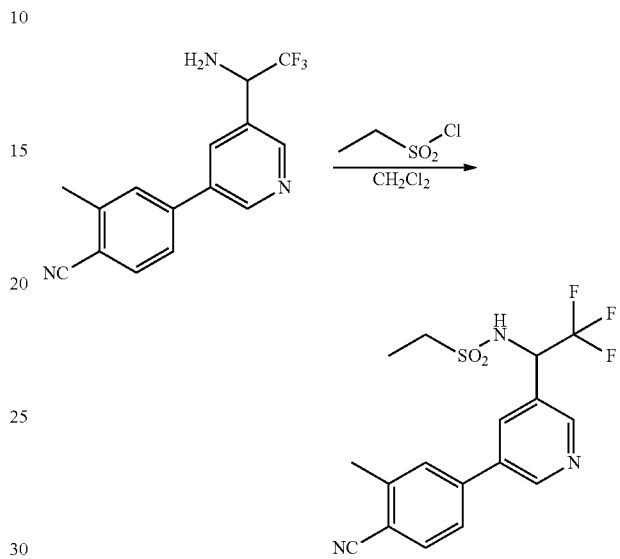

To a solution of 4-(5-(1-amino-2,2,2-trifluoroethyl)pyridin-3-yl)-2-methylbenzonitrile (322 mg, 1.105 mmol) in CH₂Cl₂ (5.5 mL) at 0° C. was added triethylamine (462 μl, 3.32 mmol) and ethanesulfonyl chloride (115 μl, 1.216 mmol). The mixture was stirred for 16 h at room temperature. The mixture was quenched with saturated NaHCO₃ and extracted with EtOAc two times, dried over magnesium sulfate, filtered, concentrated. The residue was purified via Biotage (10-50% EtOAc/heptane; SNAP25 column) giving the title compound (67 mg, 16%). LC-MS (M+1) 384.1. ¹H NMR (400 MHz, MeOD) δ ppm 1.28 (t, J=7.33 Hz, 3H) 2.63 (s, 3H) 2.96-3.19 (m, 2H) 5.47 (q, J=7.89 Hz, 1H) 7.66-7.72 (m, 1H) 7.76-7.79 (m, 1H) 7.81 (d, J=8.02 Hz, 1H) 8.24-8.43 (m, 1H) 8.76 (d, J=2.27 Hz, 1H) 8.93 (d, J=2.21 Hz, 1H).

The enantiomers were separated by chiral HPLC (OD-H, 21×250 mm, 18 mL/min, 70% heptane 30% ethanol) to enantiomer-1 with retention time (7.03 min) and enantiomer-2 with retention time (11.46 min).

Example 86

N-(2-(5-(2,3-dichlorophenyl)pyridin-3-yl)ethyl) ethanesulfonamide

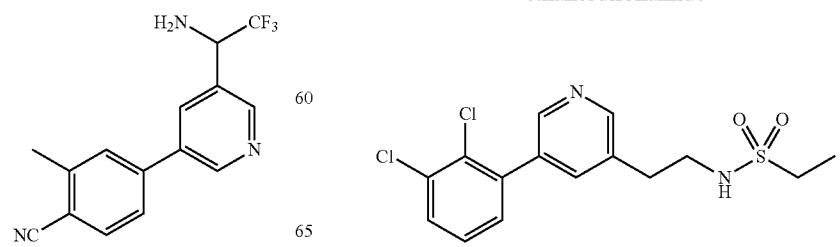

Step 1: Synthesis of 3-(5-bromopyridin-3-yl)acrylate

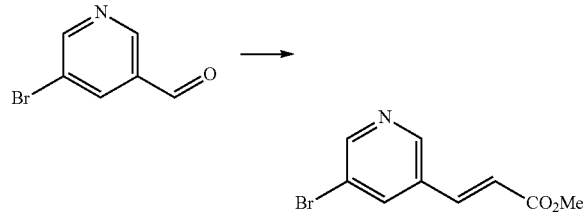

To a solution of methyl diethylphosphonoacetate (2.4 ml, 13.13 mmol) in THF (40 mL) at 0° C. was added BuLi (8.21 ml, 13.13 mmol) dropwise. After 10 min, a solution of 5-bromo-3-pyridinecarboxaldehyde (2.443 g, 13.13 mmol) in THF (10 mL) was added at the this temperature. The reaction mixture was warmed to room temperature and stirred for 30 min, then quenched by water. The mixture was extracted with EtOAc, washed with brine The combined organic layer was dried over $Na_2SO_4$, filtered and concentrated to give 3-(5-bromopyridin-3-yl)acrylate (3.25 g, 13.43 mmol, 100% yield) as a white solid. ESI-MS m/z: 243 [M+1]+; 1HNMR (MeOD, 400 MHz) δ 3.80 (s, 3H), 6.52 (d, J=16 Hz, 1H), 7.63 (d, J=16 Hz, 1H), 8.33 (s, 1H), 8.64 (s, 1H), 8.72 (s, 1H).

Step 2: Synthesis of 3-[5-(2,3-Dichloro-phenyl)-pyridin-3-yl]-acrylic acid methyl ester

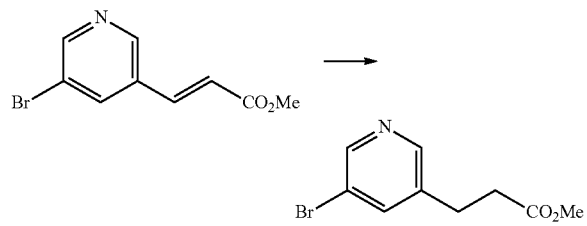

To a solution of 3-(5-bromopyridin-3-yl)acrylate (180 mg, 0.744 mmol) and nickel chloride hexahydrate (17.6 mg, 0.074 mmol) in MeOH (3 ml) was added sodium borohydride (56.3 mg, 1.487 mmol) at 0° C. This mixture was stirred for 30 min at room temperature. Brine and ethyl acetate were added and the organic layer was separated and washed with brine twice. The combined organic layer was dried over $Na_2SO_4$, filtered and concentrated to give 155 mg of crude 3-(5-Bromo-pyridin-3-yl)-propionic acid methyl ester. ESI-MS m/z: 246[M+1]+.

Step 3: Synthesis of 3-[5-(2,3-Dichloro-phenyl)-pyridin-3-yl]-propionic acid methyl ester

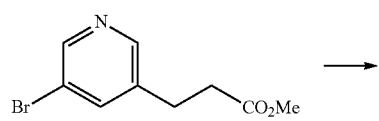

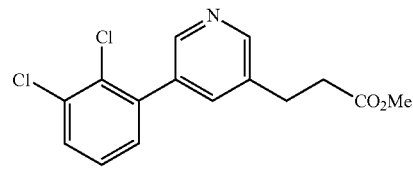

A mixture of 3-(5-bromo-pyridin-3-yl)-propionic acid methyl ester (155 mg), 2,3-dichlorobenzeneboronic acid (142 mg, 0.744 mmol), $PdCl_2(dppf).CH_2Cl_2$ adduct (48.6 mg, 0.059 mmol) and $Na_2CO_3$ (2 M, 0.929 ml, 1.859 mmol) in DMF (5 ml) was heated at 100° C. After 40 min, solvent was removed in vacuo. The residue was purified via flash column (EtOAc/Heptane=0-20-25%, v/v) to give 3-[5-(2,3-Dichloro-phenyl)-pyridin-3-yl]-propionic acid methyl ester (101 mg, 0.326 mmol, 43% yield). ESI-MS m/z: 310[M+1]+; 1H NMR ($CDCl_3$, 400 MHz) δ 2.71 (t, J=7.6 Hz, 2H), 3.05 (t, J=7.6 Hz, 2H), 3.70 (s, 3H), 7.23 (dd, J=7.6, 1.6 Hz, 1H), 7.30 (t, J=7.6 Hz, 1H), 7.53 (dd, J=7.6, 1.6 Hz, 1H), 7.63 (s, 1H), 8.52 (s, 2H).

Step 4: Synthesis of 3-[5-(2,3-Dichloro-phenyl)-pyridin-3-yl]-propionamide

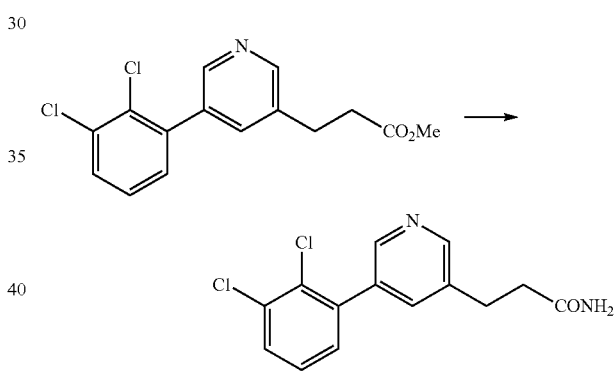

A mixture of 3-[5-(2,3-dichloro-phenyl)-pyridin-3-yl]-propionic acid methyl ester and ammonia (7N in MeOH, 2 ml, 14.00 mmol) was stirred at room temperature for 24 hours. Ammonia (7N in MeOH, 1 ml, 7.00 mmol) was added, and the reaction mixture was stirred for another 24 hours. Solvent was removed in vacuo. The crude product was used in the next step without purification. ESI-MS m/z: 295 [M+1]+.

Step 5: Synthesis of 2-[5-(2,3-dichloro-phenyl)-pyridin-3-yl]-ethylamine

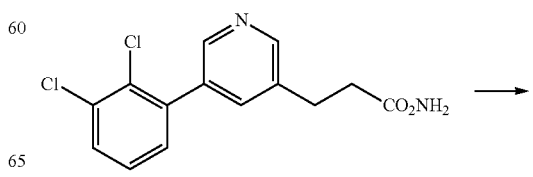

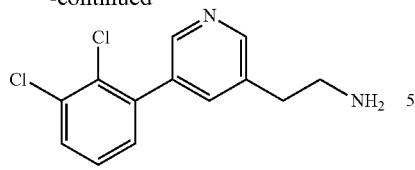

A solution of sodium hydroxide (78 mg, 1.951 mmol) in water (4 ml) was cooled to 0° C. and bromine (0.020 ml, 0.390 mmol) was added. After the mixture was stirred for a few minutes, 3-(5-(2,3-dichlorophenyl)pyridin-3-yl)propanamide (96 mg, 0.325 mmol) in EtOH (1.000 ml) was added. Stirring was continued at 0° C. until the solution became clear. The reaction temperature was raised to 95° C. and stirred for 1 h. The reaction mixture was diluted with dichloromethane and extracted with dichloromethane. The combined organic layer was dried over $Na_2SO_4$, filtered and concentrated under reduced pressure. Crude 2-(5-(2,3-dichlorophenyl)pyridin-3-yl)ethanamine (35 mg, 0.131 mmol, 40.3% yield) was obtained and used in next step without further purification.

ESI-MS m/z: 267 [M+1]$^+$.

Step 6: Synthesis of N-(2-(5-(2,3-dichlorophenyl)pyridin-3-yl)ethyl)ethanesulfonamide

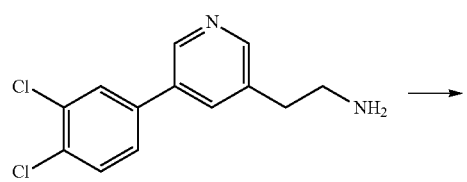

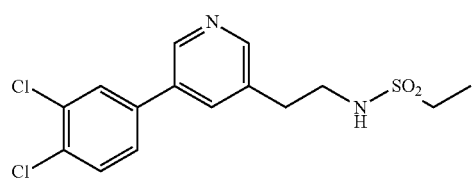

To a solution of 2-(5-(2,3-dichlorophenyl)pyridin-3-yl)ethanamine (35 mg, 0.131 mmol) in pyridine (3 ml) at 0° C. was added ethanesulfonyl chloride (0.037 ml, 0.393 mmol) and the resulting mixture was stirred at room temperature for 2 h. The reaction mixture was diluted with EtOAc and water, extracted with EtOAc. The combined organic layer was dried over $Na_2SO_4$, filtered and concentrated under reduced pressure. Purification via PTLC (eluent; 60% EtOAc/Heptane, v/v) gave N-(2-(5-(2,3-dichlorophenyl)pyridin-3-yl)ethyl)ethanesulfonamide (8.1 mg, 0.023 mmol, 17% yield).

ESI-MS m/z: 359 [M+1]$^+$.

$^1$H NMR (MeOD, 400 MHz) δ 1.33 (t, J=7.2 Hz, 3H), 2.99 (t, J=7.6 Hz, 2H), 3.01 (t, J=7.6 Hz, 2H), 3.47 (q, J=7.2 Hz, 2H), 4.33 (s, 1H), 7.25 (dd, J=7.6, 1.6 Hz, 1H), 7.31 (t, J=7.6 Hz, 1H), 7.54 (dd, J=7.6, 1.6 Hz, 1H), 7.69 (t, J=2.0 Hz, 1H), 8.54 (s, 1H), 8.57 (s, 1H).

Example 87

N-(2-(5-(2,3-dichlorophenyl)pyridin-3-yl)cyclopropyl)ethane-sulfonamide

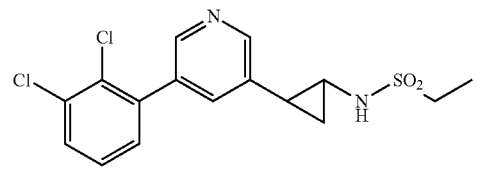 [SMILES: CCS(=O)(=O)NC1CC1c1cncc(-c2cccc(Cl)c2Cl)c1]

Step 1: Synthesis of methyl 2-(5-bromopyridin-3-yl)cyclopropanecarboxylate

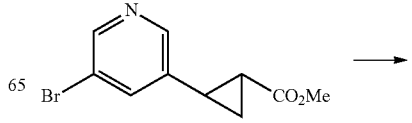

DMSO (20 ml) was added slowly to a mixture of sodium hydride (0.215 g, 5.37 mmol) and trimethylsulfoxonium iodide (1.227 g, 5.58 mmol). The mixture was stirred at room temperature for 15 min, and then (E)-methyl 3-(5-bromopyridin-3-yl)acrylate (1 g, 4.13 mmol) in DMSO (8 ml) was added. The reaction mixture was stirred at room temperature for 3 min. Ice water and EtOAc were added. The organic layer was washed with water and brine. The aqueous layer was extracted with EtOAc twice. The combined organic layer was dried over $Na_2SO_4$, filtered and concentrated. The residue was purified via flash column (EtOAc/Heptane=0-30%, v/v) to give methyl 2-(5-bromopyridin-3-yl)cyclopropanecarboxylate (257 mg, 1.004 mmol, 24% yield). ESI-MS m/z: 358[M+1]$^+$; $^1$H NMR (CDCl$_3$, 400 MHz); δ 1.33-1.38 (m, 1H), 1.66-1.71 (m, 1H), 1.94-1.98 (m, 1H), 2.49-2.54 (m, 1H), 3.75 (s, 3H), 7.51 (t, J=2.0 Hz, 1H), 8.37 (d, J=2.0 Hz, 1H), 8.53 (t, J=2.0 Hz, 1H).

Step 2: Synthesis of methyl 2-(5-(2,3-dichlorophenyl)pyridin-3-yl)cyclopropanecarboxylate -continued

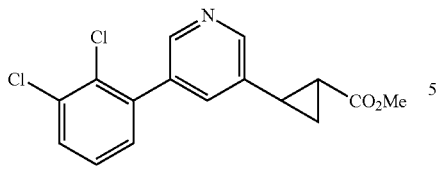

A mixture of 2,3-dichlorophenylboronic acid (279 mg, 1.464 mmol), methyl 2-(5-bromopyridin-3-yl)cyclopropanecarboxylate (357 mg, 1.394 mmol), PdCl$_2$(dppf).CH$_2$Cl$_2$ adduct (114 mg, 0.139 mmol) and Na$_2$CO$_3$ (2 M in water, 1.743 ml, 3.49 mmol) in DMF (7 ml) was heated at 100° C. under nitrogen atmosphere. After 1 h, the solvent was removed under vacuo. The residue was purified by flash column (EtOAc/Heptane=0-25%, v/v) to give methyl 2-(5-(2,3-dichlorophenyl)pyridin-3-yl)cyclopropanecarboxylate (335 mg, 1.040 mmol, 74% yield). ESI-MS m/z: 322[M+1]$^+$; $^1$H NMR (CDCl$_3$, 400 MHz) 1.38-1.41 (m, 1H), 1.68-1.73 (m, 1H), 1.97-2.01 (m, 1H), 2.58-2.63 (m, 1H), 3.75 (s, 3H), 7.21 (dd, J=7.6, 1.2 Hz, 1H), 7.30 (t, J=7.6 Hz, 1H), 7.43 (bs, 1H), 7.53 (dd, J=7.6, 1.2 Hz, 1H), 8.48 (d, J=1.6 Hz, 1H), 8.50 (d, J=1.6 Hz, 1H), Step 3: Synthesis of benzyl 2-(5-(2,3-dichlorophenyl)pyridin-3-yl)cyclopropylcarbamate

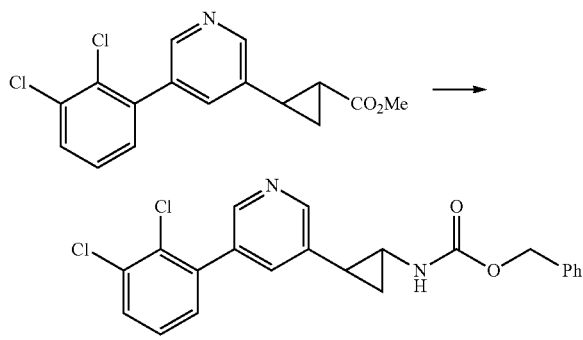

To a solution of methyl 2-(5-(2,3-dichlorophenyl)pyridin-3-yl)cyclopropanecarboxylate (270 mg, 0.838 mmol) in MeOH (3 ml) was added NaOH (5 M in water, 0.503 ml, 2.51 mmol) at room temperature. The resulting mixture was stirred at room temperature for 30 min. The reaction was quenched by the addition of HCl (5 M in water), and the mixture was extracted with AcOEt/trifluoroethanol (10:1). The extract was washed with water and brine, dried over Na$_2$SO$_4$, filtered and concentrated in vacuo. The resulting crude was dissolved in toluene (7 ml). Diphenylphosphonoazide (0.272 ml, 1.257 mmol), triethylamine (0.175 ml, 1.257 mmol) were added to the solution, which was stirred for 12 h at 100° C. Benzyl alcohol (0.523 ml, 5.03 mmol) was added to the reaction mixture and this mixture was stirred for additional 4 h. A saturated NaHCO$_3$ solution was added at room temperature and the mixture was extracted with AcOEt. The extract was washed with water and brine, dried over Na$_2$SO$_4$, filtered and concentrated in vacuo. Purification by flash column (EtOAc/Heptane=0-50%, v/v) gave benzyl 2-(5-(2,3-dichlorophenyl) pyridin-3-yl)cyclopropylcarbamate (94.1 mg, 0.228 mmol, 27% yield) ESI-MS m/z: 413[M+1]$^+$. $^1$H NMR (CDCl$_3$, 400 MHz) δ ppm 1.27-1.33 (m, 2H), 2.15-2.28 (m, 1H), 2.81- 2.87 (m, 1H), 5.13 (s, 2H), 7.21 (bs, 1H), 7.29 (t, J=8.0 Hz, 1H), 7.35 (s, 5H), 7.52 (dd, J=8.0, 0.6 Hz, 2H), 8.48 (s, 2H)

Step 4: Synthesis of N-2-(5-(2,3-dichlorophenyl) pyridin-3-yl)cyclopropyl)ethanesulfonamide

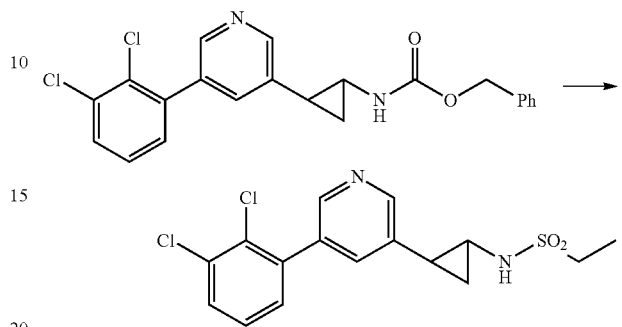

To a solution of benzyl 2-(5-(2,3-dichlorophenyl)pyridin-3-yl)cyclopropylcarbamate (94 mg, 0.227 mmol) in DCM (3 ml) was added BBr$_3$ (0.682 ml, 0.682 mmol) at 0° C. This reaction mixture was stirred for 1 h at 0° C. The reaction was quenched by addition of saturated NaHCO$_3$ solution, and the mixture was extracted with AcOEt. The extract was washed with brine, dried over Na$_2$SO$_4$, filtered and concentrated in vacuo. The residue was dissolved in pyridine (3.00 ml), and ethanesulfonyl chloride (0.086 ml, 0.910 mmol) was added to the solution. This reaction mixture was stirred at room temperature. After 1 h, saturated NH$_4$Cl solution in water was added. The mixture was extracted with AcOEt. The extract was washed with brine, dried over Na$_2$SO$_4$, filtered and concentrated in vacuo. The residue was purified by flash column (EtOAc/Heptane=0-50%, v/v) gave N-(2-(5-(2,3-dichlorophenyl)pyridin-3-yl)cyclopropyl)ethanesulfonamide (6.2 mg, 0.017 mmol, 7% yield). ESI-MS m/z: 371[M+1]$^+$. $^1$H NMR (CDCl$_3$, 400 MHz) 1.31 (t, J=7.2 Hz, 3H), 1.38-1.43 (m, 2H), 2.35-2.38 (m, 1H), 2.86-2.91 (m, 1H), 3.14 (q, J=7.2 Hz, 2H), 7.41 (dd, J=7.6, 2.0 Hz, 1H), 7.47 (t, J=7.6 Hz, 1H), 7.57 (t, J=2.0 Hz, 1H), 7.65 (dd, J=7.6, 2.0 Hz, 1H), 8.46 (d, J=2.4 Hz, 1H), 8.53 (d, J=2.4 Hz, 1H).

It can be seen that the compounds of this invention are useful as inhibitors of aldosterone synthase activity and therefore useful in the treatment of diseases and conditions mediated by aldosterone synthase such as the metabolic disorders disclosed herein.

It will be understood that the invention has been described by way of example only and modifications may be made whilst remaining within the scope and spirit of the invention.

The invention claimed is:
1. A Compound of Formula (I'):

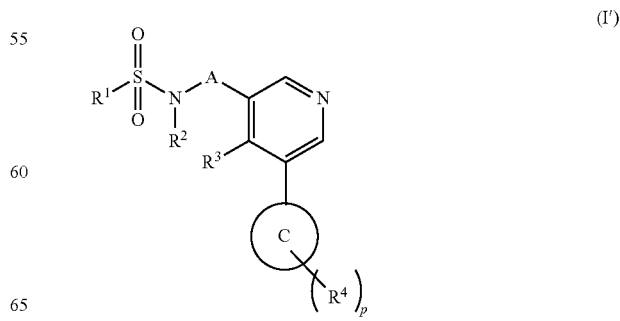

or a pharmaceutically acceptable salt thereof, wherein
A is —CH$_2$—, —CHR$^5$—, —CR$^5$R$^6$— or —CR$^{5a}$R$^{6a}$—CR$^{5b}$R$^{6b}$—;
Ring C is a phenyl;
R$^1$ is C$_{1-7}$alkyl, haloalkyl, C$_{3-7}$cycloalkyl, C$_{6-10}$aryl, C$_{6-10}$aryl-C$_{1-7}$alkyl, C$_{6-10}$aryloxy-C$_{1-7}$alkyl, heteroaryl or heterocyclyl in which alkyl, aryl, heteroaryl, heterocyclyl are optionally substituted with 1 to 5 R$^7$;
R$^2$ is H, C$_{1-7}$alkyl, halo-C$_{1-7}$alkyl, C$_{3-7}$cycloalkyl, C$_{3-7}$cycloalkyl-C$_{1-7}$alkyl, hydroxy-C$_{1-7}$alkyl, C$_{1-7}$alkyl-OC(O)C$_{1-7}$alkyl, C$_{1-7}$alkoxy-C$_{1-7}$alkyl, heteroaryl, heterocycyl, or C$_{6-10}$aryl; wherein aryl and heteroaryl are optionally substituted with hydroxy, C$_{1-7}$alkoxy, C$_{1-7}$alkyl, halo-C$_{1-7}$alkyl, halo, CN or C$_{3-7}$cycloalkyl;
R$^3$ is H, halo, C$_{1-7}$alkyl, halo-C$_{1-7}$alkyl, C$_{3-7}$cycloalkyl, cyano, C$_{1-7}$alkoxy, hydroxy, nitro, —NH$_2$, —NH(C$_{1-7}$alkyl) or —N(C$_{1-7}$alkyl)$_2$;
two adjacent R$^4$ groups form, with the atoms to which they are attached, a phenyl or a 5- or 6-membered ring heteroaryl, in which said phenyl or heteroaryl ring is optionally substituted with 1 to 4 R$^8$; and
each optional additional R$^4$ is independently selected from the group consisting of halo, C$_{1-7}$alkyl, halo-C$_{1-7}$alkyl, C$_{3-7}$cycloalkyl, cyano, —NH$_2$, —NH(C$_{1-7}$alkyl), —N(C$_{1-7}$alkyl)$_2$, C$_{1-7}$alkoxy, halo-C$_{1-7}$alkoxy, hydroxy, carboxy, nitro, sulfonyl, sulfamoyl, sulfonamido, C$_{6-10}$aryl, heterocyclyl, C$_{6-10}$aryloxy, heterocyclyloxy, —SH, —C(O)O—C$_{6-10}$aryl, —C(O)O-heterocyclyl, —C(O)O-heteroaryl, —C(O)NR$^2$—C$_{1-7}$alkyl, —C(O)NR$^2$—C$_{6-10}$aryl, —C(O)NR$^2$-heteroaryl, —C(O)NR$^2$-heterocyclyl, —NR$^2$C(O)—C$_{1-7}$alkyl, —NR$^2$C(O)—C$_{6-10}$aryl, —NR$^2$C(O)-heteroaryl, —NR$^2$C(O)-heterocyclyl, —OC(O)—C$_{1-7}$alkyl, —OC(O)—C$_{6-10}$aryl, —OC(O)-heteroaryl and —OC(O)-heterocyclyl; wherein R$^4$ is optionally substituted with 1 to 5 R$^7$;
R$^5$ and R$^6$ are independently C$_{1-7}$alkyl, C$_{3-7}$cycloalkyl, halo-C$_{1-7}$alkyl, heterocyclyl, heteroaryl or C$_{6-10}$aryl; or R$^5$ and R$^6$ form together with the atom to which they are attached a C$_{3-7}$cycloalkyl;
R$^{5a}$, R$^{6a}$, R$^{5b}$ and R$^{6b}$ are independently H, C$_{1-7}$alkyl, C$_{3-7}$cycloalkyl, halo-C$_{1-7}$alkyl, heterocyclyl, heteroaryl or C$_{6-10}$aryl; or any two of R$^{5a}$, R$^{6a}$, R$^{5b}$ and R$^{6b}$ form together with the atom(s) to which they are attached a C$_{3-7}$cycloalkyl;
each R$^7$ is independently selected from the group consisting of halo, C$_{1-7}$alkyl, C$_{3-7}$cycloalkyl, C$_{1-7}$alkoxy, C$_{6-10}$aryloxy, heterocyclyl, C$_{6-10}$aryl, heteroaryl, CN and halo-C$_{1-7}$alkyl;
each R$^8$ is independently selected from the group consisting of halo, C$_{1-7}$alkyl, halo-C$_{1-7}$alkyl, C$_{1-7}$alkoxy, CN and halo-C$_{1-7}$alkoxy; or
R$^2$ and R$^3$; R$^1$ and R$^2$; R$^1$ and R$^5$; R$^1$ and R$^{5a}$; R$^1$ and R$^{5b}$; R$^2$ and R$^{5a}$; R$^2$ and R$^{5b}$; R$^1$ and R$^3$;
or R$^2$ and R$^5$ can form with the atoms to which they are attached a 4- to 7-membered heterocyclyl; or
R$^3$ and R$^5$; R$^3$ and R$^{5b}$; or R$^3$ and R$^{5a}$ can form together with the atoms to which they are attached a C$_{5-7}$cycloalkyl; and
wherein each heteroaryl is a monocyclic aromatic ring comprising 5 or 6 ring atoms selected from carbon atoms and 1 to 5 heteroatoms, and
each heterocyclyl is a monocyclic saturated or partially saturated but non-aromatic moiety comprising 4-7 ring atoms selected from carbon atoms and 1 to 3 heteroatoms; and
each heteroatoms being O, N or S;
p is 2, 3, 4 or 5, with the proviso that the compound of Formula I' is not 2-methyl-N-(6-(5-(phenylsulfonamido)pyridin-3-yl)-1H-indazol-4-yl)thiazole-4-carboxamide.

2. The compound of claim 1 having Formula (III):

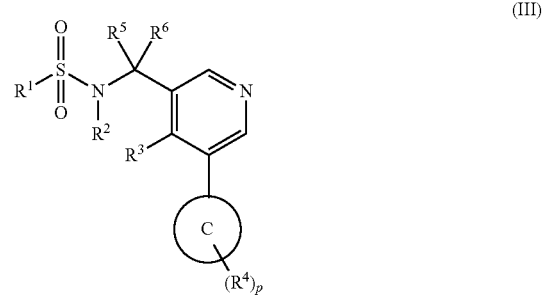

(III)

or a pharmaceutically acceptable salt thereof, wherein C, R$^1$, R$^2$, R$^3$, R$^4$, R$^5$, R$^6$ and p are as defined in claim 1.

3. The compound of claim 1 having Formula (V):

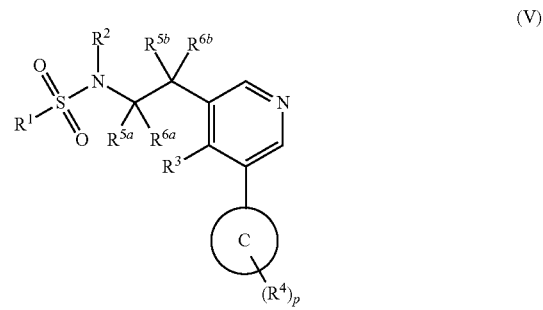

(V)

or a pharmaceutically acceptable salt thereof, wherein C, R$^1$, R$^2$, R$^3$, R$^4$, R$^{5a}$, R$^{6a}$, R$^{5b}$, R$^{6b}$ and p are as defined in claim 1.

4. The compound of claim 1, or a pharmaceutically acceptable salt thereof, wherein Ring C together with 2 R$^4$ groups, is

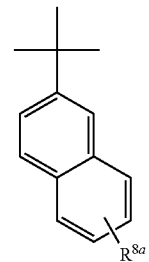

wherein R$^{8a}$ is R$^8$ or H.

5. The compound according to claim 1, or a pharmaceutically acceptable salt thereof, wherein A is CHR$^5$.

6. The compound of claim 1, or a pharmaceutically salt thereof wherein R$^1$ is C$_{1-4}$alkyl, R$^2$ is H, R$^3$ is H, A is CHR$^5$, R$^5$ is C$_{1-4}$alkyl or C$_{3-6}$cycloalkyl, p is 1 or 2.

7. The compound of claim 1 selected from the group consisting of:
N-((5-(6-cyanonaphthalen-2-yl)pyridin-3-yl)(cyclopropyl)methyl)ethane-sulfonamide;
N-(cyclopropyl(5-(quinolin-6-yl)pyridin-3-yl)methyl)ethanesulfonamide;

N-((5-(benzo[d]thiazol-5-yl)pyridin-3-yl)(cyclopropyl)methyl)ethanesulfonamide; and N-((5-(benzofuran-5-yl)pyridin-3-yl)(cyclopropyl)methyl)ethanesulfonamide; or a pharmaceutically acceptable salt thereof.

8. A pharmaceutical composition comprising a therapeutically effective amount of the compound according to claim 1, or a pharmaceutically acceptable salt thereof, and one or more pharmaceutically acceptable carriers.

9. A pharmaceutical combination, comprising a therapeutically effective amount of the compound according to claim 1, or a pharmaceutically acceptable salt thereof, and one or more therapeutically active agents selected from the group consisting of an HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, and a CETP inhibitor.

10. A method of inhibiting aldosterone synthase activity in a subject in need thereof, comprising: administering to the subject a therapeutically effective amount of the compound according to claim 1, or a pharmaceutically acceptable salt thereof.

11. A method of treating a disorder or a disease in a subject mediated by aldosterone synthase, comprising:

Administering to the subject a therapeutically effective amount of the compound according to claim 1, or a pharmaceutically acceptable salt thereof.

12. A method according to claim 11, wherein the disorder or the disease is selected from the group consisting of hypokalemia, hypertension, Conn's disease, renal failure, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries.

* * * * *